(12) United States Patent
Tu et al.

(10) Patent No.: US 9,572,963 B2
(45) Date of Patent: *Feb. 21, 2017

(54) OCULAR DISORDER TREATMENT METHODS AND SYSTEMS

(71) Applicant: Glaukos Corporation, Laguna Hills, CA (US)

(72) Inventors: Hosheng Tu, Newport Coast, CA (US); Barbara A. Niksch, Capistrano Beach, CA (US); David Steven Haffner, Mission Viejo, CA (US); Gregory T. Smedley, Aliso Viejo, CA (US); Richard A. Hill, Irvine, CA (US); Olav B. Bergheim, Laguna Hills, CA (US)

(73) Assignee: Glaukos Corporation, San Clemente, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/786,363

(22) Filed: Mar. 5, 2013

(65) Prior Publication Data

US 2013/0245532 A1    Sep. 19, 2013

Related U.S. Application Data

(60) Continuation of application No. 13/301,648, filed on Nov. 21, 2011, now Pat. No. 8,579,846, which is a
(Continued)

(51) Int. Cl.
*A61M 5/00* (2006.01)
*A61M 27/00* (2006.01)
*A61F 9/007* (2006.01)

(52) U.S. Cl.
CPC .......... *A61M 27/00* (2013.01); *A61F 9/00781* (2013.01)

(58) Field of Classification Search
CPC ..................... A61M 27/00; A61F 9/00781
(Continued)

(56) References Cited

U.S. PATENT DOCUMENTS

| 2,031,754 A | 2/1936 | Mills |
| 2,127,903 A | 8/1938 | Bowen |

(Continued)

FOREIGN PATENT DOCUMENTS

| AU | 200072059 A1 | 7/2001 |
| AU | 2004264913 | 2/2005 |

(Continued)

OTHER PUBLICATIONS

Portney, GL. "Silicone Elastomer Implantation Cyclodialysis," Arch Ophthalmol. 89, 10-12 (1973).*

(Continued)

*Primary Examiner* — Leslie Deak
(74) *Attorney, Agent, or Firm* — Knobbe Martens Olson & Bear, LLP

(57) ABSTRACT

An embodiment of a system for shunting aqueous humor from an anterior chamber of an eye includes an implant having an elongated body made of biocompatible material and a delivery device. At least a portion of the elongated body is implantable between a sclera and a ciliary body while the elongated body resides entirely within the confines of the sclera and a cornea with the proximal end of the implant being configured to reside within an anterior chamber angle and a lumen extending from at least one inlet port of the implant, through at least a portion of the elongated body, to one or more outlet ports of the implant so as to drain fluid from the anterior chamber toward a choroid of the eye. The delivery device includes an elongated member with a curved distal end portion to deliver the implant using an ab interno procedure.

38 Claims, 36 Drawing Sheets

Related U.S. Application Data continuation of application No. 12/366,508, filed on Feb. 5, 2009, now Pat. No. 8,062,244, which is a division of application No. 11/598,542, filed on Nov. 13, 2006, now Pat. No. 7,563,241, which is a continuation of application No. 10/118,578, filed on Apr. 8, 2002, now Pat. No. 7,135,009.

(60) Provisional application No. 60/281,973, filed on Apr. 7, 2001.

(58) Field of Classification Search
USPC ......... 604/8, 9, 264; 623/4.1, 6.12; 606/107, 606/108
See application file for complete search history.

(56) References Cited

U.S. PATENT DOCUMENTS

| | | |
|---|---|---|
| 2,269,963 A | 1/1942 | Frederick |
| 3,159,161 A | 12/1964 | Ness |
| 3,439,675 A | 4/1969 | Cohen |
| 3,717,151 A | 2/1973 | Collett |
| 3,788,327 A | 1/1974 | Donowitz et al. |
| 3,827,700 A | 8/1974 | Kaller |
| 3,863,623 A | 2/1975 | Trueblood et al. |
| 3,915,172 A | 10/1975 | Krejci et al. |
| 3,948,271 A | 4/1976 | Aklyama |
| 3,948,871 A | 4/1976 | Butterfield et al. |
| 3,976,077 A | 8/1976 | Kerfoot, Jr. |
| 4,037,604 A | 7/1977 | Newkirk |
| 4,043,346 A | 8/1977 | Mobley et al. |
| 4,113,088 A | 9/1978 | Binkhorst |
| 4,168,697 A | 9/1979 | Cantekin |
| 4,175,563 A | 11/1979 | Arenberg et al. |
| 4,299,227 A | 11/1981 | Lincoff |
| 4,366,582 A | 1/1983 | Faulkner |
| 4,402,681 A | 9/1983 | Haas et al. |
| 4,428,746 A | 1/1984 | Mendez |
| 4,449,529 A | 5/1984 | Burns et al. |
| 4,449,974 A | 5/1984 | Messingschlager |
| 4,457,757 A | 7/1984 | Molteno |
| 4,501,274 A | 2/1985 | Skjaerpe |
| 4,521,210 A | 6/1985 | Wong |
| 4,554,918 A | 11/1985 | White |
| 4,560,383 A | 12/1985 | Leiske |
| 4,578,058 A | 3/1986 | Grandon |
| 4,583,224 A | 4/1986 | Ishii et al. |
| 4,604,087 A | 8/1986 | Joseph |
| 4,632,842 A | 12/1986 | Karwoski et al. |
| 4,634,418 A | 1/1987 | Binder |
| 4,642,090 A | 2/1987 | Ultrata |
| 4,692,142 A | 9/1987 | Dignam et al. |
| 4,718,907 A | 1/1988 | Karwoski et al. |
| 4,722,724 A | 2/1988 | Schocket |
| 4,733,665 A | 3/1988 | Palmaz |
| 4,750,901 A | 6/1988 | Molteno |
| 4,787,885 A | 11/1988 | Binder |
| 4,800,870 A | 1/1989 | Reid, Jr. |
| 4,800,890 A | 1/1989 | Cramer |
| 4,804,382 A | 2/1989 | Turina et al. |
| 4,820,626 A | 4/1989 | Williams et al. |
| 4,826,478 A | 5/1989 | Schocket |
| 4,846,172 A | 7/1989 | Berlin |
| 4,846,793 A | 7/1989 | Leonard et al. |
| 4,853,224 A | 8/1989 | Wong |
| 4,863,457 A | 9/1989 | Lee |
| 4,867,173 A | 9/1989 | Leoni |
| 4,870,953 A | 10/1989 | DonMicheal et al. |
| 4,883,864 A | 11/1989 | Scholz |
| 4,886,488 A | 12/1989 | White |
| 4,900,300 A | 2/1990 | Lee |
| 4,905,667 A | 3/1990 | Foerster et al. |
| 4,936,825 A | 6/1990 | Ungerleider |
| 4,946,436 A | 8/1990 | Smith |
| 4,968,296 A | 11/1990 | Ritch et al. |
| 4,986,810 A | 1/1991 | Semrad |
| 4,991,602 A | 2/1991 | Amplatz et al. |
| 4,997,652 A | 3/1991 | Wong |
| 5,005,577 A | 4/1991 | Frenekl |
| 5,041,081 A | 8/1991 | Odrich |
| 5,053,040 A | 10/1991 | Goldsmith, III |
| 5,053,044 A | 10/1991 | Mueller et al. |
| 5,073,163 A | 12/1991 | Lippman |
| 5,092,837 A | 3/1992 | Ritch et al. |
| 5,095,887 A | 3/1992 | Leon et al. |
| 5,116,327 A | 5/1992 | Seder et al. |
| 5,127,901 A | 7/1992 | Odrich |
| 5,129,895 A | 7/1992 | Vassiliadis et al. |
| 5,139,502 A | 8/1992 | Berg et al. |
| 5,164,188 A | 11/1992 | Wong |
| 5,169,386 A | 12/1992 | Becker et al. |
| 5,171,213 A | 12/1992 | Price, Jr. |
| 5,178,604 A | 1/1993 | Baerveldt et al. |
| 5,180,362 A | 1/1993 | Worst |
| 5,207,685 A | 5/1993 | Cinberg et al. |
| 5,221,255 A | 6/1993 | Mahurkar et al. |
| 5,246,451 A | 9/1993 | Trescony et al. |
| 5,248,231 A | 9/1993 | Denham et al. |
| 5,284,476 A | 2/1994 | Kock |
| 5,290,295 A | 3/1994 | Querals et al. |
| 5,300,020 A | 4/1994 | L'Esperance, Jr. |
| 5,318,513 A | 6/1994 | Leib et al. |
| 5,324,306 A | 6/1994 | Makower et al. |
| 5,334,137 A | 8/1994 | Freeman |
| 5,338,291 A | 8/1994 | Speckman et al. |
| 5,342,370 A | 8/1994 | Simon et al. |
| 5,346,464 A | 9/1994 | Camras |
| 5,358,492 A | 10/1994 | Feibus |
| 5,360,399 A | 11/1994 | Stegmann |
| 5,364,374 A | 11/1994 | Morrison et al. |
| 5,370,607 A | 12/1994 | Memmen |
| 5,370,641 A | 12/1994 | O'Donnell, Jr. |
| 5,372,577 A | 12/1994 | Ungerleider |
| 5,397,300 A | 3/1995 | Baerveldt et al. |
| 5,409,457 A | 4/1995 | del Cerro et al. |
| 5,415,666 A | 5/1995 | Gourlay et al. |
| 5,433,701 A | 7/1995 | Rubinstein |
| 5,443,505 A | 8/1995 | Wong et al. |
| 5,445,637 A | 8/1995 | Bretton |
| 5,454,796 A | 10/1995 | Krupin |
| 5,462,558 A | 10/1995 | Kolesa et al. |
| 5,472,440 A | 12/1995 | Beckman |
| 5,476,445 A | 12/1995 | Baerveldt et al. |
| 5,486,165 A | 1/1996 | Stegmann |
| 5,502,052 A | 3/1996 | DeSantis |
| 5,516,522 A | 5/1996 | Peyman et al. |
| 5,520,631 A | 5/1996 | Nordquist et al. |
| 5,547,993 A | 8/1996 | Miki |
| 5,556,400 A | 9/1996 | Tunis |
| 5,557,453 A | 9/1996 | Schalz et al. |
| 5,558,629 A | 9/1996 | Baerveldt et al. |
| 5,558,630 A | 9/1996 | Fisher |
| 5,558,637 A | 9/1996 | Allonen et al. |
| 5,562,641 A | 10/1996 | Flomenblit et al. |
| RE35,390 E | 12/1996 | Smith |
| 5,601,094 A | 2/1997 | Reiss |
| 5,601,549 A | 2/1997 | Miyagi |
| 5,626,558 A | 5/1997 | Suson |
| 5,626,559 A | 5/1997 | Solomon |
| 5,626,588 A | 5/1997 | Sauer et al. |
| 5,639,278 A | 6/1997 | Dereume et al. |
| 5,643,321 A | 7/1997 | McDevitt |
| 5,651,782 A | 7/1997 | Simon et al. |
| 5,651,783 A | 7/1997 | Reynard |
| 5,652,236 A | 7/1997 | Krauss |
| 5,653,724 A | 8/1997 | Imonti |
| 5,663,205 A | 9/1997 | Ogawa et al. |
| 5,665,114 A | 9/1997 | Weadock et al. |
| 5,669,501 A | 9/1997 | Hissong et al. |
| 5,670,161 A | 9/1997 | Healy et al. |
| 5,676,679 A | 10/1997 | Simon et al. |
| 5,681,275 A | 10/1997 | Ahmed |
| 5,681,323 A | 10/1997 | Arick |
| 5,695,479 A | 12/1997 | Jagpal |

(56) References Cited

U.S. PATENT DOCUMENTS

| | | |
|---|---|---|
| 5,702,414 A | 12/1997 | Richter et al. |
| 5,702,419 A | 12/1997 | Berry et al. |
| 5,704,907 A | 1/1998 | Nordquist et al. |
| 5,713,844 A | 2/1998 | Peyman |
| 5,723,005 A | 3/1998 | Herrick |
| 5,725,529 A | 3/1998 | Nicholson et al. |
| 5,725,546 A | 3/1998 | Samson |
| 5,733,256 A | 3/1998 | Costin |
| 5,741,292 A | 4/1998 | Mendius |
| 5,741,333 A | 4/1998 | Frid |
| 5,743,868 A | 4/1998 | Brown et al. |
| 5,752,928 A | 5/1998 | de Roulhac et al. |
| 5,762,625 A | 6/1998 | Igaki |
| 5,766,242 A | 6/1998 | Wong et al. |
| 5,766,243 A | 6/1998 | Christensen et al. |
| 5,767,079 A | 6/1998 | Glaser et al. |
| 5,784,147 A | 7/1998 | Volk |
| 5,785,674 A | 7/1998 | Mateen |
| 5,792,099 A | 8/1998 | DeCamp et al. |
| 5,800,376 A | 9/1998 | Vaskelis |
| 5,807,244 A | 9/1998 | Barot |
| 5,807,302 A | 9/1998 | Wandel |
| 5,810,870 A | 9/1998 | Myers et al. |
| 5,814,620 A | 9/1998 | Robinson et al. |
| 5,817,100 A | 10/1998 | Igaki |
| 5,824,071 A | 10/1998 | Nelson et al. |
| 5,824,072 A | 10/1998 | Wong |
| 5,830,139 A | 11/1998 | Abreu |
| 5,830,171 A | 11/1998 | Wallace |
| 5,833,694 A | 11/1998 | Poncet |
| 5,836,939 A | 11/1998 | Negus et al. |
| 5,840,041 A | 11/1998 | Petter et al. |
| 5,865,831 A | 2/1999 | Cozean et al. |
| 5,868,697 A | 2/1999 | Richter et al. |
| 5,869,468 A | 2/1999 | Freeman |
| 5,879,319 A | 3/1999 | Pynson et al. |
| 5,882,327 A | 3/1999 | Jacob |
| 5,886,822 A | 3/1999 | Spitzer |
| 5,891,084 A | 4/1999 | Lee |
| 5,893,837 A | 4/1999 | Eagles et al. |
| 5,908,449 A | 6/1999 | Bruchman et al. |
| 5,913,852 A | 6/1999 | Magram |
| 5,925,342 A | 7/1999 | Adorante et al. |
| 5,932,299 A | 8/1999 | Katoot |
| 5,941,250 A | 8/1999 | Aramant et al. |
| 5,952,378 A | 9/1999 | Stjerschantz et al. |
| 5,968,058 A | 10/1999 | Richter et al. |
| 5,980,928 A | 11/1999 | Terry |
| 5,981,598 A | 11/1999 | Tatton |
| 5,984,913 A | 11/1999 | Kritzinger et al. |
| 6,004,302 A | 12/1999 | Brierley |
| 6,007,510 A | 12/1999 | Nigam |
| 6,007,511 A | 12/1999 | Prywes |
| 6,030,416 A | 2/2000 | Huo et al. |
| 6,033,434 A | 3/2000 | Borghi |
| 6,036,678 A | 3/2000 | Giungo |
| 6,036,682 A | 3/2000 | Lange et al. |
| 6,045,557 A | 4/2000 | White et al. |
| 6,050,970 A | 4/2000 | Baerveldt |
| 6,050,999 A | 4/2000 | Paraschac et al. |
| 6,059,772 A | 5/2000 | Hsia et al. |
| 6,059,812 A | 5/2000 | Clerc et al. |
| 6,060,463 A | 5/2000 | Freeman |
| 6,063,116 A | 5/2000 | Kelleher |
| 6,063,396 A | 5/2000 | Kelleher |
| 6,071,286 A | 6/2000 | Mawad |
| 6,077,299 A | 6/2000 | Adelberg et al. |
| 6,102,045 A | 8/2000 | Nordquist et al. |
| 6,110,912 A | 8/2000 | Kaufman et al. |
| 6,123,668 A | 9/2000 | Abreu |
| 6,135,977 A | 10/2000 | Drasler et al. |
| 6,142,990 A | 11/2000 | Burk |
| 6,146,387 A | 11/2000 | Trott et al. |
| 6,159,458 A | 12/2000 | Bowman et al. |
| 6,165,210 A | 12/2000 | Lau et al. |
| 6,168,575 B1 | 1/2001 | Soltanpour |
| 6,174,305 B1 | 1/2001 | Mikus et al. |
| 6,177,427 B1 | 1/2001 | Clark et al. |
| 6,184,250 B1 | 2/2001 | Klimko et al. |
| 6,186,974 B1 | 2/2001 | Allan et al. |
| 6,187,016 B1 | 2/2001 | Hedges et al. |
| 6,193,656 B1 | 2/2001 | Jeffries et al. |
| 6,194,415 B1 | 2/2001 | Wheeler et al. |
| 6,197,056 B1 | 3/2001 | Schachar |
| 6,201,001 B1 | 3/2001 | Wang et al. |
| 6,203,513 B1 | 3/2001 | Yaron et al. |
| 6,217,895 B1 | 4/2001 | Guo et al. |
| 6,221,078 B1 | 4/2001 | Bylsma |
| 6,224,570 B1 | 5/2001 | Le et al. |
| 6,228,873 B1 | 5/2001 | Brandt et al. |
| 6,231,597 B1 | 5/2001 | Deem et al. |
| 6,231,853 B1 | 5/2001 | Hillman et al. |
| 6,241,721 B1 | 6/2001 | Cozean et al. |
| 6,251,090 B1 | 6/2001 | Avery et al. |
| 6,254,612 B1 | 7/2001 | Hieshima |
| 6,261,256 B1 | 7/2001 | Ahmed |
| 6,264,668 B1 | 7/2001 | Prywes |
| 6,266,182 B1 | 7/2001 | Morita |
| 6,268,398 B1 | 7/2001 | Ghosh et al. |
| 6,274,138 B1 | 8/2001 | Bandman et al. |
| 6,287,256 B1 | 9/2001 | Park et al. |
| 6,287,313 B1 | 9/2001 | Sasso |
| 6,299,603 B1 | 10/2001 | Hecker et al. |
| 6,299,895 B1 | 10/2001 | Hammang et al. |
| 6,306,114 B1 | 10/2001 | Freeman et al. |
| 6,331,313 B1 | 12/2001 | Wong et al. |
| 6,342,058 B1 | 1/2002 | Portney |
| 6,348,042 B1 | 2/2002 | Warren, Jr. |
| 6,355,033 B1 | 3/2002 | Moorman et al. |
| 6,358,222 B1 | 3/2002 | Grundei |
| 6,361,519 B1 | 3/2002 | Knudson et al. |
| 6,375,642 B1 | 4/2002 | Grieshaber et al. |
| 6,399,734 B1 | 6/2002 | Hodd et al. |
| 6,402,734 B1 | 6/2002 | Weiss |
| 6,405,732 B1 | 6/2002 | Edwards et al. |
| 6,413,540 B1 | 7/2002 | Yaacobi |
| 6,416,777 B1 | 7/2002 | Yaacobi |
| 6,428,501 B1 | 8/2002 | Reynard |
| 6,428,566 B1 | 8/2002 | Holt |
| 6,436,427 B1 | 8/2002 | Hammang et al. |
| 6,450,937 B1 | 9/2002 | Mercereau et al. |
| 6,450,984 B1 | 9/2002 | Lynch et al. |
| 6,454,787 B1 | 9/2002 | Maddalo et al. |
| 6,464,724 B1 | 10/2002 | Lynch et al. |
| 6,468,283 B1 | 10/2002 | Richter et al. |
| 6,494,857 B1 | 12/2002 | Neuhann |
| 6,508,779 B1 | 1/2003 | Suson |
| 6,510,600 B2 | 1/2003 | Yaron et al. |
| 6,517,483 B2 | 2/2003 | Park et al. |
| 6,524,275 B1 | 2/2003 | Lynch et al. |
| 6,530,896 B1 | 3/2003 | Elliott |
| 6,533,768 B1 | 3/2003 | Hill |
| 6,544,249 B1 | 4/2003 | Yu et al. |
| 6,548,078 B2 | 4/2003 | Guo et al. |
| 6,558,342 B1 | 5/2003 | Yaron et al. |
| 6,561,974 B1 | 5/2003 | Grieshaber et al. |
| 6,579,235 B1 | 6/2003 | Abita et al. |
| 6,579,256 B2 | 6/2003 | Hughes |
| 6,582,426 B2 | 6/2003 | Moorman et al. |
| 6,582,453 B1 | 6/2003 | Tran et al. |
| 6,585,680 B2 | 7/2003 | Bugge |
| 6,585,753 B2 | 7/2003 | Eder et al. |
| 6,589,198 B1 | 7/2003 | Soltanpour et al. |
| 6,589,203 B1 | 7/2003 | Mitrev |
| 6,595,945 B2 | 7/2003 | Brown |
| 6,605,053 B1 | 8/2003 | Kamm et al. |
| 6,607,542 B1 | 8/2003 | Wild |
| 6,613,343 B2 | 9/2003 | Dillingham et al. |
| 6,620,154 B1 | 9/2003 | Amirkhanian et al. |
| 6,622,473 B2 | 9/2003 | Lynch et al. |
| 6,626,858 B2 | 9/2003 | Lynch et al. |
| 6,629,981 B2 | 10/2003 | Bui et al. |
| 6,638,239 B1 | 10/2003 | Bergheim et al. |
| 6,666,213 B2 | 12/2003 | Svadovskiy |

(56) References Cited

U.S. PATENT DOCUMENTS

| | | | |
|---|---|---|---|
| 6,666,841 B2 | 12/2003 | Gharib et al. | |
| 6,676,607 B2 | 1/2004 | De Juan, Jr. et al. | |
| 6,682,500 B2 | 1/2004 | Soltanpour et al. | |
| 6,699,211 B2 | 3/2004 | Savage | |
| 6,699,272 B2 | 3/2004 | Slepian et al. | |
| 6,726,676 B2 | 4/2004 | Stegmann et al. | |
| D490,152 S | 5/2004 | Myall et al. | |
| 6,730,056 B1 | 5/2004 | Ghaem et al. | |
| 6,736,791 B1 | 5/2004 | Tu et al. | |
| 6,763,833 B1 | 7/2004 | Khera et al. | |
| 6,764,439 B2 | 7/2004 | Schaaf et al. | |
| 6,767,346 B2 | 7/2004 | Damasco et al. | |
| 6,780,164 B2 | 8/2004 | Bergheim et al. | |
| 6,780,165 B2 | 8/2004 | Kadziauskas et al. | |
| 6,783,544 B2 | 8/2004 | Lynch et al. | |
| 6,827,699 B2 | 12/2004 | Lynch et al. | |
| 6,827,700 B2 | 12/2004 | Lynch et al. | |
| 6,827,738 B2 | 12/2004 | Willis et al. | |
| 6,893,413 B2 | 5/2005 | Martin | |
| 6,902,577 B2 | 6/2005 | Lipshitz et al. | |
| 6,955,656 B2 | 10/2005 | Bergheim et al. | |
| 6,962,573 B1 | 11/2005 | Wilcox | |
| 6,966,888 B2 | 11/2005 | Cullen et al. | |
| 6,981,958 B1 | 1/2006 | Gharib et al. | |
| 7,033,603 B2 | 4/2006 | Nelson et al. | |
| 7,041,077 B2 | 5/2006 | Shields | |
| 7,077,821 B2 | 7/2006 | Durgin | |
| 7,090,681 B2 | 8/2006 | Weber et al. | |
| 7,094,225 B2 | 8/2006 | Tu et al. | |
| 7,101,402 B2 | 9/2006 | Phelps et al. | |
| 7,135,009 B2 | 11/2006 | Tu et al. | |
| 7,135,016 B1 | 11/2006 | Asia et al. | |
| 7,144,616 B1 | 12/2006 | Unger et al. | |
| 7,163,543 B2 | 1/2007 | Smedley et al. | |
| 7,186,232 B1 | 3/2007 | Smedley et al. | |
| 7,192,412 B1 | 3/2007 | Zhou et al. | |
| 7,192,484 B2 | 3/2007 | Chappa et al. | |
| 7,217,263 B2 | 5/2007 | Humayun et al. | |
| 7,220,238 B2 | 5/2007 | Lynch et al. | |
| 7,273,475 B2 | 9/2007 | Tu et al. | |
| 7,291,125 B2* | 11/2007 | Coroneo | 604/9 |
| 7,294,115 B1 | 11/2007 | Wilk | |
| 7,297,130 B2 | 11/2007 | Bergheim et al. | |
| 7,331,984 B2 | 2/2008 | Tu et al. | |
| 7,344,528 B1 | 3/2008 | Tu et al. | |
| 7,364,564 B2 | 4/2008 | Sniegowski et al. | |
| 7,431,710 B2 | 10/2008 | Tu et al. | |
| 7,488,303 B1 | 2/2009 | Haffner et al. | |
| 7,520,876 B2 | 4/2009 | Ressemann et al. | |
| RE40,722 E | 6/2009 | Chappa | |
| 7,563,241 B2* | 7/2009 | Tu et al. | 604/8 |
| 7,592,016 B2 | 9/2009 | Wong et al. | |
| 7,641,627 B2 | 1/2010 | Camras et al. | |
| 7,662,123 B2 | 2/2010 | Shields | |
| 7,678,065 B2 | 3/2010 | Haffner et al. | |
| 7,695,135 B1 | 4/2010 | Rosenthal | |
| 7,708,711 B2 | 5/2010 | Tu et al. | |
| 7,758,624 B2 | 7/2010 | Dorn et al. | |
| 7,771,388 B2 | 8/2010 | Olsen et al. | |
| 7,811,268 B2 | 10/2010 | Maldon Ado Bas | |
| 7,815,592 B2 | 10/2010 | Coroneo | |
| 7,850,637 B2 | 12/2010 | Lynch et al. | |
| 7,850,638 B2 | 12/2010 | Coroneo | |
| 7,857,782 B2* | 12/2010 | Tu et al. | 604/8 |
| 7,862,531 B2 | 1/2011 | Yaron et al. | |
| 7,867,186 B2 | 1/2011 | Haffner et al. | |
| 7,867,205 B2 | 1/2011 | Bergheim et al. | |
| 7,879,001 B2 | 2/2011 | Haffner et al. | |
| 7,879,079 B2 | 2/2011 | Tu et al. | |
| 7,905,904 B2 | 3/2011 | Stone et al. | |
| 7,931,660 B2 | 4/2011 | Aranyi et al. | |
| 7,945,336 B2 | 5/2011 | Sauter-Starace et al. | |
| 7,951,155 B2 | 5/2011 | Smedley et al. | |
| 7,959,632 B2 | 6/2011 | Fugo | |
| 7,967,772 B2 | 6/2011 | McKenzie et al. | |
| 7,997,460 B2 | 8/2011 | Pardes et al. | |
| 8,007,459 B2 | 8/2011 | Haffner et al. | |
| 8,034,016 B2 | 10/2011 | Yaron et al. | |
| 8,034,105 B2 | 10/2011 | Stegmann et al. | |
| 8,062,244 B2* | 11/2011 | Tu et al. | 604/8 |
| 8,075,511 B2* | 12/2011 | Tu et al. | 604/8 |
| 8,118,768 B2 | 2/2012 | Tu et al. | |
| 8,128,588 B2* | 3/2012 | Coroneo | 604/8 |
| 8,142,364 B2 | 3/2012 | Haffner et al. | |
| 8,152,752 B2 | 4/2012 | Lynch et al. | |
| 8,197,418 B2 | 6/2012 | Lal et al. | |
| 8,267,882 B2 | 9/2012 | Euteneuer et al. | |
| 8,267,995 B2 | 9/2012 | Castillejos | |
| 8,273,050 B2 | 9/2012 | Bergheim et al. | |
| 8,313,454 B2 | 11/2012 | Yaron et al. | |
| 8,333,742 B2 | 12/2012 | Bergheim et al. | |
| 8,337,445 B2 | 12/2012 | Tu et al. | |
| 8,337,509 B2 | 12/2012 | Schieber et al. | |
| 8,388,568 B2 | 3/2013 | Lynch et al. | |
| 8,439,972 B2 | 5/2013 | Badawi et al. | |
| 8,444,588 B2 | 5/2013 | Yablonski | |
| 8,444,589 B2 | 5/2013 | Silvestrini | |
| 8,506,515 B2 | 8/2013 | Burns et al. | |
| 8,540,659 B2 | 9/2013 | Berlin | |
| 8,579,846 B2 | 11/2013 | Tu et al. | |
| 8,617,094 B2 | 12/2013 | Smedley et al. | |
| 8,656,958 B2 | 2/2014 | Unger et al. | |
| 8,657,776 B2 | 2/2014 | Wardle et al. | |
| 8,679,089 B2 | 3/2014 | Berlin | |
| 8,771,217 B2 | 7/2014 | Lynch et al. | |
| 8,801,648 B2 | 8/2014 | Bergheim et al. | |
| 8,808,219 B2 | 8/2014 | Bergheim et al. | |
| 8,808,220 B2 | 8/2014 | Coroneo | |
| 8,814,820 B2 | 8/2014 | Bergheim et al. | |
| 8,852,137 B2 | 10/2014 | Horvath et al. | |
| 8,852,266 B2 | 10/2014 | Brooks et al. | |
| 8,882,781 B2 | 11/2014 | Smedley et al. | |
| 9,155,654 B2 | 10/2015 | Tu et al. | |
| 9,173,775 B2 | 11/2015 | Haffner et al. | |
| 9,220,632 B2 | 12/2015 | Smedley et al. | |
| 2001/0025150 A1 | 9/2001 | de Juan et al. | |
| 2002/0013546 A1 | 1/2002 | Grieshaber et al. | |
| 2002/0013572 A1 | 1/2002 | Berlin | |
| 2002/0026200 A1 | 2/2002 | Savage | |
| 2002/0072673 A1 | 6/2002 | Yamamoto et al. | |
| 2002/0082591 A1 | 6/2002 | Haefliger | |
| 2002/0087111 A1 | 7/2002 | Ethier et al. | |
| 2002/0099434 A1 | 7/2002 | Buscemi et al. | |
| 2002/0111608 A1 | 8/2002 | Baerveldt et al. | |
| 2002/0120284 A1 | 8/2002 | Schachar et al. | |
| 2002/0120285 A1 | 8/2002 | Schachar et al. | |
| 2002/0133168 A1 | 9/2002 | Smedley et al. | |
| 2002/0143284 A1 | 10/2002 | Tu et al. | |
| 2002/0156413 A1 | 10/2002 | Williams et al. | |
| 2002/0165522 A1 | 11/2002 | Holmen | |
| 2002/0177856 A1 | 11/2002 | Richter et al. | |
| 2002/0188308 A1 | 12/2002 | Tu et al. | |
| 2002/0193725 A1 | 12/2002 | Odrich | |
| 2003/0014021 A1 | 1/2003 | Holmen | |
| 2003/0014092 A1 | 1/2003 | Neuhann | |
| 2003/0019833 A1 | 1/2003 | Unger et al. | |
| 2003/0055372 A1 | 3/2003 | Lynch et al. | |
| 2003/0060752 A1 | 3/2003 | Bergheim et al. | |
| 2003/0069637 A1 | 4/2003 | Lynch et al. | |
| 2003/0079329 A1 | 5/2003 | Yaron et al. | |
| 2003/0088260 A1 | 5/2003 | Smedley et al. | |
| 2003/0093084 A1 | 5/2003 | Nissan et al. | |
| 2003/0097117 A1 | 5/2003 | Buono | |
| 2003/0097151 A1 | 5/2003 | Smedley et al. | |
| 2003/0105456 A1 | 6/2003 | Lin | |
| 2003/0109907 A1 | 6/2003 | Shadduck | |
| 2003/0135149 A1 | 7/2003 | Cullen et al. | |
| 2003/0153863 A1 | 8/2003 | Patel | |
| 2003/0181848 A1 | 9/2003 | Bergheim et al. | |
| 2003/0187384 A1 | 10/2003 | Bergheim et al. | |
| 2003/0187385 A1 | 10/2003 | Bergheim et al. | |
| 2003/0195438 A1 | 10/2003 | Petillo | |
| 2003/0208163 A1 | 11/2003 | Yaron et al. | |
| 2003/0208217 A1 | 11/2003 | Dan | |

(56) References Cited

U.S. PATENT DOCUMENTS

| | | |
|---|---|---|
| 2003/0212383 A1 | 11/2003 | Cote et al. |
| 2003/0229303 A1 | 12/2003 | Haffner et al. |
| 2003/0236483 A1 | 12/2003 | Ren |
| 2003/0236484 A1 | 12/2003 | Lynch et al. |
| 2004/0024345 A1 | 2/2004 | Gharib et al. |
| 2004/0050392 A1 | 3/2004 | Tu et al. |
| 2004/0059248 A1 | 3/2004 | Messner et al. |
| 2004/0076676 A1 | 4/2004 | Tojo et al. |
| 2004/0088048 A1 | 5/2004 | Richter et al. |
| 2004/0092856 A1 | 5/2004 | Dahan |
| 2004/0098122 A1 | 5/2004 | Lee et al. |
| 2004/0102729 A1 | 5/2004 | Haffner et al. |
| 2004/0111050 A1 | 6/2004 | Smedley et al. |
| 2004/0127843 A1 | 7/2004 | Tu et al. |
| 2004/0147870 A1 | 7/2004 | Burns et al. |
| 2004/0154946 A1 | 8/2004 | Solovay et al. |
| 2004/0162545 A1 | 8/2004 | Brown et al. |
| 2004/0193095 A1 | 9/2004 | Shadduck |
| 2004/0193262 A1 | 9/2004 | Shadduck |
| 2004/0210181 A1 | 10/2004 | Vass et al. |
| 2004/0210185 A1 | 10/2004 | Tu et al. |
| 2004/0215126 A1 | 10/2004 | Ahmed |
| 2004/0225250 A1 | 11/2004 | Yablonski |
| 2004/0236343 A1 | 11/2004 | Taylor et al. |
| 2004/0243227 A1 | 12/2004 | Starksen et al. |
| 2004/0249404 A1 | 12/2004 | Haefliger |
| 2004/0254517 A1 | 12/2004 | Quiroz-Mercado et al. |
| 2004/0254520 A1 | 12/2004 | Porteous et al. |
| 2004/0254521 A1 | 12/2004 | Simon |
| 2004/0260227 A1 | 12/2004 | Lisk, Jr. et al. |
| 2005/0038334 A1 | 2/2005 | Lynch et al. |
| 2005/0038498 A1 | 2/2005 | Dubrow et al. |
| 2005/0049578 A1 | 3/2005 | Tu et al. |
| 2005/0055075 A1 | 3/2005 | Pinchuk et al. |
| 2005/0096639 A1 | 5/2005 | Slatkine et al. |
| 2005/0107734 A1 | 5/2005 | Coroneo |
| 2005/0119601 A9 | 6/2005 | Lynch et al. |
| 2005/0119737 A1 | 6/2005 | Bene et al. |
| 2005/0125003 A1 | 6/2005 | Pinchuk et al. |
| 2005/0165385 A1 | 7/2005 | Simon |
| 2005/0171562 A1 | 8/2005 | Criscuolo et al. |
| 2005/0182350 A1 | 8/2005 | Nigam |
| 2005/0184004 A1 | 8/2005 | Rodgers et al. |
| 2005/0192527 A1 | 9/2005 | Gharib et al. |
| 2005/0209672 A1 | 9/2005 | George et al. |
| 2005/0240143 A1 | 10/2005 | Dohlman |
| 2005/0250788 A1 | 11/2005 | Tu et al. |
| 2005/0261624 A1 | 11/2005 | Wilcox |
| 2005/0267397 A1 | 12/2005 | Bhalla |
| 2005/0267398 A1 | 12/2005 | Protopsaltis et al. |
| 2005/0267478 A1 | 12/2005 | Corradi et al. |
| 2005/0271704 A1 | 12/2005 | Tu et al. |
| 2005/0273033 A1 | 12/2005 | Grahn et al. |
| 2005/0277864 A1 | 12/2005 | Haffner et al. |
| 2005/0283108 A1 | 12/2005 | Savage |
| 2006/0032507 A1 | 2/2006 | Tu |
| 2006/0036207 A1 | 2/2006 | Koonmen et al. |
| 2006/0069340 A1 | 3/2006 | Simon |
| 2006/0079828 A1 | 4/2006 | Brown |
| 2006/0106370 A1 | 5/2006 | Baerveldt et al. |
| 2006/0116626 A1 | 6/2006 | Smedley et al. |
| 2006/0129129 A1 | 6/2006 | Smith |
| 2006/0155238 A1 | 7/2006 | Shields |
| 2006/0155300 A1 | 7/2006 | Stamper et al. |
| 2006/0173397 A1 | 8/2006 | Tu et al. |
| 2006/0200113 A1 | 9/2006 | Haffner et al. |
| 2006/0210605 A1 | 9/2006 | Chang et al. |
| 2006/0217741 A1 | 9/2006 | Ghannoum |
| 2006/0235367 A1 | 10/2006 | Takashima et al. |
| 2006/0241580 A1 | 10/2006 | Mittelstein et al. |
| 2006/0276739 A1 | 12/2006 | Brown |
| 2007/0004998 A1 | 1/2007 | Rodgers et al. |
| 2007/0021653 A1 | 1/2007 | Hattenbach et al. |
| 2007/0073275 A1 | 3/2007 | Conston et al. |
| 2007/0073390 A1 | 3/2007 | Lee |
| 2007/0078371 A1 | 4/2007 | Brown et al. |
| 2007/0078471 A1 | 4/2007 | Schachar et al. |
| 2007/0088242 A1 | 4/2007 | Coroneo |
| 2007/0093740 A1 | 4/2007 | Shetty |
| 2007/0106199 A1 | 5/2007 | Krivoy et al. |
| 2007/0106200 A1 | 5/2007 | Levy |
| 2007/0106235 A1 | 5/2007 | Coroneo |
| 2007/0112292 A1 | 5/2007 | Tu et al. |
| 2007/0118065 A1 | 5/2007 | Pinchuk et al. |
| 2007/0118066 A1 | 5/2007 | Pinchuk et al. |
| 2007/0123812 A1 | 5/2007 | Pinchuk et al. |
| 2007/0123919 A1 | 5/2007 | Schachar et al. |
| 2007/0149915 A1 | 6/2007 | Yablonski |
| 2007/0149927 A1 | 6/2007 | Itou et al. |
| 2007/0154621 A1 | 7/2007 | Raad |
| 2007/0156079 A1 | 7/2007 | Brown |
| 2007/0161981 A1 | 7/2007 | Sanders et al. |
| 2007/0179426 A1 | 8/2007 | Selden |
| 2007/0179471 A1 | 8/2007 | Christian et al. |
| 2007/0185468 A1 | 8/2007 | Prywes |
| 2007/0191863 A1 | 8/2007 | De Juan et al. |
| 2007/0202186 A1 | 8/2007 | Yamamoto et al. |
| 2007/0207186 A1 | 9/2007 | Scanlon et al. |
| 2007/0212386 A1 | 9/2007 | Patravale et al. |
| 2007/0212387 A1 | 9/2007 | Patravale et al. |
| 2007/0212388 A1 | 9/2007 | Patravale et al. |
| 2007/0212393 A1 | 9/2007 | Patravale et al. |
| 2007/0219632 A1 | 9/2007 | Castillejos |
| 2007/0233037 A1 | 10/2007 | Gifford, III et al. |
| 2007/0260201 A1 | 11/2007 | Prausnitz et al. |
| 2007/0276315 A1 | 11/2007 | Haffner |
| 2007/0276316 A1 | 11/2007 | Haffner |
| 2007/0282245 A1 | 12/2007 | Tu et al. |
| 2007/0287958 A1 | 12/2007 | McKenzie et al. |
| 2007/0292470 A1 | 12/2007 | Thornton |
| 2007/0292474 A1 | 12/2007 | Hsu et al. |
| 2007/0293807 A1 | 12/2007 | Lynch et al. |
| 2007/0293872 A1 | 12/2007 | Peyman |
| 2007/0293873 A1 | 12/2007 | Chang |
| 2007/0298068 A1 | 12/2007 | Badawi et al. |
| 2008/0027304 A1 | 1/2008 | Pardo et al. |
| 2008/0033351 A1 | 2/2008 | Trogden et al. |
| 2008/0039931 A1 | 2/2008 | Jelle et al. |
| 2008/0051681 A1 | 2/2008 | Schwartz |
| 2008/0058704 A1 | 3/2008 | Hee et al. |
| 2008/0082078 A1 | 4/2008 | Berlin |
| 2008/0091224 A1 | 4/2008 | Griffis, III et al. |
| 2008/0097214 A1 | 4/2008 | Meyers et al. |
| 2008/0097335 A1 | 4/2008 | Trogden et al. |
| 2008/0108932 A1 | 5/2008 | Rodgers |
| 2008/0108933 A1 | 5/2008 | Yu et al. |
| 2008/0108934 A1 | 5/2008 | Berlin |
| 2008/0109037 A1 | 5/2008 | Steiner et al. |
| 2008/0114440 A1 | 5/2008 | Hlavka et al. |
| 2008/0125691 A1 | 5/2008 | Yaron et al. |
| 2008/0140059 A1 | 6/2008 | Schachar et al. |
| 2008/0147083 A1 | 6/2008 | Vold et al. |
| 2008/0161741 A1 | 7/2008 | Bene et al. |
| 2008/0161907 A1 | 7/2008 | Chen et al. |
| 2008/0183289 A1 | 7/2008 | Werblin |
| 2008/0188860 A1 | 8/2008 | Vold |
| 2008/0195027 A1 | 8/2008 | Coroneo |
| 2008/0200860 A1 | 8/2008 | Tu et al. |
| 2008/0200923 A1 | 8/2008 | Beckman et al. |
| 2008/0208176 A1 | 8/2008 | Loh |
| 2008/0210322 A1 | 9/2008 | Unger et al. |
| 2008/0215062 A1 | 9/2008 | Bowen et al. |
| 2008/0221501 A1 | 9/2008 | Cote et al. |
| 2008/0228127 A1 | 9/2008 | Burns et al. |
| 2008/0236669 A1 | 10/2008 | Unger et al. |
| 2008/0243156 A1 | 10/2008 | John |
| 2008/0243243 A1 | 10/2008 | Williams et al. |
| 2008/0243247 A1 | 10/2008 | Poley et al. |
| 2008/0255545 A1 | 10/2008 | Mansfield et al. |
| 2008/0269730 A1 | 10/2008 | Dotson |
| 2008/0277007 A1 | 11/2008 | Unger et al. |
| 2008/0281250 A1 | 11/2008 | Bergsneider et al. |
| 2008/0289710 A1 | 11/2008 | Unger et al. |
| 2008/0306429 A1 | 12/2008 | Shields et al. |

(56) References Cited

U.S. PATENT DOCUMENTS

| | | |
|---|---|---|
| 2009/0036818 A1 | 2/2009 | Grahn et al. |
| 2009/0043242 A1 | 2/2009 | Bene et al. |
| 2009/0043321 A1 | 2/2009 | Conston et al. |
| 2009/0043365 A1 | 2/2009 | Friedland et al. |
| 2009/0076436 A2 | 3/2009 | Gharib et al. |
| 2009/0082860 A1 | 3/2009 | Schieber et al. |
| 2009/0082862 A1 | 3/2009 | Schieber et al. |
| 2009/0082863 A1 | 3/2009 | Schieber et al. |
| 2009/0112245 A1 | 4/2009 | Haefliger |
| 2009/0124973 A1 | 5/2009 | D'Agostino et al. |
| 2009/0132040 A1 | 5/2009 | Frion et al. |
| 2009/0137989 A1 | 5/2009 | Kataoka |
| 2009/0137992 A1 | 5/2009 | Mallakrishnan |
| 2009/0151422 A1 | 6/2009 | Unger et al. |
| 2009/0177138 A1 | 7/2009 | Brown et al. |
| 2009/0177245 A1 | 7/2009 | Ameri et al. |
| 2009/0182421 A1 | 7/2009 | Silvestrini et al. |
| 2009/0198213 A1 | 8/2009 | Tanaka |
| 2009/0204053 A1 | 8/2009 | Nissan et al. |
| 2009/0227934 A1 | 9/2009 | Euteneuer et al. |
| 2009/0264813 A1 | 10/2009 | Chang |
| 2009/0275924 A1 | 11/2009 | Lattanzio et al. |
| 2009/0287136 A1 | 11/2009 | Castillejos |
| 2009/0287233 A1 | 11/2009 | Huculak |
| 2009/0326432 A1 | 12/2009 | Schmidt et al. |
| 2010/0004581 A1 | 1/2010 | Brigatti et al. |
| 2010/0004635 A1 | 1/2010 | Lin et al. |
| 2010/0010416 A1 | 1/2010 | Juan, Jr. et al. |
| 2010/0010452 A1 | 1/2010 | Paques |
| 2010/0025613 A1 | 2/2010 | Tai et al. |
| 2010/0030150 A1 | 2/2010 | Paques et al. |
| 2010/0042209 A1 | 2/2010 | Guarnieri |
| 2010/0056977 A1 | 3/2010 | Wandel |
| 2010/0056979 A1 | 3/2010 | Smedley et al. |
| 2010/0057055 A1 | 3/2010 | Camras et al. |
| 2010/0057093 A1 | 3/2010 | Ide et al. |
| 2010/0076419 A1 | 3/2010 | Chew et al. |
| 2010/0106073 A1 | 4/2010 | Haffner et al. |
| 2010/0114006 A1 | 5/2010 | Baerveldt |
| 2010/0121248 A1 | 5/2010 | Yu et al. |
| 2010/0121249 A1 | 5/2010 | Yu et al. |
| 2010/0121342 A1 | 5/2010 | Schieber et al. |
| 2010/0125237 A1 | 5/2010 | Schocket |
| 2010/0137981 A1 | 6/2010 | Silvestrini et al. |
| 2010/0152626 A1 | 6/2010 | Schwartz |
| 2010/0152641 A1 | 6/2010 | Yablonski |
| 2010/0168644 A1 | 7/2010 | Brown |
| 2010/0173866 A1 | 7/2010 | Hee et al. |
| 2010/0175767 A1 | 7/2010 | Unger et al. |
| 2010/0185138 A1 | 7/2010 | Yaron et al. |
| 2010/0185205 A1 | 7/2010 | Novakovic et al. |
| 2010/0191103 A1 | 7/2010 | Stamper et al. |
| 2010/0191329 A1 | 7/2010 | Badawi et al. |
| 2010/0222733 A1 | 9/2010 | Schieber et al. |
| 2010/0234791 A1 | 9/2010 | Lynch et al. |
| 2010/0240987 A1 | 9/2010 | Christian et al. |
| 2010/0241046 A1 | 9/2010 | Pinchuk et al. |
| 2010/0249691 A1 | 9/2010 | Van Der Mooren et al. |
| 2010/0262174 A1 | 10/2010 | Sretavan |
| 2010/0274258 A1 | 10/2010 | Silvestrini et al. |
| 2010/0274259 A1 | 10/2010 | Yaron et al. |
| 2010/0280317 A1 | 11/2010 | Silvestrini et al. |
| 2011/0009874 A1 | 1/2011 | Wardle et al. |
| 2011/0009958 A1 | 1/2011 | Wardle et al. |
| 2011/0022065 A1 | 1/2011 | Shipp |
| 2011/0028883 A1 | 2/2011 | Juan, Jr. et al. |
| 2011/0028884 A1 | 2/2011 | Coroneo |
| 2011/0028983 A1 | 2/2011 | Silvestrini et al. |
| 2011/0046536 A1 | 2/2011 | Stegmann et al. |
| 2011/0046728 A1 | 2/2011 | Shareef et al. |
| 2011/0066098 A1 | 3/2011 | Stergiopulos |
| 2011/0071454 A1 | 3/2011 | Dos Santos et al. |
| 2011/0071456 A1 | 3/2011 | Rickard |
| 2011/0071458 A1 | 3/2011 | Rickard |
| 2011/0071459 A1 | 3/2011 | Rickard et al. |
| 2011/0071505 A1 | 3/2011 | Rickard et al. |
| 2011/0071524 A1 | 3/2011 | Keller |
| 2011/0077626 A1 | 3/2011 | Baerveldt et al. |
| 2011/0082385 A1 | 4/2011 | Diaz et al. |
| 2011/0087151 A1 | 4/2011 | Coroneo |
| 2011/0092878 A1 | 4/2011 | Tu et al. |
| 2011/0092965 A1 | 4/2011 | Slatkine et al. |
| 2011/0098627 A1 | 4/2011 | Wilcox |
| 2011/0098629 A1 | 4/2011 | Juan, Jr. et al. |
| 2011/0098809 A1 | 4/2011 | Wardle et al. |
| 2011/0105987 A1 | 5/2011 | Bergheim et al. |
| 2011/0112546 A1 | 5/2011 | Juan, Jr. et al. |
| 2011/0118649 A1 | 5/2011 | Stegmann et al. |
| 2011/0118835 A1 | 5/2011 | Silvestrini et al. |
| 2011/0130831 A1 | 6/2011 | Badawi et al. |
| 2011/0144559 A1 | 6/2011 | Lafdi et al. |
| 2011/0144641 A1 | 6/2011 | Dimalanta, Jr. et al. |
| 2011/0196487 A1 | 8/2011 | Badawi et al. |
| 2011/0202049 A1 | 8/2011 | Jia et al. |
| 2011/0224597 A1 | 9/2011 | Stegmann et al. |
| 2011/0230877 A1 | 9/2011 | Huculak et al. |
| 2011/0306915 A1 | 12/2011 | De Juan, Jr. et al. |
| 2011/0319793 A1 | 12/2011 | Hynynen |
| 2011/0319806 A1 | 12/2011 | Wardle |
| 2012/0010702 A1 | 1/2012 | Stegmann et al. |
| 2012/0016286 A1 | 1/2012 | Silvestrini et al. |
| 2012/0022409 A1 | 1/2012 | Gertner et al. |
| 2012/0022424 A1 | 1/2012 | Yamamoto et al. |
| 2012/0022429 A1 | 1/2012 | Silvestrini et al. |
| 2012/0035524 A1 | 2/2012 | Silvestrini |
| 2012/0035525 A1 | 2/2012 | Silvestrini |
| 2012/0059461 A1 | 3/2012 | Badawi et al. |
| 2012/0065570 A1 | 3/2012 | Yeung et al. |
| 2012/0071908 A1 | 3/2012 | Sorensen et al. |
| 2012/0078158 A1 | 3/2012 | Haffner et al. |
| 2012/0078281 A1 | 3/2012 | Cox et al. |
| 2012/0089072 A1 | 4/2012 | Cunningham, Jr. |
| 2012/0089073 A1 | 4/2012 | Cunningham, Jr. |
| 2012/0123439 A1 | 5/2012 | Romoda et al. |
| 2012/0123440 A1 | 5/2012 | Horvath et al. |
| 2012/0130467 A1 | 5/2012 | Selden et al. |
| 2012/0165721 A1 | 6/2012 | Grabner et al. |
| 2012/0165722 A1 | 6/2012 | Horvath et al. |
| 2012/0165723 A1 | 6/2012 | Horvath et al. |
| 2012/0179087 A1 | 7/2012 | Schieber et al. |
| 2012/0184892 A1 | 7/2012 | Bigler et al. |
| 2012/0197175 A1 | 8/2012 | Horvath et al. |
| 2012/0203160 A1 | 8/2012 | Kahook et al. |
| 2012/0203262 A1 | 8/2012 | Connors et al. |
| 2012/0220917 A1 | 8/2012 | Silvestrini et al. |
| 2012/0232570 A1 | 9/2012 | Jenson et al. |
| 2012/0271272 A1 | 10/2012 | Hammack et al. |
| 2012/0283557 A1 | 11/2012 | Berlin |
| 2012/0289883 A1 | 11/2012 | Meng et al. |
| 2012/0302861 A1 | 11/2012 | Marshall et al. |
| 2012/0310072 A1 | 12/2012 | Grieshaber |
| 2012/0310137 A1 | 12/2012 | Silvestrini |
| 2012/0323159 A1 | 12/2012 | Wardle et al. |
| 2013/0006164 A1 | 1/2013 | Yaron et al. |
| 2013/0006165 A1 | 1/2013 | Euteneuer et al. |
| 2013/0018295 A1 | 1/2013 | Haffner et al. |
| 2013/0018412 A1 | 1/2013 | Journey et al. |
| 2013/0079701 A1 | 3/2013 | Schieber et al. |
| 2013/0079759 A1 | 3/2013 | Dotson et al. |
| 2013/0090534 A1 | 4/2013 | Burns et al. |
| 2013/0102949 A1 | 4/2013 | Baerveldt |
| 2013/0110125 A1 | 5/2013 | Silvestrini et al. |
| 2013/0131577 A1 | 5/2013 | Bronstein et al. |
| 2013/0144202 A1 | 6/2013 | Field et al. |
| 2013/0150770 A1 | 6/2013 | Horvath et al. |
| 2013/0150773 A1 | 6/2013 | Nissan et al. |
| 2013/0150774 A1 | 6/2013 | Field et al. |
| 2013/0150776 A1 | 6/2013 | Bohm et al. |
| 2013/0150777 A1 | 6/2013 | Bohm et al. |
| 2013/0150779 A1 | 6/2013 | Field |
| 2013/0150959 A1 | 6/2013 | Schieber et al. |
| 2013/0158381 A1 | 6/2013 | Rickard |
| 2013/0158462 A1 | 6/2013 | Wardle et al. |
| 2013/0165840 A1 | 6/2013 | Orge |

(56) References Cited

U.S. PATENT DOCUMENTS

| | | |
|---|---|---|
| 2013/0172804 A1 | 7/2013 | Schieber et al. |
| 2013/0184631 A1 | 7/2013 | Pinchuk |
| 2013/0245532 A1 | 9/2013 | Tu et al. |
| 2013/0253404 A1 | 9/2013 | Tu et al. |
| 2013/0253405 A1 | 9/2013 | Tu |
| 2013/0253528 A1 | 9/2013 | Haffner et al. |
| 2013/0281910 A1 | 10/2013 | Tu et al. |
| 2014/0034607 A1 | 2/2014 | Meng et al. |
| 2014/0046437 A1 | 2/2014 | Renke |
| 2014/0052046 A1 | 2/2014 | Peartree et al. |
| 2014/0081194 A1 | 3/2014 | Burns et al. |
| 2014/0135916 A1 | 5/2014 | Clauson et al. |
| 2014/0155803 A1 | 6/2014 | Silvestrini |
| 2014/0276332 A1 | 9/2014 | Crimaldi et al. |
| 2014/0343475 A1 | 11/2014 | Smedley et al. |
| 2015/0065940 A1 | 3/2015 | Rangel-Friedman et al. |
| 2015/0148730 A1 | 5/2015 | Lynch et al. |
| 2015/0223981 A1 | 8/2015 | Smedley et al. |
| 2015/0374546 A1 | 12/2015 | Hill |
| 2016/0151204 A1 | 6/2016 | Haffner et al. |

FOREIGN PATENT DOCUMENTS

| | | |
|---|---|---|
| AU | 2009251058 B2 | 12/2013 |
| CA | 2273331 | 6/1998 |
| CA | 2244646 A1 | 2/1999 |
| CA | 2311244 | 6/1999 |
| CA | 2643357 | 11/1999 |
| CA | 2683224 C | 12/2014 |
| DE | 19840047 A1 | 3/2000 |
| EP | 0436232 A1 | 7/1991 |
| EP | 0550791 A | 7/1993 |
| EP | 0858788 A1 | 8/1998 |
| EP | 0881055 A1 | 12/1998 |
| EP | 0898947 A2 | 3/1999 |
| EP | 1114627 A1 | 7/2001 |
| EP | 1977724 A1 | 10/2008 |
| EP | 2088976 | 8/2009 |
| EP | 2260803 A2 | 12/2010 |
| EP | 2351589 | 8/2011 |
| FR | 2710269 A1 | 3/1995 |
| FR | 2721499 | 12/1995 |
| FR | 2757068 A1 | 6/1998 |
| GB | 2296663 A | 7/1996 |
| JP | 11-123205 | 5/1999 |
| JP | 3703721 | 7/2005 |
| JP | 4688444 | 2/2011 |
| JP | 5255402 | 4/2013 |
| JP | 5323011 | 7/2013 |
| RU | 2143250 | 12/1999 |
| WO | WO 89/00869 A1 | 2/1989 |
| WO | WO 91/08784 | 6/1991 |
| WO | WO 91/18568 A1 | 12/1991 |
| WO | WO 92/00112 | 1/1992 |
| WO | WO 92/08406 | 5/1992 |
| WO | WO 92/19294 | 11/1992 |
| WO | WO 94/02081 | 2/1994 |
| WO | WO/94/13234 | 6/1994 |
| WO | WO 94/21205 A1 | 9/1994 |
| WO | WO 95/08310 | 3/1995 |
| WO | WO 95/08310 A1 | 3/1995 |
| WO | WO 96/20742 A1 | 7/1996 |
| WO | WO 96/36377 | 11/1996 |
| WO | WO 98/23237 | 6/1998 |
| WO | WO 98/30181 | 7/1998 |
| WO | WO 98/30181 A1 | 7/1998 |
| WO | WO 98/35639 A1 | 8/1998 |
| WO | WO 98/37831 | 9/1998 |
| WO | WO 99/26567 A1 | 6/1999 |
| WO | WO 99/30641 A1 | 6/1999 |
| WO | WO 99/30644 | 6/1999 |
| WO | WO 99/38470 A2 | 8/1999 |
| WO | WO 99/38470 A3 | 8/1999 |
| WO | WO 00/13627 A1 | 3/2000 |
| WO | WO 00/64389 A1 | 11/2000 |
| WO | WO 00/64390 A1 | 11/2000 |
| WO | WO 00/64391 A1 | 11/2000 |
| WO | WO 00/64393 A1 | 11/2000 |
| WO | WO 00/72788 A1 | 12/2000 |
| WO | WO 01/50943 A2 | 7/2001 |
| WO | WO 01/78631 A2 | 10/2001 |
| WO | WO 01/78656 A2 | 10/2001 |
| WO | WO 01/85065 | 11/2001 |
| WO | WO 01/97727 | 12/2001 |
| WO | WO 02/36052 | 5/2002 |
| WO | WO 02/074052 A2 | 9/2002 |
| WO | WO 02/080811 | 10/2002 |
| WO | WO 02/102274 A2 | 12/2002 |
| WO | WO 03/015659 A2 | 2/2003 |
| WO | WO 03/041622 | 5/2003 |
| WO | WO 03/045290 | 6/2003 |
| WO | WO 03/073968 A2 | 9/2003 |
| WO | WO 2005/055873 A2 | 6/2005 |
| WO | WO 2005/107845 | 11/2005 |
| WO | WO 2008/061043 A3 | 5/2008 |
| WO | WO 2009/012406 | 1/2009 |
| WO | WO 2010/093945 A3 | 8/2010 |
| WO | WO 2011/020633 A1 | 2/2011 |
| WO | WO 2012/071476 | 5/2012 |
| WO | WO 2013/148275 | 10/2013 |
| WO | WO 2014/151070 | 9/2014 |

OTHER PUBLICATIONS

Bahler, Cindy K., BS, Gregrory T. Smedley, PhD, Jianbo Zhou, PhD, Douglas H. Johnson, MD., *Trabecular Bypass Stents Decrease Intraocular Pressure in Cultured Human Anterior Segments*, American Journal of Ophthalmology, Dec. 2004, vol. 138, pp. 988-994.

Bietti, G.B., "The Present State of the Use of Plastics in Eye Surgery," Acta Ophthalmologica, vol. 33, No. 4 (1955).

Coote, M. A., "Glaucoma Hollow Fiber Filters—A New Glaucoma Seton. Preliminary Results," J. Glaucoma, vol. 8, No. 1, Supplement (1999).

Cullen et al., "Anterior Chamber to Frontal Sinus Shunt for the Diversion of Aqueous Humor: A Pilot Study in Four Normal Dogs," Veterinary Ophthalmology, vol. 1, No. 1 (1998).

Dorland's Illustrated Medical Dictionary, 28th Edition, Philadelphia: W.B. Saunders Company, 1994, p. 167.

Emi, Kazayuki, et al., Hydrostatic Pressure of the Suprachoroidal Space, Investigative Ophthalmology & Visual Science, vol. 30, No. 2, Feb. 1989 (pp. 233-238).

Extended European Search Report in European Application No. 08102896.1, dated Sep. 5, 2008, 7 pages.

Fletcher, Daniel A., Ph.D., Daniel V. Palanker, Ph.D., Philip Hule, M.D., Jason Miller, MS, Michael F. Marmor, M.D. and Mark S. Blumenkranz, M.D.; *Intravascular Drug Delivery With a Pulsed Liquid Microjet*; (Reprinted) Arch Ophthalmology; vol. 120, Sep. 2002, pp. 1206-1208.

Grant, W.M., MD, *Further Studies on Facility of Flow Through the Trabecular Meshwork, AMA Archives of Ophthalmology*, Oct. 1958, vol. 60, pp. 523-533.

Green, K. et. al, "Fate of Anterior Chamber Tracers in the Living Rhesus Monkey Eye with Evidence for Uveo-Vortex Outflow," Fourth William Mackenzie Memorial Symposium, 1977, pp. 731-739.

Grierson, I., R.C. Howes, and Q. Wang, *Age-related Changes in the Canal of Schlemm*, Exp. Eye Res., 1984, vol. 39, pp. 505-512.

Hill, R.A., Q. Ren, D.C. Nguyen, L.H. Liaw, & M.W. Berns, *Free-electron Laser (FEL) Ablation of Ocular Tissues*, Lasers Med Sci 1998, vol. 13, pp. 219-226.

Hill, Richard A., MD, George Baerveldt, MD, Serdar A. Ozler, MD, Michael Pickford, BA, Glen A. Profeta, BS, & Michael W. Berns, PhD, *Laser Trabecular Ablation (LTA)*, Lasers in Surgery and Medicine, 1991, vol. 11, pp. 341-346.

Hoerauf, Hans, Christopher Wirbelauer, Christian Scholz, Ralf Engelhardt, Peter Koch, Horst Laqua, and Reginald Birngruber, *Slit-lamp-adapted optical coherence tomography of the anterior segment*, Graefe's Arch Clin Exp Ophthalmol, 2000, vol. 238, pp. 8-18.

(56) References Cited

OTHER PUBLICATIONS

Jacobi, Phillip C., MD, Thomas S. Dietlein, MD and Gunter K. Krieglstein, MD, *Microendoscopic Trabecular Surgery in Glaucoma Management*, Ophthalmology, 1999 vol. 106, No. 3, pp. 538-544

Jacobi, Phillip C., MD, Thomas S. Dietlein, MD and Gunter K. Krieglstein, MD, *Bimanual Trabecular Aspiration in Pseudoexfoliation Glaucoma*, Ophthalmology, 1998, vol. 105, No. 5, May 1998, pp. 886-894

Jacobi, Phillip C., MD, Thomas S. Dietlein, MD and Gunter K. Krieglstein, MD, *Goniocurettage for Removing Trabecular Meshwork: Clinical Results of a new Surgical American Journal of Technique in Advanced Chronic Open-Angle Glaucoma*, Ophthalmology, May 1999, pp. 505-510

Jocson, Vincente, L., M.D.; *Air Trabeculotomy*, American Journal of Ophthalmolgy: vol. 79, o. 1, Jan.-Jun. 1975; pp. 107-111.

Johnstone, M.A., R. Stegmann, and B.A. Smit, *American Glaucoma Society, 12th Annual Meeting, Cylindrical Tubular Structures Spanning from Trabecular Meshwork Across SC*, Laboratory Studies with SEM, TEM and Tracers Correlated with Clinical Findings, Abstract No. 18., p. 39, 2002.

Jordon, et al., "A Novel Approach to Suprachoroidal Drainage for the Surgical Treatment of Intractable Glaucoma," J Glaucoma 15(3): 200-205 (2006).

Jordan, Jens, Thomas S. Dietlein, Sven Dinslage, Christoph Lüke, Walter Konen, Günter K. Krieglstein, *Cyclodialysis ab interno as a surgical approach to intractable glaucoma*, Graefe's Arch Clin Exp Ophthalmol (2007) 245:1071-1076.

Kampik, Anselm Franz Grehn, *Nutzen and Risiken Augenärzticher Therapie, Hauptreferate der XXXII, Essener Fortbilding für Augenärtze*, Dec. 1998. (English translated version enclosed Benefiets and Risks of Ophthalmological Therapy).

Katz, L. Jay, MD, *A Call for Innovative Operations for Glaucoma*, Arch Ophthalmology, Mar. 2000, vol. 118, pp. 412-413.

Klemm, A. Balazs, J. Draeger, R. Wiezorrek, *Experimental use of space-retaining substances with extended duration: functional and morphological results*, Graefe's Arch Clin Exp Ophthalmol (1995) 233:592-597.

Krejci, L., "Cyclodialysis with Hydroxyethyl Methacrylate Capillary Strip (HCS)," Opthalmologica, vol. 164 (1972).

Lee, P.F. et al., "Aqueous-venous Shunt and Intraocular Pressure. Preliminary Report of Animal Studies." (1966).

Llobet, et al., Understanding Trabecular Meshwork Physiology: A Key to the Control of Intraocular Pressure?, News Physiol Sci vol. 18, pp. 205-209 (2003).

Luntz, Maurice H., MD & D.G. Livingston, B.SC., *Trabeculotomy AB Externo & Trabeculectomy in Congenital and Adult-Onset Glaucoma*, American Journal of Ophthalmology, Feb. 1977, vol. 83, No. 2, pp. 174-179.

Matsumoto, Yasuhiro and Douglas H. Johnson, *Trabecular Meshwork Phagocytosis in Graucomatous Eyes*, Ophthalmologica 1977, vol. 211, pp. 147-152.

McGehee, Blake E. et al., "Bilateral Retinal Detachment in a Patient with Vogt-Koyanagi-Harada Syndrome," Emergency Radiology (2005) 11: 366-371.

Nickells, Robert W., *Apoptosis of Retinal Ganglion Cells in Glaucoma: An Update of the Molecular Pathways Involved in Cell Death*, Survey of Ophthalmology, vol. 43, Supplement 1, Jun. 1999, pp. S-151 through S-161.

Odrich, S., "New Technique During Complex Tube-Shunt Implantation," Journal of Glaucoma, vol. 9 (2000).

Olsen, et al., "Cannulation of the Suprachoroidal Space: A Novel Drug Delivary Methodology to the Posterior Segment", American Journal of Ophthalmology, Nov. 2006, pp. 777-787.e2 (13 pages).

Pederson, Jonathan et al., "Uveoscleral Aqueous Outflow in the Rhesus Monkey: Importance of Uveal Reabsorption," Invest. Ophthalmol, Visual Sci. Nov. 1977, Uveal Reabsorption of Aqueous Humor, vol. 16, No. 11, pp. 1008-1017.

Putney, Luanna K., Cecile Rose T. Vibat, and Martha E. O'Donnell, *Intracellular Cl Regulates Na-K-Cl Cotransport Activity in Human Trabecular Meshwork Cells*, 1999 American Physiological Society, Sep. 1999, pp. C373 through C383.

Radhakrishnan, Sumita, Andrew M. Rollins, Jonathan E. Roth, S. Yazddanfar, Volker Westphal, David Bardenstein, and Joseph Izatt, *Real-Time Optical Coherence Tomography of the Anterior Segment at 1310 nm*, Arch Ophthalmology, Aug. 2001, vol. 119, pp. 1179-1185.

Rohen, Johannes W., Grune & Stratton, Harcourt Brace Jovanovich Publishers, edited by J.E. Cairns, *Glaucoma*, vol. 1, Chapter 14, Anatomy of the Aqueous Outflow Channels, 1986 pp. 277-296.

Rosenberg, et al., "Implants in Glaucoma Surgery", The Glaucomas 1996, Chapter 88, pp. 1783-1807 (27 pages).

Rowan, MD, *Combined Cyclodialysis and Cataract Surgery*, Ophthalmic Surgery and Lasers, Dec. 1998, vol. 29, No. 12, pp. 962-968 (9 pages).

Schwartz, Arthur L., MD, & Douglas R. Anderson, MD, Trabecular Surgery, Arch Ophthalmol, vol. 92, Aug. 1974, pp. 134-138.

Shields, M. Bruce, MD, *A Study Guide for Glaucoma: Aqueous Humor Dynamics*, Copyright 1982, pp. 6-43.

Shields, M. Bruce, Aqueous Humor Dynamics, Textbook of Glaucoma, Fourth Ed., Williams & Wilkins Publishers, 1998, Ch. 2, pp. 5-31.

Spiegel, Detliev, MD, Karin Kobuch, MD, Richard A. Hill, MD, Ronald L. Gross, MD, *Schlemm's Canal Implant: A New Method to Lower Intraocular Pressure in Patients With POAG?*, Opthalmic Surgery and Lasers, Jun. 1999, vol. 30, No. 6, pp. 492-494.

Strange, Kevin (edited by), *Cellular and Molecular Physiology of Cell Volume Regulation*, Library of Congress Cataloging in-Publication Data, CRC Press, Inc., 1994 pp. 312-321.

Tatton, W.G., *Apoptotic Mechanisms in Neurodegeneration: Possible Relevance to Glaucoma*, European Journal of Ophthalmology, Jan.-Mar. 1999, vol. 9, Supplement 1, pp. S22 through S29.

Tatton, William, Ruth M.E. Chalmers-Redman, Ajay Sud, Steven M. Podos, and Thomas Mittag, *Maintaining Mitochondrial Membrane Impermeability: An Opportunity for New Therapy in Glaucoma*, Survey of Ophthalmology, vol. 45, Supplement 3, May 2001, pp. S277 through S283.

Troncoso, M.U. "Cyclodialysis with Insertion of a Metal Implant in the Treatment of Glaucoma," Archives of Ophthalmology, vol. 23 (1940).

Troncoso, M.U. "Use of the Tantalum Implants for Inducing a Permanent Hypotony in Rabbits' Eyes," American Journal of Ophthalmology, vol. 32, No. 4 (1949).

U.S. Appl. No. 09/452,963, filed Dec. 2, 1999. Title: *Expandable/Retractable Stent for Venous and Valvular Annulus Use.*

Wagner, Justin A., Edwards, Aurélie, and Schuman, Joel S., Characterization of Uveoscleral Outflow in Enucleated Porcine Eyes Perfused Under Constant Pressure, *Invest Ophthalmol Vis Sci.* Sep. 2004; 45(9): 3203-3206 (9 pages).

Zhou, Jianbo, PhD, Gregory T. Smedley, PhD., *A Trabecular Bypass Flow Hypothesis*, Feb. 2005, vol. 14 No. 1, pp. 74-83.

Toris, Carol B. "Aqueous humor dynamics I." Current topics in membranes. In: Civan, MM (Ed.) The Eye's Aqueous Humor, 62 (2008): 193-229).

The Glaucomas, 2nd Edition, Ritch, Robert, MD, et al, Chapter 15 "Uveoscleral Outflow" 1996.

Transcend Medical, Inc.'s Disclosures Pursuant to Default Discovery Rule 4(d) (Dec. 6, 2013) (341 pages).

Transcend Medical, Inc.'s Preliminary Invalidity Contentions for U.S. Pat. No. 8,579,846 (Mar. 3, 2014) (184 pages).

Transcend Medical, Inc.'s First Supplemental Invalidity Contentions (Mar. 3, 2014) (107 pages).

Glaukos Corporation's First Supplemental Response to Transcend Medical, Inc.'s Interrogatories Nos. 1-2, 4, 6 and 9 (Mar. 13, 2014) (12 pages).

Complaint for Declaratory Judgment of Patent Non-Infringement and Invalidity (May 10, 2013).

Answer and Counterclaim (May 31, 2013).

Plaintiff Transcend Medical Inc.'s Answer to Counterclaims (Jun. 24, 2013).

Glaukos Corporation's Responses to Transcend Medica, Inc.'s First Set of Interrogations (Nos. 1-11) (Aug. 15, 2013).

(56) References Cited

OTHER PUBLICATIONS

Glaukos Corporation's Responses To Transcend Medical, Inc.'s Second Set Of Interrogatories (No. 12) dated Jun. 26, 2014.
Glaukos Corporation's Responses To Transcend Medical, Inc.'s Third Set Of Interrogatories (No. 13) dated Jul. 7, 2014.
Glaukos Corporation's Responses To Transcend Medical, Inc.'s Fourth Set Of Interrogatories (Nos. 14-15) dated Aug. 29, 2014.
Glaukos Corporation's Supplemental Response To Transcend Medical, Inc.'s Interrogatory No. 3 dated Aug. 29, 2014.
Glaukos Corporation's Responses To Transcend Medical, Inc.'s Sixth Set Of Interrogatories (Nos. 20-25) dated Nov. 21, 2014.
Glaukos Corporation's Supplemental Response To Transcend Medical, Inc.'s Third Set Of Interrogatories (No. 13) dated Nov. 21, 2014.
Transcend Medical, Inc.'s First Supplemental Response To Glaukos Corporation's Interrogatory No. 1 dated Dec. 23, 2013.
Redacted Exhibits A-C of Transcend Medical, Inc.'s First Supplemental Response To Glaukos Corporation's Interrogatory No. 1 dated Dec. 23, 2013.
Transcend Medical, Inc.'s Responses and Objections To Glaukos Corporation's First Set of Interrogatories dated Oct. 24, 2013.
Transcend Medical, Inc.'s Second Supplemental Response To Glaukos Corporation's Interrogatory No. 1 dated Mar. 3, 2014.
Transcend Medical, Inc.'s Responses and Objections To Glaukos Corporation's Second Set of Interrogatories dated May 27, 2014.
Glaukos Corporation's Objections and Responses To Transcend Medical, Inc.'s First Set of Requests for Admission dated Aug. 29, 2014.
Amendment Accompanying Request for Continued Examination and Response to Office Action dated Mar. 16, 2010, filed in U.S. Appl. No. 10/987,114 (Jun. 15, 2010)(12 pages)
Notice of Allowability in U.S. Appl. No. 10/987,114 (Jul. 29, 2010)(3 pages).
Communication from European Patent Office for European App. No. 08102896.1 (Jul. 2, 2012) (5 pages).
Hoskins, H. Dunbar, et al., *Diagnosis and Therapy of the Glaucomas, Chapter 4: Aqueous Humor Outflow*, 6th edition, pp. 41-66 (1989) (28 pages).
Sherman, Steven H., et al., "The Fate of Anterior Chamber Fluorescein in the Monkey Eye 1. The Anterior Chamber Outflow Pathways", Exp. Eye Res. vol. 27, pp. 159-173 (1978) (15 pages).
Webster's Third New International Dictionary of the English Language (Unabridged), definitions of "deploy" and "deployment", p. 605 (2002) (4 pages).
*Histology of the Human Eye, An Atlas and Textbook*, Chapter Eight: Choroid (1971) (74 pages).
Transcend Medical, Inc.'s Initial Disclosures, Served Jul. 30, 2013.
Glaukos Corporation's Initial Disclosures, Served Jul. 30, 2013.
Transcend Medical, Inc.'s Supplemental Disclosures, Served Nov. 14, 2014.
Glaukos Corporation's Supplemental Disclosures, Served Oct. 29, 2014.
Deposition of John Richards, Dated Jun. 17, 2015.
Deposition Jay Katz Dated Jun. 10, 2015.
Deposition Jay Katz, Dated Oct. 1, 2014.
Transcend Medical, Inc.'s Responses and Objections to Glaukos Corporation's First Set of Requests for Admission, Served Aug. 29, 2014.
Markman Hearing Transcript before Honorable Mitchell S. Goldberg, Dated Nov. 13, 2014.
Transcend Medical, Inc.'s Answer to Counterclaims, Served Jan. 13, 2014.
Joint Claim Construction Statement, Filed Jun. 20, 2014.
Answer and Counterclaim, Filed Jan. 3, 2014.
First Amended Complaint for Declaratory Judgment of Patent Non-Infringement and Invalidity, Filed Dec. 16, 2013.
Expert Report of Harold (Hal) J. Walbrink Regarding the Invalidity of Various Claims of the Patents in Suit and the Obviousness of Certain Claim Elements (Mar. 9, 2015) (63 pages).
Expert Report of Richard Lewis, M.D. (Mar. 9, 2015) (79 pages).
Rebuttal Expert Report of John Richards (Apr. 24, 2015) (16 pages).
Rebuttal Expert Report of L. Jay Katz MD. (Apr. 24, 2015) (130 pages).
Rebuttal Expert Report of Richard Lewis, M.D. (Apr. 24, 2015) (39 pages).
Rebuttal Expert Report of Ron Yamamoto (Apr. 24, 2015) (65 pages).
Expert Supplemental Report of Harold (Hal) J. Walbrink Regarding the Invalidity of Various Claims of The Patents-in-suit and the Obviousness of Certain Claim Elements (May 8, 2015) (17 pages).
Transcend Medical, Inc.'s Second Supplemental Invalidity Contentions, Aug. 26, 2014, 39 pages.
Declaration of Joseph F. Jennings in Support of Glaukos's Opening Claim Construction Brief, Jul. 18, 2014, 237 pages.
Declaration of Dr. L. Jay Katz in Support of Glaukos's Opening Claim Construction Brief, Jul. 17, 2014, 78 pages.
Glaukos' Opening Claim Construction Brief, Jul. 18, 2014, 30 pages.
Transcends's Answering Claim Construction Brief, Aug. 15, 2014, 461 pages.
Glaukos Corporation's Reply Claim Construction Brief, Aug. 29, 2014, 14 pages.
Transcend Medical, Inc.'s Redacted Second Amended Complaint for Declaratory Judgment of Patent Non-Infringement, Invalidity and Unenforceability, Sep. 10, 2014, 206 pages.
Transcend Medical, Inc.'s Redacted Exhibit A to the Stipulation and Proposed Order for Second Amended Complaint and Amendment of Scheduling Order, Sep. 11, 2014, 205 pages.
Transcend Medical, Inc's Redacted Sur-Reply Claim Construction Brief, Sep. 17, 2014, 14 pages.
Glaukos Corporation's Redacted Answer and Counterclaims to the Second Amended Complaint for Declaratory Judgment, Sep. 29, 2014, 27 pages.
Transcend's Answer to Counterclaims, Oct. 17, 2014, 10 pages.
G.B. Bietti, "The Present State of the Use of Plastics in Eye Surgery," Acta Ophthalmologica, vol. 33, No. 4, 1955, pp. 337-370, 34 pages.
Cullen et al., "Anterior Chamber to Frontal Sinus Shunt for the Diversion of Aqueous Humor: A Pilot Study in Four Normal Dogs," Veterinary Ophthalmology, vol. 1, No. 1, 1998, pp. 31-39, 9 pages.
M. A. Coote, "Glaucoma Hollow Fiber Filters—A New Glaucoma Seton. Preliminary Results," J. Glaucoma, vol. 8, No. 1, Supplement, 1999, p. S4, 1 page.
L. Krejci, "Cyclodialysis with Hydroxyethyl Methacrylate Capillary Strip (HCS)," Opthalmologica, vol. 164, 1972, pp. 113-121, 9 pages.
P.F. Lee and C.L. Schepens, "Aqueous-venous Shunt and Intraocular Pressure. Preliminary Report of Animal Studies," Investigative Opthalmology, vol. 5, No. 1, Feb. 1966, pp. 59-64, 6 pages.
S. Odrich, "New Technique During Complex Tube-Shunt Implantation," Journal of Glaucoma, vol. 9, No. 3, 2000, pp. 278-289, 2 pages.
G.L. Portney, "Silicone Elastomer Implantation Cyclodialysis," Archives of Ophthalmology, vol. 89, No. 1, Jan. 1973, pp. 10-12, 3 pages.
D. Spiegel, K. Kobuch, R. Hill, R. Gross, "Schlemm's Canal Implant: A New Method to Lower Intraocular Pressure in Patients with POAG?", Opthalmic Surgery and Lasers, vol. 30, No. 6, Jun. 1999, pp. 492-494, 3 pages.
M.U. Troncoso, "Cyclodialysis with Insertion of a Metal Implant in the Treatment of Glaucoma," Archives of Ophthalmology, vol. 23, 1940, pp. 270-300, 31 pages.
M.U. Troncoso, "Use of Tantalum Implants for Inducing a Permanent Hypotony in Rabbits' Eyes," American Journal of Ophthalmology, vol. 32, No. 4, Apr. 1949, pp. 499-508, 10 pages.
Excerpts from the certified Deposition Transcript of Richard A. Hill, M.D., Jul. 17, 2014, pp. 1, 3-4, 240-253, and 270.
Excerpts from the certified Deposition Transcript of Gregory Smedley, Ph.D., Aug. 6, 2014, pp. 1, 3-4, 6-7, 12, 99-102, 106-114, and 203.
Deposition Transcript of M. Bruce Shields dated Jun. 3, 2015 [Redacted-Public Version].
Memorandum Opinion re Claim Construction dated Jan. 16, 2015.
Order re Claim Construction dated Jan. 16, 2015.

(56) References Cited

OTHER PUBLICATIONS

Glaukos's Motion for Summary Judgment on Transcend's Third Cause of Action for a Declaratory Judgment of Unenforceability for Inequitable Conduct dated Jun. 12, 2015.
Glaukos's Opening Brief in Support of Glaukos's Motion for Summary Judgment on Transcend's Third Cause of Action for a Declaratory Judgment of Unenforceability for Inequitable Conduct dated Jun. 12, 2015.
Glaukos's Statement of Undisputed Material Fact dated Jun. 12, 2015.
Transcend's Motion for Summary Judgment of Invalidity dated Jun. 12, 2015.
Transcend's Motion for Summary Judgment of Non-Infringement dated Jun. 12, 2015.
Transcend's Memorandum in Support of Transcend's Motion for Summary Judgment of Invalidity dated Jun. 19, 2015 [Redacted-Public Version].
Transcend's Statement of Undisputed Facts in Support of Transcend's Motion for Summary Judgment of Invalidity dated Jun. 19, 2015 [Redacted-Public Version].
Declaration of Vasquez in Support of Transcend's Motion for Summary Judgment of Non-Infringement dated Jun. 19, 2015 [Redacted-Public Version].
Declaration of Du Vergier in Support of Transcend's Motion for Summary Judgment of Non-Infringement dated Jun. 19, 2015 [Redacted-Public Version].
Response to Office Action Dated Sep. 18, 2009 (dated Mar. 18, 2010) from the prosecution history of U.S. Pat. No. 8,075,511 to Tu et al.
L. Jay Katz, *Ciliochoroidal Detachment*, 18:3 Ophthalmic Surgery 175, (Mar. 1987).
Tin A. Tun et al.,"Measurement of Trabecular Meshwork Width Using Swept Source Optical Coherence Tomography—Abstract" (May 2012) available at: http://www.abstractsonline.com/Plan/ViewAbstract.aspx?sKey=6e904fa6-4f1b-406a-8fd9-3ad7551c527d&cKey=80031868-31bf-4b5e-8043-d3e5aedc7bf0 (last visited Jun. 12, 2015).
Tin A. Tun et al., *Assessment of Trabecular Meshwork Width Using Swept Source Optical Coherence Tomography*, 251:6 Graefes Arch. Clin. Exp. Ophthalmol. 1587 (2013).
"Transcend Medical CyPass® System—Instructions for Use," (Release date Apr. 29, 2013).
Hady Saheb et al., *Optical Coherence Tomography of the Suprachoroid After CyPass Micro-Stent Implantation for the Treatment of Open-Angle Glaucoma*, Br. J. Ophthalmology, 98:19-23 (2014).
Helmut Hoeh et al., *Early Postoperative Safety and Surgical Outcomes After Implantation of a Suprachoroidal Micro-Stent for the Treatment of Open-Angle Glaucoma Concomitant with Cataract Surgery*, 39 J. Cataract Refract. Surg. 431 (2013).
Nir Shoham-Hazon et al., "Stability and Predictive Value of OCT Findings After CyPass Suprachoroidal Micro-Stent Implantation," available at: http://transcendmedical.com/wp-content/uploads/2014/12/TM-AGS-2012-F2-final.pdf (last visited Jun. 12, 2015).
Schocket, *Investigations of the Reasons for Success and Failure in the Anterior Shunt-to-the Encircling-Band Procedure in the Treatment of Refractory Glaucoma*, Tr. Am. Ophth. Soc., 84:743 (1986).
Tsontcho Ianchulev, *Chapter 21: The CyPass Suprachoroidal Micro-Stent*, in J.R. Samples & I.I.K. Ahmed (eds.), *Surgical Innovations in Glaucoma* 229 (Springer Science+Business Media 2014).
Excerpt of Ramesh C. Tripathi & Brenda J. Tripathi, *Chapter 1: Anatomy of the Human Eye, Orbit, and Adnexa*, in Ramesh C. Tripathi & Brenda J. Tripathi, *The Eye* (Academic Press, Inc. 1984).
Final Office Action (dated Jun. 9, 2014) from the prosecution history of U.S. Appl. No. 13/786,357.
Tsontcho Ianchulev, *Chapter 3: Suprachoroidal Space as a Therapeutic Target*, in J.R. Samples & I.I.K. Ahmed (eds.), *Surgical Innovations in Glaucoma* 33 (Springer Science+Business Media 2014).
Declaration of Alyse Katz in Support of Motion for Summary Judgment of Invalidity dated Jun. 19, 2015 [Redacted-Public Version].
U.S. Appl. No. 60/281,973, entitled "Glaucoma Shunt and Methods Thereof for Glaucoma Treatment," to Tu (filed Apr. 17, 2001).
Communication of the Board of Appeal Pursuant to Article 15(1) of the Rules of Procedure of the Boards of Appeal, submitted in the prosecution history of EP1977724, dated May 8, 2014 (Board of Appeal Communication, EP1977724.
Decision of Technical Board of Appeal 3.2.08 of Jan. 15, 2015, submitted in the prosecution history of EP1977724, dated Jan. 15, 2015.
Webpage regarding the definition of "subchoroidal" from Merriam Webster's Medical Dictionary, available at: http://www.merriam-webster.com/medical/subchoroidal (last visited Jun. 11, 2015).
Petition to Correct Inventorship in a Patent Pursuant to 35 U.S.C. § 256 and 37 C.F.R. § 1.324, filed in the prosecution history of U.S. Pat. No. 7,857,782 dated May 2014.
Petition to Correct Inventorship in a Patent Pursuant to 35 U.S.C. § 256 and 37 C.F.R. § 1.324, filed in the prosecution history of U.S. Pat. No. 8,075,511 dated May 2014.
Petition to Correct Inventorship in a Patent Pursuant to 35 U.S.C. § 256 and 37 C.F.R. § 1.324, filed in the prosecution history of U.S. Pat. No. 8,579,846 dated May 2014.
Correspondence from the U.S. Patent and Trademark Office granting the petition to correct inventorship, filed in the prosecution history of U.S. Pat. No. 7,857,782 (dated Nov. 18, 2014).
Correspondence from the U.S. Patent and Trademark Office granting the petition to correct inventorship, filed in the prosecution history of U.S. Pat. No. 8,075,511 (dated Oct. 31, 2014).
Correspondence from the U.S. Patent and Trademark Office granting the petition to correct inventorship, filed in the prosecution history of U.S. Pat. No. 8,579,846 (dated Feb. 10, 2015).
Declaration of Joshua Stowell in Support of Glaukos's Motion for Summary Judgment on Transcend's Third Cause of Action for a Declaratory Judgment of Unenforceability for Inequitable Conduct dated Jun. 19, 2015 [Redacted-Public Version].
Excerpts from the file history of U.S. Pat. No. 7,563,241 dated Mar. 13, 2009.
Transcend's Responses and Objections to Glaukos Corporation's Fifth Set of Interrogatories dated Nov. 20, 2014.
Transcend's First Supplemental Response to Glaukos Corporation's Interrogatory Nos. 17 and 18 dated May 13, 2014.
Excerpts from the certified Deposition Transcript of Barbara Niksch, dated Jun. 6, 2014.
Office Action from the USPTO dated Jun. 28, 2010 and Glaukos's response to that Office Action from the file history of U.S. Pat. No. 8,075,511.
Office Action from the USPTO dated Sep. 18, 2009 and Glaukos's response to that Office Action from the file history of U.S. Pat. No. 8,075,511.
Notice of Allowance issued by the USPTO from the file history of U.S. Pat. No. 8,579,846 (signed by Examiner Jul. 31, 2013).
Excerpts from the certified Deposition Transcript of David Haffner, dated May 28, 2014.
Declaration of Richard Lewis M.D. In Support of Glaukos's Oppositions to Transcend's Motions for Summary Judgment of Non-Infringement and Invalidity dated Jul. 2, 2015.
Declaration of Ron Yamamoto in Support of Glaukos's Opposition to Transcend's Motion for Summary Judgment of Invalidity dated Jul. 2, 2015.
Declaration of John Richards in Support of Glaukos's Opposition to Transcend's Motion for Summary Judgment of Invalidity dated Jul. 2, 2015.
Glaukos's Opposition to Transcend's Motion for Summary Judgment of Invalidity dated Jul. 2, 2015.
Transcend's Memorandum in Opposition to Glaukos' Motion for Summary Judgment of No Inequitable Conduct dated Jul. 9, 2015 [Redacted-Public Version].
Declaration of Julien Du Vergier in Support of Transcend's Opposition to Glaukos' Motion for Summary Judgment of No Inequitable Conduct dated Jul. 9, 2015 [Redacted-Public Version].

(56) References Cited

OTHER PUBLICATIONS

Transcend's Response and Statement of Further Undisputed Facts in Support of its Opposition to Glaukos' Motion for Summary Judgment of No Inequitable Conduct dated Jul. 9, 2015 [Redacted-Public Version].
Website entitled, "About Glaukos—History," available at: http://www.glaukos.com/about-glaukos/history (last accessed Jun. 29, 2015).
Excerpt from the prosecution history of U.S. Pat. No. 7,857,782, including the Inventor Declaration dated Jun. 14, 2002.
Excerpt from the prosecution history of U.S. Pat. No. 8,075,511, including the Inventor Declaration dated Jun. 14, 2002.
Excerpt from the prosecution history of U.S. Pat. No. 8,579,846, including the Inventor Declaration dated Jun. 14, 2002.
Excerpt from the prosecution history of U.S. Appl. No. 09/549,350, including the Inventor Declaration (dated Aug./Sep. 2000).
Excerpt from the prosecution history of U.S. Appl. No. 09/704,276, including the Inventor Declaration (dated Feb. 2001).
U.S. Appl. No. 09/704,276, filed Nov. 1, 2000 [now U.S. Pat. No. 6,736,791].
Excerpt of the transcript from the deposition of David Schetter on Dec. 18, 2014.
U.S. Appl. No. 60/276,609, filed Mar. 16, 2001.
Request for Correction of Inventorship Under 37 C.F.R. § 1.48(d), dated May 27, 2014 and filed in the prosecution history of U.S. Appl. No. 60/281,973.
"Changing Perspectives in Glaucoma Management," *Innovations in Glaucoma* 2010.
Richard Hill, MD, "Inventor's Perspective," Glaucoma Today (Nov./Dec. 2012).
Website entitled, "2013 Ophthalmology Innovation Summit Innovator Awards," dated Nov. 14, 2013 available at: http://ois.net/2013-ophthalmology-innovator-award/ (last visited Jun. 29, 2015).
Excerpt of Transcend's First Set of Interrogatories to Defendant Glaukos Corporation dated Jul. 16, 2013.
Excerpt of Transcend's First Set of Requests for Production to Defendant Glaukos Corporation dated Jul. 16, 2013.
Subpoena to Produce Documents, Information, or Objects or to Permit Inspection of Premises in a Civil Action propounded on Dr. Richard A. Hill, Feb. 11, 2014.
Glaukos's Opposition to Transcend's Motion for Summary Judgment of Non-Infringement dated Jul. 9, 2015 [Redacted-Public Version].
Glaukos's Statement of Material Facts that Present Genuine Issues for Trial in Opposition to Transcend's Motion for Summary Judgment of Non-Infringement dated Jul. 9, 2015 [Redacted-Public Version].
Declaration of L. Jay Katz in Support of Glaukos's Oppositions to Transcend's Motions for Summary Judgment of Non-Infringement and Invalidity dated Jul. 9, 2015 [Redacted-Public Version].
Declaration of Joshua Stowell in Support of Glaukos's Opposition to Transcend's Motion for Summary Judgment of Invalidity dated Jul. 9, 2015 [Redacted-Public Version].
Excerpts from the certified Deposition Transcript of Richard Lewis, M.D., dated Jun. 5, 2015.
Excerpts from the certified Deposition Transcript of Joseph Caprioli, M.D., dated May 27, 2015.
Excerpts from the certified Deposition Transcript of Ron Yamamoto, dated May 22, 2015.
Glaukos's Statement of Material Facts that Present Genuine Issues for Trial in Opposition to Transcend's Motion for Summary Judgment of Invalidity dated Jul. 9, 2015 [Redacted-Public Version].
Declaration of Joseph F. Jennings in Support of Glaukos's Opposition to Transcend's Motion for Summary Judgment of Non-Infringement dated Jul. 9, 2015 [Redacted-Public Version].
Duane's Ophthalmology on CD-ROM, 2006 Edition, Chapter 56—Medical Therapy of Glaucoma by Marc Weitzman and Joseph Caprioli.
Transcend's Reply in Support of its Motion for Summary Judgment of Invalidity dated Jul. 17, 2015 [Redacted-Public Version].

Declaration of Alyse L. Katz in Support of Transcend's Reply in Support of its Motion for Summary Judgment of Invalidity [Redacted-Public Version].
Amendment and Response to Office Action, filed in the prosecution of U.S. Appl. No. 13/786,357 on May 6, 2014.
Transcend's Reply in Support of its Motion for Summary Judgment of Non-Infringement dated Jul. 17, 2015 [Redacted-Public Version].
Declaration of Julien Du Vergier in Support of Transcend's Reply in Support of its Motion for Summary Judgment of Non-Infringement dated Jul. 17, 2015 [Redacted-Public Version].
Glaukos's Reply in Support of its Motion for Summary Judgment on Transcend's Third Cause of Action for a Declaratory Judgment of Unenforceability for Inequitable Conduct dated Jul. 17, 2015 [Redacted-Public Version].
Second Declaration of Joshua Stowell in Support of Glaukos's Motion for Summary Judgment on Transcend's Third Cause of Action for a Declaratory Judgment of Unenforceability for Inequitable Conduct dated Jul. 17, 2015 [Redacted-Public Version].
Transcend's Letter to Judge Regarding Citation Errors and Missing Exhibit Pages in Briefing Papers dated Jul. 28, 2015.
Memorandum Opinion in connection with Summary Judgment on the Issue of Invalidity, dated Sep. 18, 2015.
Order Granting in Part and Denying in Part Transcend Medical, Inc.'s Motion for Summary Judgment of Invalidity, dated Sep. 18, 2015.
Memorandum Opinion in connection with Summary Judgment on the Issue of Infringement, dated Sep. 18, 2015.
Order Granting Transcend Medical Inc.'s Motion for Summary Judgment of Non-Infringement, dated Sep. 18, 2015.
Memorandum Opinion in connection with Summary Judgment Regarding Unenforceability due to Inequitable Conduct, dated Sep. 18, 2015.
Order Denying Glaukos Corporation's Motion for Summary Judgment Regarding Unenforceability due to Inequitable Conduct, dated Sep. 18, 2015.
Proposed Pretrial Order, dated Sep. 30, 2015.
Declaration of Joseph F. Jennings in Support of Glaukos's Opening Claim Construction Brief (Jul. 18, 2014) (237 pages).
Transcend Medical, Inc.'s Responses and Objections to Glaukos Corporation's Fourth Set of Interrogatories, Served Aug. 29, 2014 [Redacted-Public Version].
Transcend's Memorandum in Support of Transcend's Motion for Summary Judgment of Non-Infringement dated Jun. 19, 2015 [Redacted-Public Version].
Transcend's Statement of Undisputed Facts in Support of Transcend's Motion for Summary Judgment of Non-Infringement dated Jun. 19, 2015 [Redacted-Public Version].
Jordan et al., Cyclodialysis ab interno as a surgical approach to intractable glaucoma, Graefe's Arch Clin Exp Opthalmol (2007) 245, pp. 1071-1076.
Tsontcho Ianchulev et al., "Minimally Invasive Ab-Interno Suprachoroidal Device (CyPass) for IOP Control in Open-Angle Glaucoma," presented at the Annual Meeting of the American Academy of Ophthalmology Oct. 16-19, 2010, Chicago, IL.
Partial File History of U.S. Pat. No. 6,638,239 (Apr. 14, 2000) (36 pages).
Office Action in U.S. Appl. No. 12/111,033 (Sep. 18, 2009) (10 pages).
Response to Office Action in U.S. Appl. No. 12/111,033 (Mar. 18, 2010) (15 pages).
Interview Summary in U.S. Appl. No. 12/979,249, mailed May 29, 2013.
Notice of Allowance in U.S. Appl. No. 12/979,249, mailed Jun. 3, 2014.
Notice of Allowance in U.S. Appl. No. 12/979,249, mailed Oct. 1,2014.
Notice of Allowance in U.S. Appl. No. 12/979,249, mailed Jan. 21, 2015.
Notice of Allowance in U.S. Appl. No. 12/979,249, mailed Feb. 25, 2016.

(56) References Cited

OTHER PUBLICATIONS

Amendment and Response to Office Action in U.S. Appl. No. 13/786,357 (May 6, 2014) (46 pages).

* cited by examiner

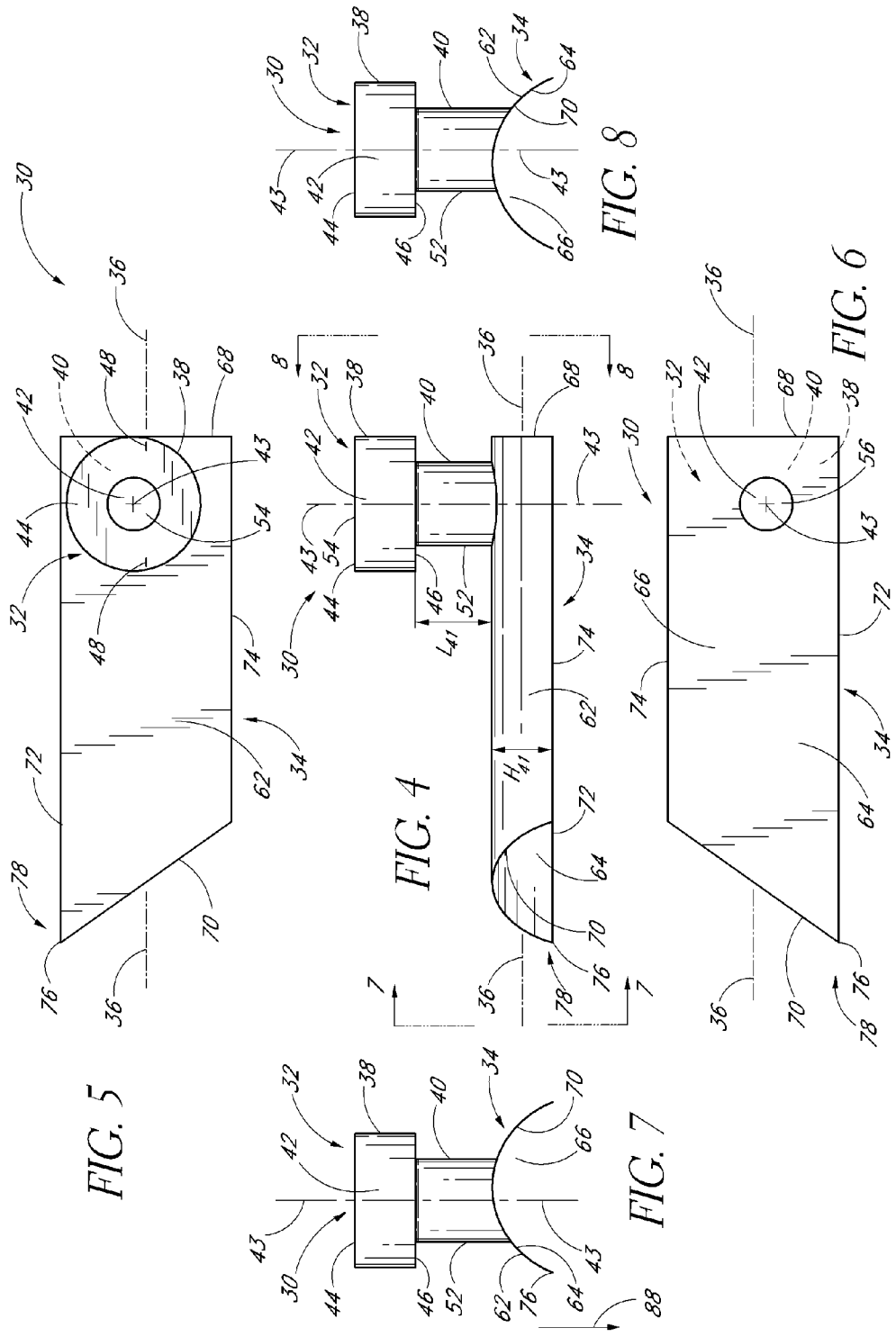

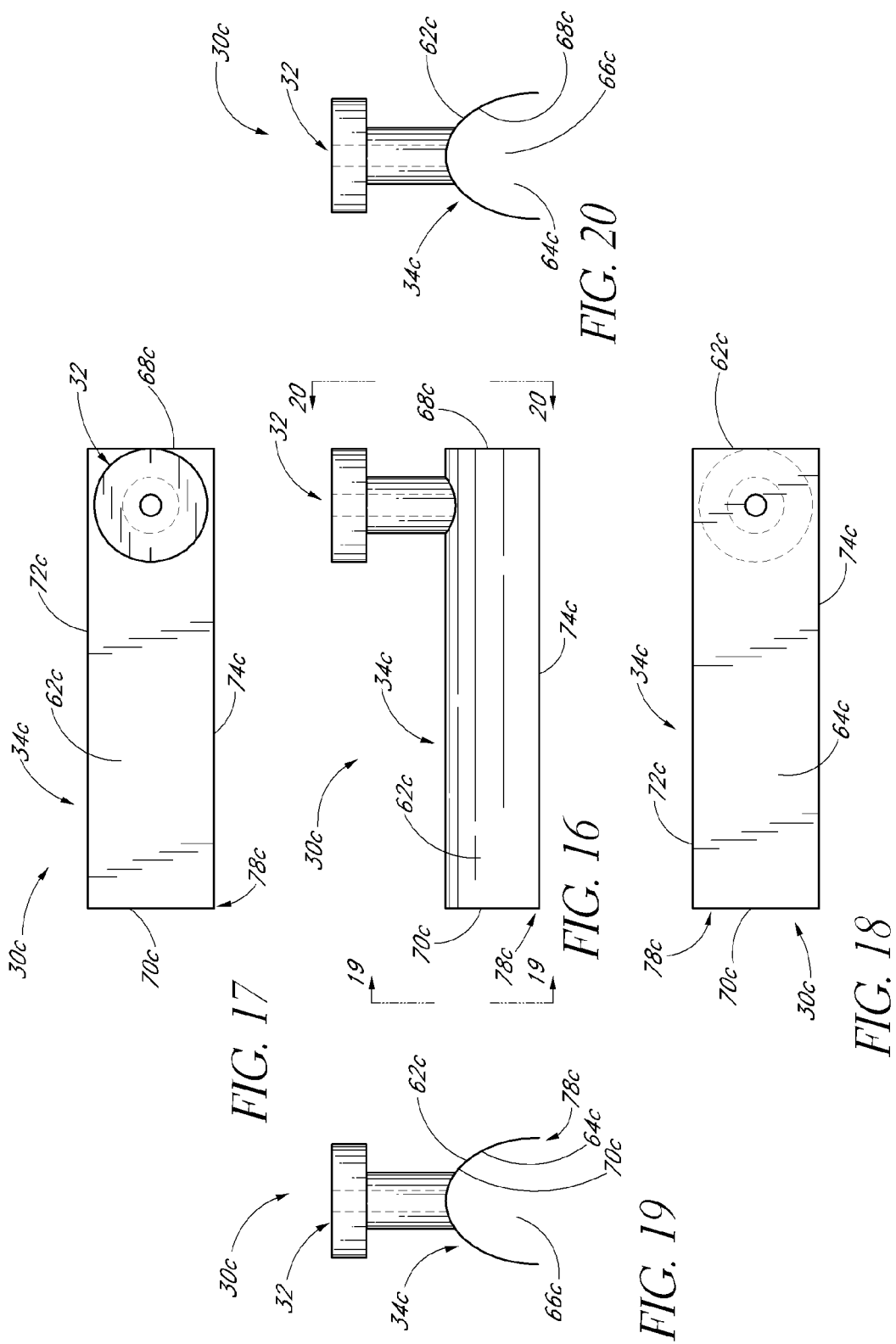

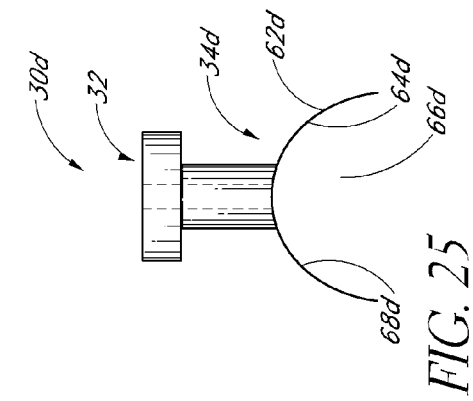
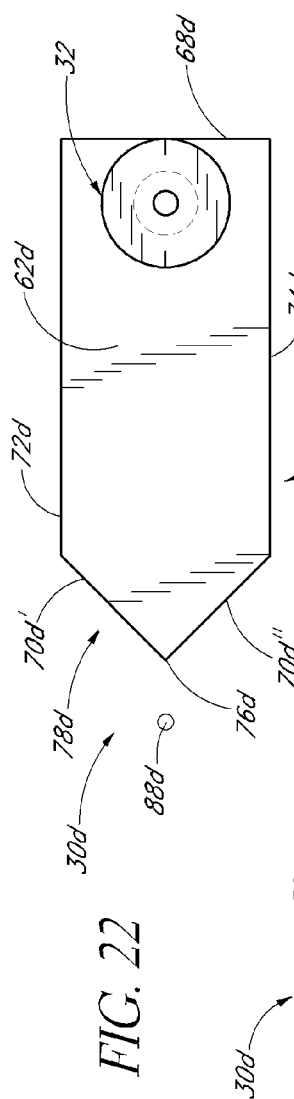
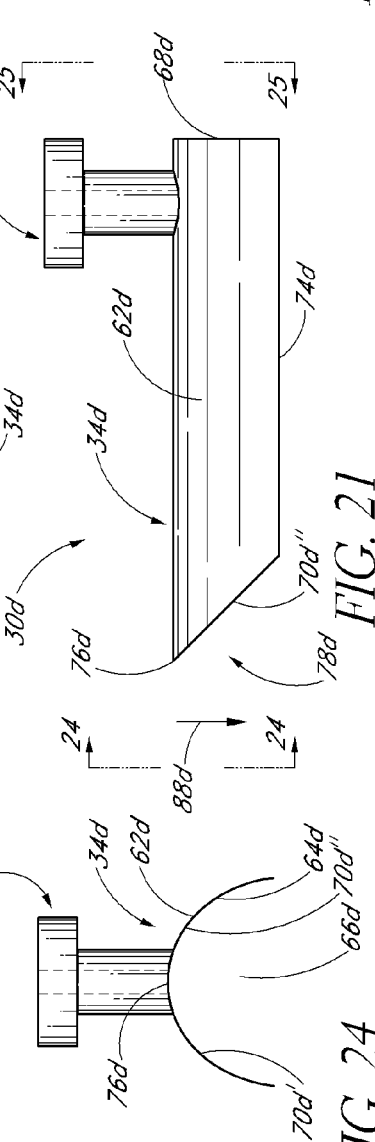
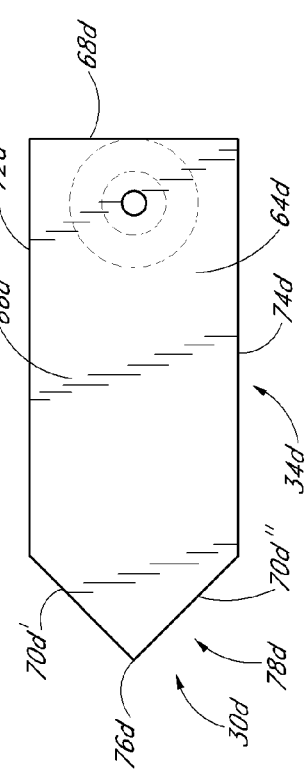
FIG. 22　　FIG. 21　　FIG. 25
FIG. 24　　FIG. 23

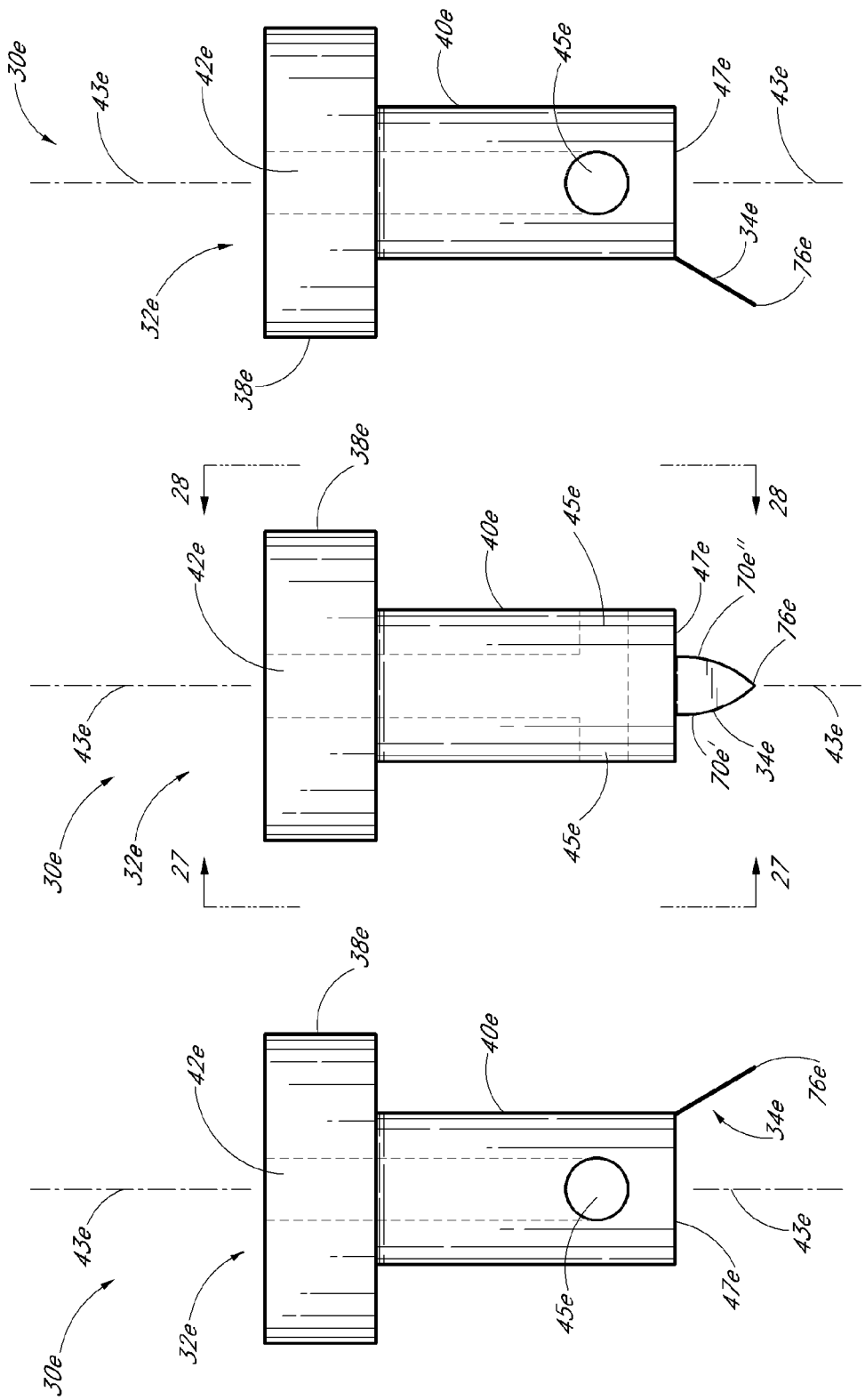

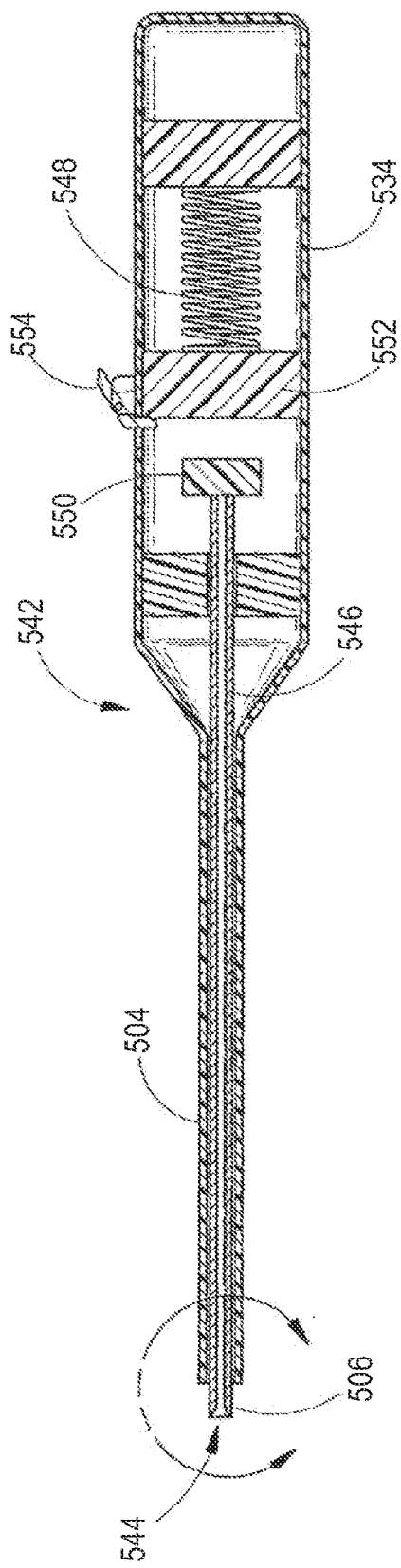
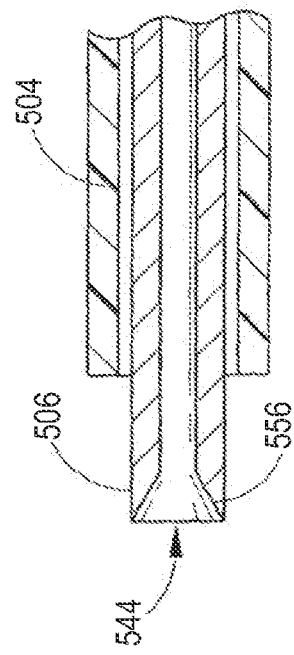
FIG. 49A
FIG. 49B

OCULAR DISORDER TREATMENT METHODS AND SYSTEMS

RELATED APPLICATIONS

This application is a continuation of U.S. patent application Ser. No. 13/301,648, filed Nov. 21, 2011, entitled OCULAR IMPLANT SYSTEMS, now U.S. Pat. No. 8,579, 846, which is a continuation of U.S. patent application Ser. No. 12/366,508, filed Feb. 5, 2009, entitled SELF-TREPHINING IMPLANT AND METHODS THEREOF FOR TREATMENT OF OCULAR DISORDERS, now U.S. Pat. No. 8,062,244, which is a divisional of U.S. patent application Ser. No. 11/598,542, filed Nov. 13, 2006, entitled IMPLANT AND METHODS THEREOF FOR TREATMENT OF OCULAR DISORDERS, now U.S. Pat. No. 7,563,241, which is a continuation of U.S. patent application Ser. No. 10/118,578, filed Apr. 8, 2002, entitled GLAUCOMA STENT AND METHODS THEREOF FOR GLAUCOMA TREATMENT, now U.S. Pat. No. 7,135,009, which claims the benefit of U.S. Provisional Application No. 60/281,973, filed Apr. 7, 2001, entitled GLAUCOMA SHUNT AND METHODS THEREOF FOR GLAUCOMA TREATMENT, the entire contents of each of which are hereby incorporated by reference herein.

BACKGROUND OF THE INVENTION

Field of the Invention

The invention relates generally to medical devices and methods for reducing the intraocular pressure in an animal eye and, more particularly, to shunt type devices for permitting aqueous outflow from the eye's anterior chamber and associated methods thereof for the treatment of glaucoma.

Description of the Related Art

The human eye is a specialized sensory organ capable of light reception and able to receive visual images. The trabecular meshwork serves as a drainage channel and is located in anterior chamber angle formed between the iris and the cornea. The trabecular meshwork maintains a balanced pressure in the anterior chamber of the eye by draining aqueous humor from the anterior chamber.

About two percent of people in the United States have glaucoma. Glaucoma is a group of eye diseases encompassing a broad spectrum of clinical presentations, etiologies, and treatment modalities. Glaucoma causes pathological changes in the optic nerve, visible on the optic disk, and it causes corresponding visual field loss, resulting in blindness if untreated. Lowering intraocular pressure is the major treatment goal in all glaucomas.

In glaucomas associated with an elevation in eye pressure (intraocular hypertension), the source of resistance to outflow is mainly in the trabecular meshwork. The tissue of the trabecular meshwork allows the aqueous humor ("aqueous") to enter Schlemm's canal, which then empties into aqueous collector channels in the posterior wall of Schlemm's canal and then into aqueous veins, which form the episcleral venous system. Aqueous humor is a transparent liquid that fills the region between the cornea, at the front of the eye, and the lens. The aqueous humor is continuously secreted by the ciliary body around the lens, so there is a constant flow of aqueous humor from the ciliary body to the eye's front chamber. The eye's pressure is determined by a balance between the production of aqueous and its exit through the trabecular meshwork (major route) or uveal scleral outflow (minor route). The trabecular meshwork is located between the outer rim of the iris and the back of the cornea, in the anterior chamber angle. The portion of the trabecular meshwork adjacent to Schlemm's canal (the juxtacanilicular meshwork) causes most of the resistance to aqueous outflow.

Glaucoma is grossly classified into two categories: closed-angle glaucoma, also known as angle closure glaucoma, and open-angle glaucoma. Closed-angle glaucoma is caused by closure of the anterior chamber angle by contact between the iris and the inner surface of the trabecular meshwork. Closure of this anatomical angle prevents normal drainage of aqueous humor from the anterior chamber of the eye.

Open-angle glaucoma is any glaucoma in which the angle of the anterior chamber remains open, but the exit of aqueous through the trabecular meshwork is diminished. The exact cause for diminished filtration is unknown for most cases of open-angle glaucoma. Primary open-angle glaucoma is the most common of the glaucomas, and it is often asymptomatic in the early to moderately advanced stage. Patients may suffer substantial, irreversible vision loss prior to diagnosis and treatment. However, there are secondary open-angle glaucomas which may include edema or swelling of the trabecular spaces (e.g., from corticosteroid use), abnormal pigment dispersion, or diseases such as hyperthyroidism that produce vascular congestion.

Current therapies for glaucoma are directed at decreasing intraocular pressure. Medical therapy includes topical ophthalmic drops or oral medications that reduce the production or increase the outflow of aqueous. However, these drug therapies for glaucoma are sometimes associated with significant side effects, such as headache, blurred vision, allergic reactions, death from cardiopulmonary complications, and potential interactions with other drugs. When drug therapy fails, surgical therapy is used. Surgical therapy for open-angle glaucoma consists of laser trabeculoplasty, trabeculectomy, and implantation of aqueous shunts after failure of trabeculectomy or if trabeculectomy is unlikely to succeed. Trabeculectomy is a major surgery that is widely used and is augmented with topically applied anticancer drugs, such as 5-flurouracil or mitomycin-C to decrease scarring and increase the likelihood of surgical success.

Approximately 100,000 trabeculectomies are performed on Medicare-age patients per year in the United States. This number would likely increase if the morbidity associated with trabeculectomy could be decreased. The current morbidity associated with trabeculectomy consists of failure (10-15%); infection (a lifelong risk of 2-5%); choroidal hemorrhage, a severe internal hemorrhage from low intraocular pressure, resulting in visual loss (1%); cataract formation; and hypotony maculopathy (potentially reversible visual loss from low intraocular pressure).

For these reasons, surgeons have tried for decades to develop a workable surgery for the trabecular meshwork.

The surgical techniques that have been tried and practiced are goniotomy/trabeculotomy and other mechanical disruptions of the trabecular meshwork, such as trabeculopuncture, goniophotoablation, laser trabecular ablation, and goniocurretage. These are all major operations and are briefly described below.

Goniotomy/Trabeculotomy: Goniotomy and trabeculotomy are simple and directed techniques of microsurgical dissection with mechanical disruption of the trabecular meshwork. These initially had early favorable responses in the treatment of open-angle glaucoma. However, long-term review of surgical results showed only limited success in adults. In retrospect, these procedures probably failed due to cellular repair and fibrosis mechanisms and a process of "filling in." Filling in is a detrimental effect of collapsing and closing in of the created opening in the trabecular meshwork. Once the created openings close, the pressure builds back up and the surgery fails.

Trabeculopuncture: Q-switched Neodynium (Nd) YAG lasers also have been investigated as an optically invasive technique for creating full-thickness holes in trabecular meshwork. However, the relatively small hole created by this trabeculopuncture technique exhibits a filling-in effect and fails.

Goniophotoablation/Laser Trabecular Ablation: Goniophotoablation is disclosed by Berlin in U.S. Pat. No. 4,846, 172 and involves the use of an excimer laser to treat glaucoma by ablating the trabecular meshwork. This was demonstrated not to succeed by clinical trial. Hill et al. used an Erbium:YAG laser to create full-thickness holes through trabecular meshwork (Hill et al., Lasers in Surgery and Medicine 11:341-346, 1991). This technique was investigated in a primate model and a limited human clinical trial at the University of California, Irvine. Although morbidity was zero in both trials, success rates did not warrant further human trials. Failure was again from filling in of surgically created defects in the trabecular meshwork by repair mechanisms. Neither of these is a viable surgical technique for the treatment of glaucoma.

Goniocurretage: This is an ab interno (from the inside), mechanically disruptive technique that uses an instrument similar to a cyclodialysis spatula with a microcurrette at the tip. Initial results were similar to trabeculotomy: it failed due to repair mechanisms and a process of filling in.

Although trabeculectomy is the most commonly performed filtering surgery, viscocanulostomy (VC) and non penetrating trabeculectomy (NPT) are two new variations of filtering surgery. These are ab externo (from the outside), major ocular procedures in which Schlemm's canal is surgically exposed by making a large and very deep scleral flap. In the VC procedure, Schlemm's canal is cannulated and viscoelastic substance injected (which dilates Schlemm's canal and the aqueous collector channels). In the NPT procedure, the inner wall of Schlemm's canal is stripped off after surgically exposing the canal.

Trabeculectomy, VC, and NPT involve the formation of an opening or hole under the conjunctiva and scleral flap into the anterior chamber, such that aqueous humor is drained onto the surface of the eye or into the tissues located within the lateral wall of the eye. These surgical operations are major procedures with significant ocular morbidity. When trabeculectomy, VC, and NPT are thought to have a low chance for success, a number of implantable drainage devices have been used to ensure that the desired filtration and outflow of aqueous humor through the surgical opening will continue. The risk of placing a glaucoma drainage device also includes hemorrhage, infection, and diplopia (double vision).

Examples of implantable shunts and surgical methods for maintaining an opening for the release of aqueous humor from the anterior chamber of the eye to the sclera or space beneath the conjunctiva have been disclosed in, for example, U.S. Pat. No. 6,059,772 to Hsia et al., and U.S. Pat. No. 6,050,970 to Baerveldt.

All of the above surgeries and variations thereof have numerous disadvantages and moderate success rates. They involve substantial trauma to the eye and require great surgical skill in creating a hole through the full thickness of the sclera into the subconjunctival space. The procedures are generally performed in an operating room and have a prolonged recovery time for vision.

The complications of existing filtration surgery have prompted ophthalmic surgeons to find other approaches to lowering intraocular pressure.

The trabecular meshwork and juxtacanilicular tissue together provide the majority of resistance to the outflow of aqueous and, as such, are logical targets for surgical removal in the treatment of open-angle glaucoma. In addition, minimal amounts of tissue are altered and existing physiologic outflow pathways are utilized.

As reported in Arch. Ophthalm. (2000) 118:412, glaucoma remains a leading cause of blindness, and filtration surgery remains an effective, important option in controlling the disease. However, modifying existing filtering surgery techniques in any profound way to increase their effectiveness appears to have reached a dead end. The article further states that the time has come to search for new surgical approaches that may provide better and safer care for patients with glaucoma.

Therefore, there is a great clinical need for a method of treating glaucoma that is faster, safer, and less expensive than currently available modalities.

SUMMARY OF THE INVENTION

The trabecular meshwork and juxtacanilicular tissue together provide the majority of resistance to the outflow of aqueous and, as such, are logical targets for surgical approach in the treatment of glaucoma. Various embodiments of glaucoma shunts are disclosed herein for aqueous to exit through the trabecular meshwork (major route) or uveal scleral outflow (minor route) or other route effective to reduce intraocular pressure (IOP).

Glaucoma surgical morbidity would greatly decrease if one were to bypass the focal resistance to outflow of aqueous only at the point of resistance, and to utilize remaining, healthy aqueous outflow mechanisms. This is in part because episcleral aqueous humor exerts a backpressure that prevents intraocular pressure from going too low, and one could thereby avoid hypotony. Thus, such a surgery would virtually eliminate the risk of hypotony-related maculopathy and choroidal hemorrhage. Furthermore, visual recovery would be very rapid, and the risk of infection would be very small, reflecting a reduction in incidence from 2-5% to about 0.05%.

U.S. application Ser. No. 09/549,350, filed Apr. 14, 2000, entitled APPARATUS AND METHOD FOR TREATING GLAUCOMA, now U.S. Pat. No. 6,638,239, and U.S. application Ser. No. 09/704,276, filed Nov. 1, 2000, entitled GLAUCOMA TREATMENT DEVICE, now U.S. Pat. No. 6,736,791, disclose devices and methods of placing a trabecular shunt ab interno, i.e., from inside the anterior chamber through the trabecular meshwork, into Schlemm's canal. The entire contents of each of these patent applications are hereby incorporated by reference herein. The invention encompasses both ab interno and ab externo glaucoma shunts or stents and methods thereof.

Techniques performed in accordance with aspects herein may be referred to generally as "trabecular bypass surgery." Advantages of this type of surgery include lowering intraocular pressure in a manner which is simple, effective, disease site-specific, and can potentially be performed on an outpatient basis.

Generally, trabecular bypass surgery (TBS) creates an opening, a slit, or a hole through trabecular meshwork with minor microsurgery. TBS has the advantage of a much lower risk of choroidal hemorrhage and infection than prior techniques, and it uses existing physiologic outflow mechanisms. In some aspects, this surgery can potentially be performed under topical or local anesthesia on an outpatient basis with rapid visual recovery. To prevent "filling in" of the hole, a biocompatible elongated device is placed within the hole and serves as a stent. U.S. patent application Ser. No. 09/549,350, filed Apr. 14, 2000, now U.S. Pat. No. 6,638,239, the entire contents of which are hereby incorporated by reference herein, discloses trabecular bypass surgery.

As described in U.S. patent application Ser. No. 09/549,350, filed Apr. 14, 2000, now U.S. Pat. No. 6,638,239, and U.S. application Ser. No. 09/704,276, filed Nov. 1, 2000, now U.S. Pat. No. 6,736,791, the entire contents each one of which are hereby incorporated by reference herein, a trabecular shunt or stent for transporting aqueous humor is provided. The trabecular stent includes a hollow, elongate tubular element, having an inlet section and an outlet section. The outlet section may optionally include two segments or elements, adapted to be positioned and stabilized inside Schlemm's canal. In one embodiment, the device appears as a "T" shaped device.

In one aspect of the invention, a delivery apparatus (or "applicator") is used for placing a trabecular stent through a trabecular meshwork of an eye. Certain embodiments of such a delivery apparatus are disclosed in U.S. application Ser. No. 10/101,548, filed Mar. 18, 2002, entitled APPLICATOR AND METHODS FOR PLACING A TRABECULAR SHUNT FOR GLAUCOMA TREATMENT, published as U.S. Publication No. 2002/0133168 and now abandoned, and U.S. Provisional Application No. 60/276,609, filed Mar. 16, 2001, entitled APPLICATOR AND METHODS FOR PLACING A TRABECULAR SHUNT FOR GLAUCOMA TREATMENT, the entire contents of each one of which are hereby incorporated by reference herein.

The stent has an inlet section and an outlet section. The delivery apparatus includes a handpiece, an elongate tip, a holder and an actuator. The handpiece has a distal end and a proximal end. The elongate tip is connected to the distal end of the handpiece. The elongate tip has a distal portion and is configured to be placed through a corneal incision and into an anterior chamber of the eye. The holder is attached to the distal portion of the elongate tip. The holder is configured to hold and release the inlet section of the trabecular stent. The actuator is on the handpiece and actuates the holder to release the inlet section of the trabecular stent from the holder. When the trabecular stent is deployed from the delivery apparatus into the eye, the outlet section is positioned in substantially opposite directions inside Schlemm's canal. In one embodiment, a deployment mechanism within the delivery apparatus includes a push-pull type plunger.

Some aspects of the invention relate to devices for reducing intraocular pressure by providing outflow of aqueous from an anterior chamber of an eye. The device generally comprises an elongated tubular member and cutting means. The tubular member is adapted for extending through a trabecular meshwork of the eye. The tubular member generally comprises a lumen having an inlet port and an outlet port for providing a flow pathway. The cutting means is mechanically connected to the tubular member for creating an incision in the trabecular meshwork for receiving at least a portion of the tubular member.

In one aspect, a self-trephining glaucoma stent is provided for reducing and/or balancing intraocular pressure in an eye. The stent generally comprises a snorkel and a curved blade. The snorkel generally comprises an upper seat for stabilizing said stent within the eye, a shank and a lumen. The shank is mechanically connected to the seat and is adapted for extending through a trabecular meshwork of the eye. The lumen extends through the snorkel and has at least one inlet flow port and at least one outlet flow port. The blade is mechanically connected to the snorkel. The blade generally comprises a cutting tip proximate a distal-most point of the blade for making an incision in the trabecular meshwork for receiving the shank.

Some aspects of the invention relate to methods of implanting a trabecular stent device in an eye. In one aspect, the device has a snorkel mechanically connected to a blade. The blade is advanced blade through a trabecular meshwork of the eye to cut the trabecular meshwork and form an incision therein. At least a portion of the snorkel is inserted in the incision to implant the device in the eye.

Some aspects provide a self-trephining glaucoma stent and methods thereof which advantageously allow for a "one-step" procedure in which the incision and placement of the stent are accomplished by a single device and operation. This desirably allows for a faster, safer, and less expensive surgical procedure. In any of the embodiments, fiducial markings, indicia, or the like and/or positioning of the stent device in a preloaded applicator may be used for proper orientation and alignment of the device during implantation.

Among the advantages of trabecular bypass surgery is its simplicity. The microsurgery may potentially be performed on an outpatient basis with rapid visual recovery and greatly decreased morbidity. There is a lower risk of infection and choroidal hemorrhage, and there is a faster recovery, than with previous techniques.

For purposes of summarizing the invention, certain aspects, advantages and novel features of the invention have been described herein above. Of course, it is to be understood that not necessarily all such advantages may be achieved in accordance with any particular embodiment of the invention. Thus, the invention may be embodied or carried out in a manner that achieves or optimizes one advantage or group of advantages as taught or suggested herein without necessarily achieving other advantages as may be taught or suggested herein.

All of these embodiments are intended to be within the scope of the invention herein disclosed. These and other embodiments of the invention will become readily apparent to those skilled in the art from the following detailed description of the preferred embodiments having reference to the attached figures, the invention not being limited to any particular preferred embodiment(s) disclosed.

BRIEF DESCRIPTION OF THE DRAWINGS

Having thus summarized the general nature of the invention and some of its features and advantages, certain preferred embodiments and modifications thereof will become apparent to those skilled in the art from the detailed description herein having reference to the figures that follow, of which:

FIG. 4 is a side elevation view of the stent of FIG. 3;

FIG. 5 is a top plan view of the stent of FIG. 3;

FIG. 6 is a bottom plan view of the stent of FIG. 3;

FIG. 7 is a front end view of the stent of FIG. 3 (along line 7-7 of FIG. 4);

FIG. 8 is a rear end view of the stent of FIG. 3 (along line 8-8 of FIG. 4);

FIG. 16 is a side elevation view of a glaucoma stent having features and advantages in accordance with one embodiment of the invention;

FIG. 17 is a top plan view of the stent of FIG. 16;

FIG. 18 is a bottom plan view of the stent of FIG. 16;

FIG. 19 is a front end view along line 19-19 of FIG. 16;

FIG. 20 is a rear end view along line 20-20 of FIG. 16;

FIG. 21 is a side elevation view of a glaucoma stent having features and advantages in accordance with one embodiment of the invention;

FIG. 22 is a top plan view of the stent of FIG. 21;

FIG. 23 is a bottom plan view of the stent of FIG. 21;

FIG. 24 is a front end view along line 24-24 of FIG. 21;

FIG. 25 is a rear end view along line 25-25 of FIG. 21;

FIG. 26 is a front elevation view of a glaucoma stent having features and advantages in accordance with one embodiment of the invention;

FIG. 27 is a side elevation view along line 27-27 of FIG. 26;

FIG. 28 is a rear end view along line 28-28 of FIG. 26;

FIGS. 49A and 49B are schematic cross sections of a trabecular punch device.

DETAILED DESCRIPTION OF THE PREFERRED EMBODIMENTS

The preferred embodiments of the invention described herein relate particularly to surgical and therapeutic treatment of glaucoma through reduction of intraocular pressure. While the description sets forth various embodiment specific details, it will be appreciated that the description is illustrative only and should not be construed in any way as limiting the invention. Furthermore, various applications of the invention, and modifications thereto, which may occur to those who are skilled in the art, are also encompassed by the general concepts described herein.

Figure 1:
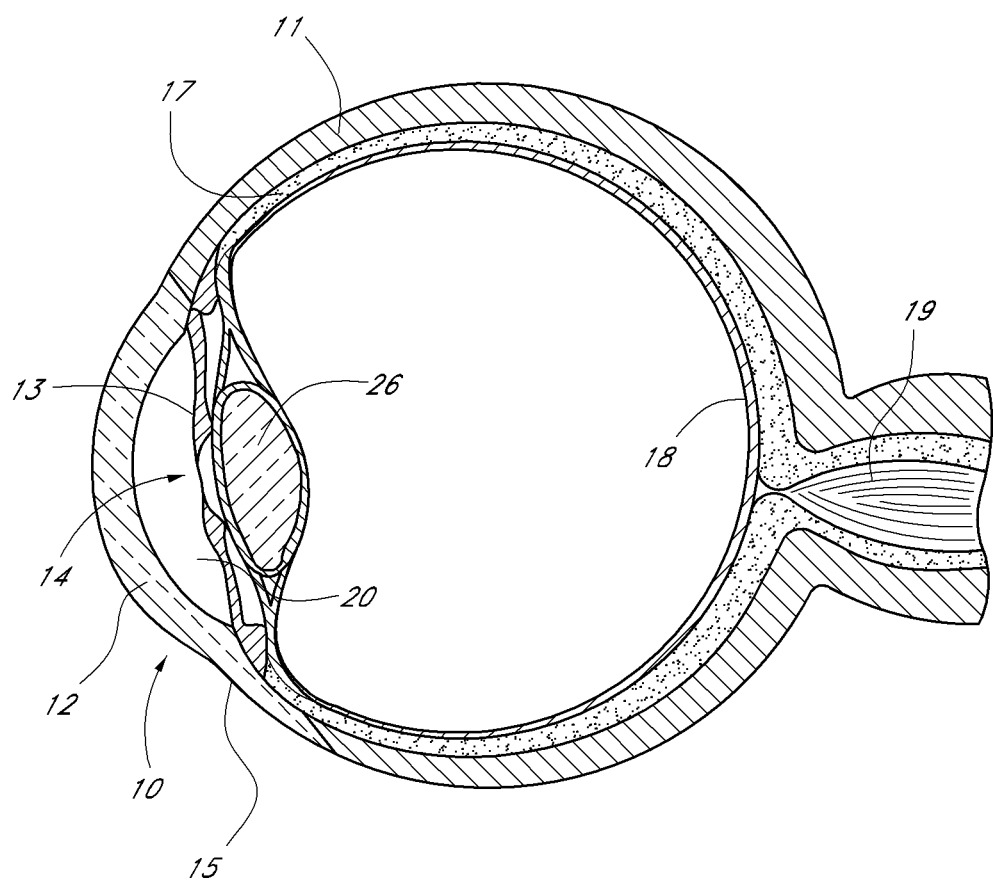
FIG. 1 is a coronal cross-sectional view of an eye.
Figure 2:
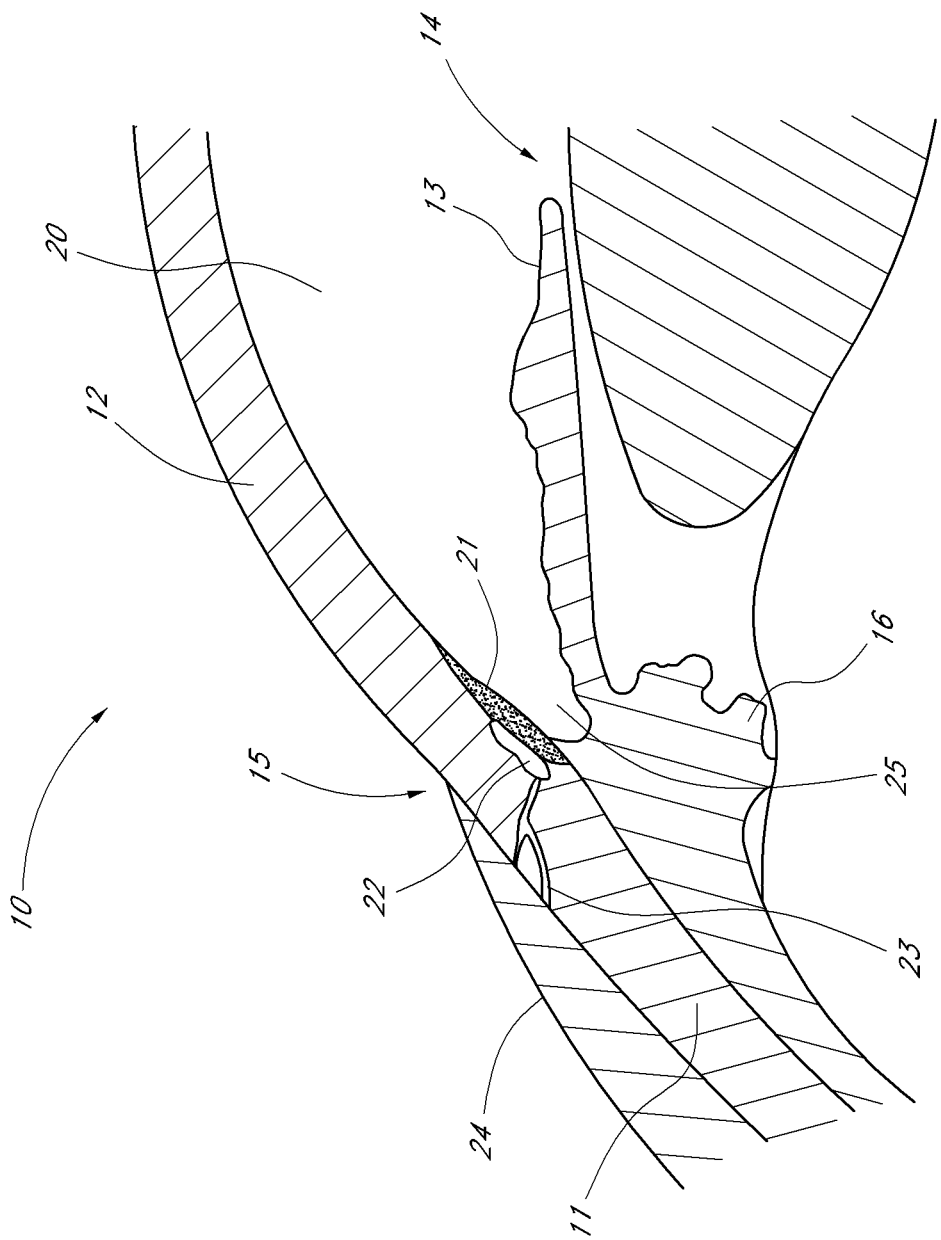
FIG. 2 is an enlarged cross-sectional view of an anterior chamber angle of the eye of FIG. 1.

FIG. 1 is a cross-sectional view of an eye 10, while FIG. 2 is a close-up view showing the relative anatomical locations of a trabecular meshwork 21, an anterior chamber 20, and a Schlemm's canal 22. A sclera 11 is a thick collagenous tissue which covers the entire eye 10 except a portion which is covered by a cornea 12.

Referring to FIGS. 1 and 2, the cornea 12 is a thin transparent tissue that focuses and transmits light into the eye and through a pupil 14, which is a circular hole in the center of an iris 13 (colored portion of the eye). The cornea 12 merges into the sclera 11 at a juncture referred to as a limbus 15. A ciliary body 16 extends along the interior of the sclera 11 and is coextensive with a choroid 17. The choroid 17 is a vascular layer of the eye 10, located between the sclera 11 and a retina 18. An optic nerve 19 transmits visual information to the brain and is the anatomic structure that is progressively destroyed by glaucoma.

Still referring to FIGS. 1 and 2, the anterior chamber 20 of the eye 10, which is bound anteriorly by the cornea 12 and posteriorly by the iris 13 and a lens 26, is filled with aqueous humor (hereinafter referred to as "aqueous"). Aqueous is produced primarily by the ciliary body 16, then moves anteriorly through the pupil 14 and reaches an anterior chamber angle 25, formed between the iris 13 and the cornea 12.

As best illustrated by the drawing of FIG. 2, in a normal eye, aqueous is removed from the anterior chamber 20 through the trabecular meshwork 21. Aqueous passes through the trabecular meshwork 21 into Schlemm's canal 22 and thereafter through a plurality of aqueous veins 23, which merge with blood-carrying veins, and into systemic venous circulation. Intraocular pressure is maintained by an intricate balance between secretion and outflow of aqueous in the manner described above. Glaucoma is, in most cases, characterized by an excessive buildup of aqueous in the anterior chamber 20 which leads to an increase in intraocular pressure. Fluids are relatively incompressible, and thus intraocular pressure is distributed relatively uniformly throughout the eye 10.

As shown in FIG. 2, the trabecular meshwork 21 is adjacent a small portion of the sclera 11. Exterior to the sclera 11 is a conjunctiva 24. Traditional procedures that create a hole or opening for implanting a device through the tissues of the conjunctiva 24 and sclera 11 involve extensive surgery, as compared to surgery for implanting a device, as described herein, which ultimately resides entirely within the confines of the sclera 11 and cornea 12.

Self-Trephining Glaucoma Stent

Figure 3:
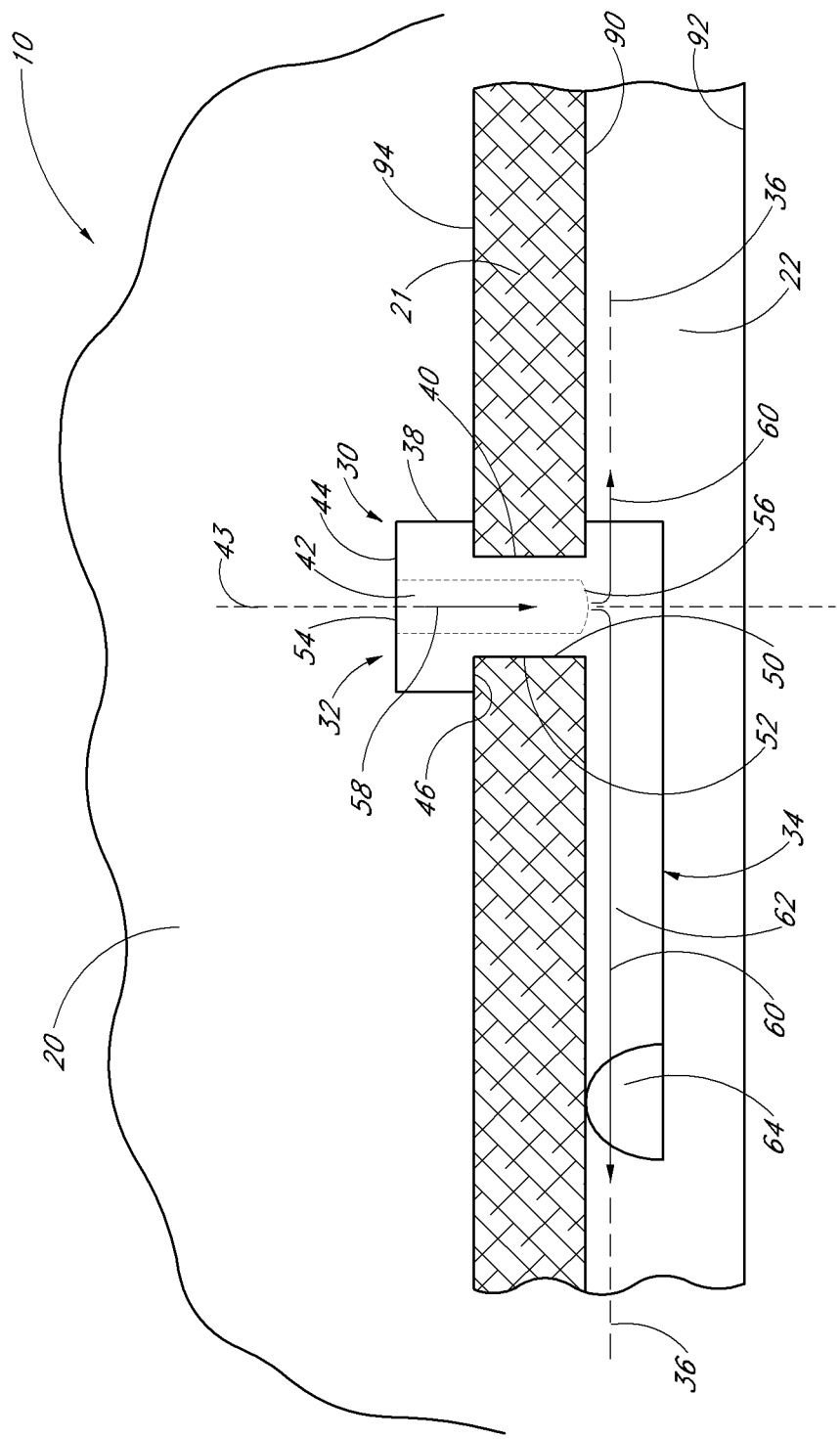
FIG. 3 is a simplified partial view of an eye illustrating the implantation of a glaucoma stent having features and advantages in accordance with one embodiment of the invention.

FIG. 3 generally illustrates the use of one embodiment of a trabecular stenting device 30 for establishing an outflow pathway, passing through the trabecular meshwork 21, which is discussed in greater detail below. FIGS. 4-9 are different views of the stent 30. Advantageously, and as discussed in further detail later herein, the self-trephining-stent allows a one-step procedure to make an incision in the trabecular mesh 21 and place the stent or implant 30 at the desired or predetermined position within the eye 10. Desirably, this facilitates the overall surgical procedure.

In the illustrated embodiment of FIGS. 3-9, the shunt or stent 30 generally comprises a snorkel 32 and a main body portion or blade 34. The snorkel 32 and blade 34 are mechanically connected to or in mechanical communication with one another. The stent 30 and/or the body portion 34 have a generally longitudinal axis 36.

In the illustrated embodiment of FIGS. 3-9, the stent 30 comprises an integral unit. In modified embodiments, the stent 30 may comprise an assembly of individual pieces or components. For example, the stent 30 may comprise an assembly of the snorkel 32 and blade 34.

In the illustrated embodiment of FIGS. 3-9, the snorkel 32 is in the form of a generally elongate tubular member and generally comprises an upper seat, head or cap portion 38, a shank portion 40 and a lumen or passage 42 extending therethrough. The seat 38 is mechanically connected to or in mechanical communication with the shank 40 which is also mechanically connected to or in mechanical communication with the blade 34. The snorkel 32 and/or the lumen 42 have a generally longitudinal axis 43.

In the illustrated embodiment of FIGS. 3-9, the seat 38 is generally circular in shape and has an upper surface 44 and a lower surface 46 which, as shown in FIG. 3, abuts or rests against the trabecular meshwork 21 to stabilize the glaucoma stent 30 within the eye 10. In modified embodiments, the seat 38 may efficaciously be shaped in other suitable manners, as required or desired, giving due consideration to the goals of stabilizing the glaucoma stent 30 within the eye 10 and/or of achieving one or more of the benefits and advantages as taught or suggested herein. For example, the seat 38 may be shaped in other polygonal or non-polygonal shapes and/or comprise one or more ridges which extend radially outwards, among other suitable retention devices.

Figure 10:
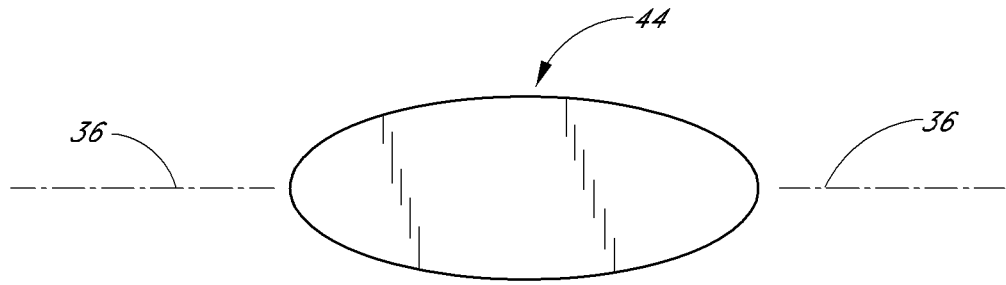
FIG. 10 is a top plan view of one exemplary embodiment of a snorkel top seating surface.
Figure 11:
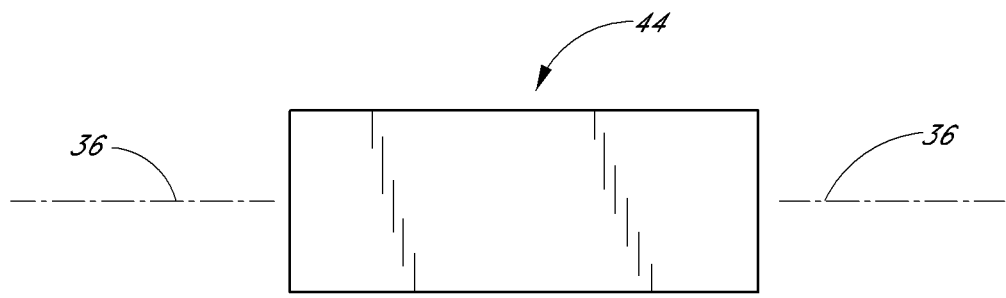
FIG. 11 is a top plan view of another exemplary embodiment of a snorkel top seating surface.
Figure 12:
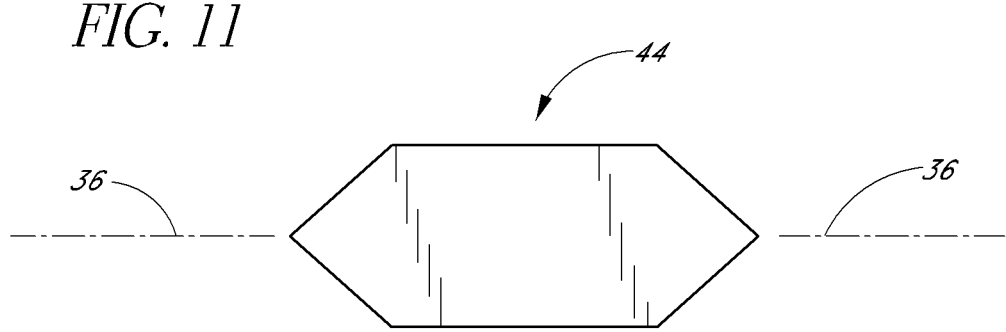
FIG. 12 is a top plan view of yet another exemplary embodiment of a snorkel top seating surface.
Figure 13:
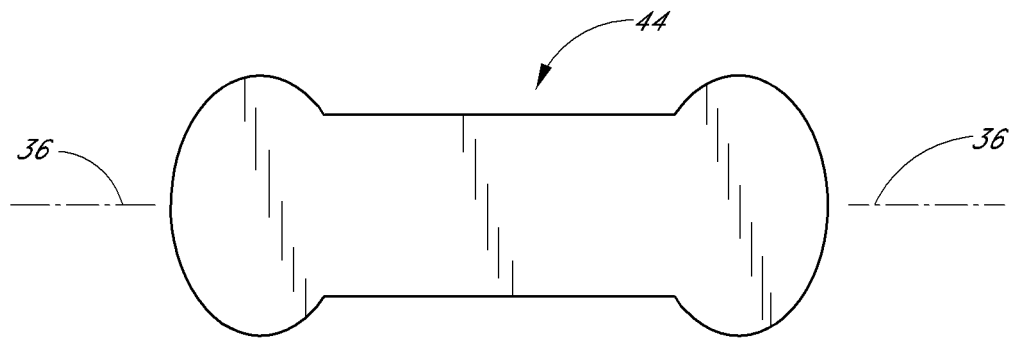
FIG. 13 is a top plan view of still another exemplary embodiment of a snorkel top seating surface.

In the illustrated embodiment of FIGS. 3-9, and as best seen in the top view of FIG. 5, the seat top surface 44 comprises fiducial marks or indicia 48. These marks or indicia 48 facilitate and ensure proper orientation and alignment of the stent 30 when implanted in the eye 10. The marks or indicia 48 may comprise visual differentiation means such as color contrast or be in the form of ribs, grooves, or the like. Alternatively, or in addition, the marks 48 may provide tactile sensory feedback to the surgeon. Also, the seat 38 and/or the seat top surface 44 may be configured in predetermined shapes aligned with the blade 34 and/or longitudinal axis 36 to provide for proper orientation of the stent device 30 within the eye 10. For example, the seat top surface 44 may be oval or ellipsoidal (FIG. 10), rectangular (FIG. 11), hexagonal (FIG. 12), among other suitable shapes (e.g. FIG. 13).

In the illustrated embodiment of FIGS. 3-9, and as indicated above, the seat bottom surface 46 abuts or rests against the trabecular meshwork 21 to stabilize and retain the glaucoma stent 30 within the eye 10. For stabilization purposes, the seat bottom surface 46 may comprise a studded surface, a ribbed surface, a surface with pillars, a textured surface, or the like.

In the illustrated embodiment of FIGS. 3-9, the snorkel shank 40 is generally cylindrical in shape. With the stent 30 implanted, as shown in FIG. 3, the shank 40 is generally positioned in an incision or cavity 50 formed in the trabecular meshwork 21 by the self-trephining stent 30. Advantageously, and as discussed further below, this single step of forming the cavity 50 by the stent 30 itself and placing the stent 30 in the desired position facilitates and expedites the overall surgical procedure. In modified embodiments, the snorkel shank 40 may efficaciously be shaped in other suitable manners, as required or desired. For example, the shank 40 may be in the shape of other polygonal or non-polygonal shapes, such as, oval, elliposoidal, and the like.

In the illustrated embodiment of FIGS. 3-9, and as best seen in FIG. 3, the shank 40 has an outer surface 52 in contact with the trabecular meshwork 21 surrounding the cavity 50. For stabilization purposes, the shank outer surface 52 may comprise a studded surface, a ribbed surface, a surface with pillars, a textured surface, or the like.

In the illustrated embodiment of FIGS. 3-9, the snorkel lumen 42 has an inlet port, opening or orifice 54 at the seat top surface 44 and an outlet port, opening or orifice 56 at the junction of the shank 40 and blade 34. The lumen 42 is generally cylindrical in shape, that is, it has a generally circular cross-section, and its ports 54, 56 are generally circular in shape. In modified embodiments, the lumen 42 and ports 54, 56 may be efficaciously shaped in other manners, as required or desired, giving due consideration to the goals of providing sufficient aqueous outflow and/or of achieving one or more of the benefits and advantages as taught or suggested herein. For example, the lumen 42 and/or one or both ports 54, 56 may be shaped in the form of ovals, ellipsoids, and the like, or the lumen 42 may have a tapered or stepped configuration.

Referring in particular to FIG. 3, aqueous from the anterior chamber 20 flows into the lumen 42 through the inlet port 54 (as generally indicated by arrow 58) and out of the outlet port 56 and into Schlemm's canal 22 (as generally indicated by arrows 60) to lower and/or balance the intraocular pressure (IOP). In another embodiment, as discussed in further detail below, one or more of the outlet ports may be configured to face in the general direction of the stent longitudinal axis 36. In modified embodiments, the snorkel 32 may comprise more than one lumen, as needed or desired, to facilitate multiple aqueous outflow transportation into Schlemm's canal 22.

In the illustrated embodiment of FIGS. 3-9, the blade longitudinal axis 36 and the snorkel longitudinal axis 43 are generally perpendicular to one another. Stated differently, the projections of the axes 36, 43 on a common plane which is not perpendicular to either of the axes 36, 43 intersect at 90°. The blade longitudinal axis 36 and the snorkel longitudinal axis 43 may intersect one another or may be offset from one another.

In the illustrated embodiment of FIGS. 3-9, the main body portion or blade 34 is a generally curved elongated sheet- or plate-like structure with an upper curved surface 62 and a lower curved surface 64 which defines a trough or open face channel 66. The perimeter of the blade 34 is generally defined by a curved proximal edge 68 proximate to the snorkel 32, a curved distal edge 70 spaced from the proximal edge 68 by a pair of generally straight lateral edges 72, 74 with the first lateral edge 72 extending beyond the second lateral edge 74 and intersecting with the distal edge 70 at a distal-most point 76 of the blade 34 proximate a blade cutting tip 78.

Figure 9:
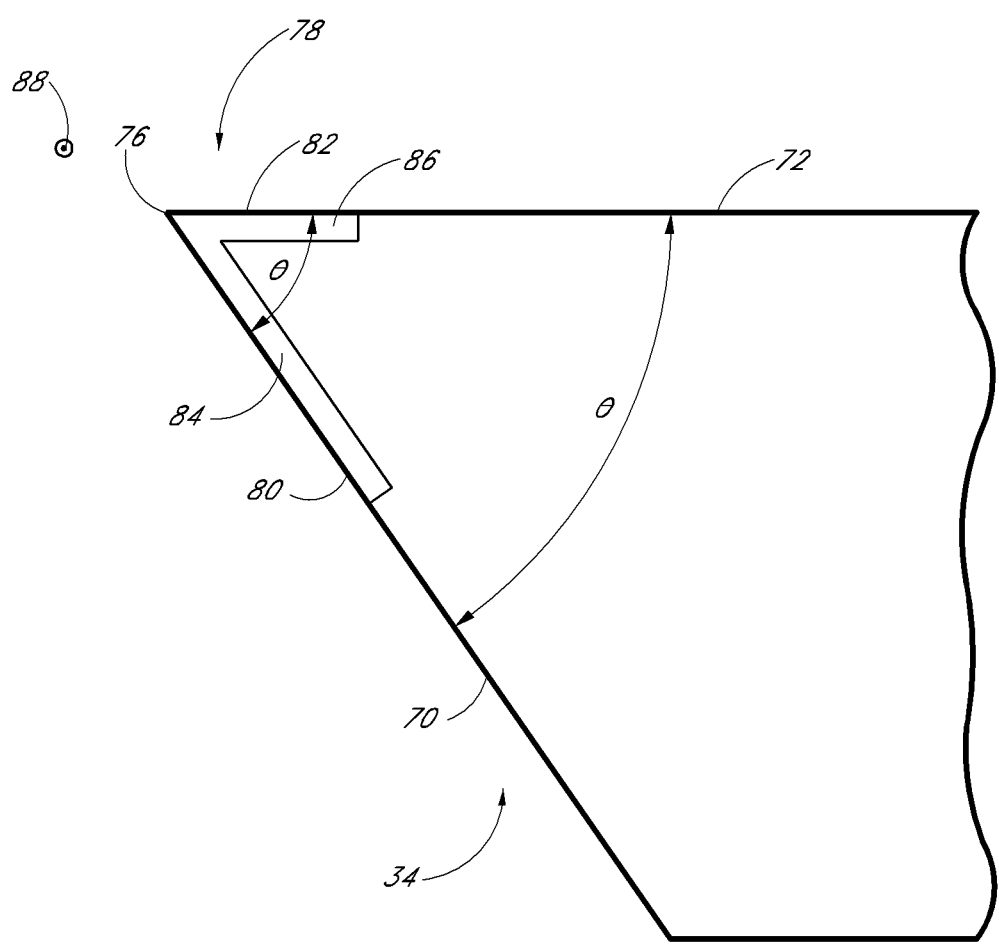
FIG. 9 is an enlarged top plan view of a cutting tip of the stent of FIG. 3.

In the illustrated embodiment of FIGS. 3-9, and as shown in the enlarged view of FIG. 9, the cutting tip 78 comprises a first cutting edge 80 on the distal edge 70 and a second cutting edge 82 on the lateral edge 72. The cutting edges 80, 82 preferably extend from the distal-most point 76 of the blade 34 and comprise at least a respective portion of the distal edge 70 and lateral edge 72. The respective cutting edges 80, 82 are formed at the sharp edges of respective beveled or tapered surfaces 84, 86. In one embodiment, the remainder of the distal edge 70 and lateral edge 72 are dull or rounded. In one embodiment, the tip 78 proximate to the distal-most end 76 is curved slightly inwards, as indicated generally by the arrow 88 in FIG. 5 and arrow 88 (pointed perpendicular and into the plane of the paper) in FIG. 9, relative to the adjacent curvature of the blade 34.

In modified embodiments, suitable cutting edges may be provided on selected portions of one or more selected blade edges 68, 70, 72, 74 with efficacy, as needed or desired, giving due consideration to the goals of providing suitable cutting means on the stent 30 for effectively cutting through the trabecular meshwork 21 (FIG. 3) and/or of achieving one or more of the benefits and advantages as taught or suggested herein.

Referring in particular to FIG. 9, in one embodiment, the ratio between the lengths of the cutting edges 80, 82 is about 2:1. In another embodiment, the ratio between the lengths of the cutting edges 80, 82 is about 1:1. In yet another embodiment, the ratio between the lengths of the cutting edges 80, 82 is about 1:2. In modified embodiments, the lengths of the cutting edges 80, 82 may be efficaciously selected in other manners, as required or desired, giving due consideration to the goals of providing suitable cutting means on the stent 30 for effectively cutting through the trabecular meshwork 21 (FIG. 3) and/or of achieving one or more of the benefits and advantages as taught or suggested herein.

Still referring in particular to FIG. 9, in one embodiment, the ratio between the lengths of the cutting edges 80, 82 is in the range from about 2:1 to about 1:2. In another embodiment, the ratio between the lengths of the cutting edges 80, 82 is in the range from about 5:1 to about 1:5. In yet another embodiment, the ratio between the lengths of the cutting edges 80, 82 is in the range from about 10:1 to about 1:10. In modified embodiments, the lengths of the cutting edges 80, 82 may be efficaciously selected in other manners, as required or desired, giving due consideration to the goals of providing suitable cutting means on the stent 30 for effectively cutting through the trabecular meshwork 21 (FIG. 3) and/or of achieving one or more of the benefits and advantages as taught or suggested herein.

As shown in the top view of FIG. 9, the cutting edge 80 (and/or the distal end 70) and the cutting edge 82 (and/or the lateral edge 72) intersect at an angle θ. Stated differently, θ is the angle between the projections of the cutting edge 80 (and/or the distal end 70) and the cutting edge 82 (and/or the lateral edge 72) on a common plane which is not perpendicular to either of these edges.

Referring to in particular to FIG. 9, in one embodiment, the angle θ is about 50°. In another embodiment, the angle θ is in the range from about 40° to about 60°. In yet another embodiment, the angle θ is in the range from about 30° to about 70°. In modified embodiments, the angle θ may be efficaciously selected in other manners, as required or desired, giving due consideration to the goals of providing suitable cutting means on the stent 30 for effectively cutting through the trabecular meshwork 21 (FIG. 3) and/or of achieving one or more of the benefits and advantages as taught or suggested herein.

The stent 30 of the embodiments disclosed herein can be dimensioned in a wide variety of manners. Referring in particular to FIG. 3, the depth of Schlemm's canal 22 is typically about less than 400 microns (μm). Accordingly, the stent blade 34 is dimensioned so that the height of the blade 34 (referred to as $H_{41}$ in FIG. 4) is typically less than about 400 μm. The snorkel shank 40 is dimensioned so that it has a length (referred to as $L_{41}$ in FIG. 4) typically in the range from about 100 μm to about 300 μm which is roughly the typical range of the thickness of the trabecular meshwork 21.

Of course, as the skilled artisan will appreciate, that with the stent 30 implanted, the blade 34 may rest at any suitable position within Schlemm's canal 22. For example, the blade 34 may be adjacent to a front wall 90 of Schlemm's canal 22 (as shown in FIG. 3), or adjacent to a back wall 92 of Schlemm's canal 22, or at some intermediate location therebetween, as needed or desired. Also, the snorkel shank 40 may extend into Schlemm's canal 22. The length of the snorkel shank 40 and/or the dimensions of the blade 34 may be efficaciously adjusted to achieve the desired implant positioning.

The trabecular stenting device 30 (FIGS. 3-9) of the exemplary embodiment may be manufactured or fabricated by a wide variety of techniques. These include, without limitation, by molding, thermo-forming, or other micromachining techniques, among other suitable techniques.

The trabecular stenting device 30 preferably comprises a biocompatible material such that inflammation arising due to irritation between the outer surface of the device 30 and the surrounding tissue is minimized. Biocompatible materials which may be used for the device 30 preferably include, but are not limited to, titanium, titanium alloys, medical grade silicone, e.g., Silastic™, available from Dow Corning Corporation of Midland, Mich.; and polyurethane, e.g., Pellethane™, also available from Dow Corning Corporation.

In other embodiments, the stent device 30 may comprise other types of biocompatible material, such as, by way of example, polyvinyl alcohol, polyvinyl pyrolidone, collagen, heparinized collagen, polytetrafluoroethylene, expanded polytetrafluoroethylene, fluorinated polymer, fluorinated elastomer, flexible fused silica, polyolefin, polyester, polysilicon, and/or a mixture of the aforementioned biocompatible materials, and the like. In still other embodiments, composite biocompatible material may be used, wherein a surface material may be used in addition to one or more of the aforementioned materials. For example, such a surface material may include polytetrafluoroethylene (PTFE) (such as Teflon™), polyimide, hydrogel, heparin, therapeutic drugs (such as beta-adrenergic antagonists and other antiglaucoma drugs, or antibiotics), and the like.

In an exemplary embodiment of the trabecular meshwork surgery, the patient is placed in the supine position, prepped, draped and anesthetized as necessary. In one embodiment, a small (less than about 1 mm) incision, which may be self-sealing is made through the cornea 12. The corneal incision can be made in a number of ways, for example, by using a micro-knife, among other tools.

An applicator or delivery apparatus is used to advance the glaucoma stent 30 through the corneal incision and to the trabecular meshwork 21. Some embodiments of such a delivery apparatus are disclosed in U.S. application Ser. No. 10/101,548, filed Mar. 18, 2002, entitled APPLICATOR AND METHODS FOR PLACING A TRABECULAR SHUNT FOR GLAUCOMA TREATMENT, published as U.S. Publication No. 2002/0133168 and now abandoned, and U.S. Provisional Application No. 60/276,609, filed Mar. 16, 2001, entitled APPLICATOR AND METHODS FOR PLACING A TRABECULAR SHUNT FOR GLAUCOMA TREATMENT, the entire contents of each one of which are hereby incorporated by reference herein. Some embodiments of a delivery apparatus are also discussed in further detail later herein. Gonioscopic, microscopic, or endoscopic guidance may be used during the trabecular meshwork surgery.

With the device 30 held by the delivery apparatus, the blade 34 of the self-trephining glaucoma stent device 30 is used to cut and/or displace the material of the trabecular meshwork 21. The snorkel shank 40 may also facilitate in removal of this material during implantation. The delivery apparatus is withdrawn once the device 30 has been implanted in the eye 10. As shown in FIG. 3, once proper implantation has been accomplished the snorkel seat 38 rests on a top surface 94 of the trabecular meshwork 21, the snorkel shank 40 extends through the cavity 50 (created by the device 30) in the trabecular meshwork 21, and the blade extends inside Schlemm's canal 22.

Advantageously, the embodiments of the self-trephining stent device of the invention allow for a "one-step" procedure to make an incision in the trabecular meshwork and to subsequently implant the stent in the proper orientation and alignment within the eye to allow outflow of aqueous from the anterior chamber through the stent and into Schlemm's canal to lower and/or balance the intraocular pressure (IOP). Desirably, this provides for a faster, safer, and less expensive surgical procedure.

Many complications can arise in trabecular meshwork surgeries, wherein a knife is first used to create an incision in the trabecular meshwork, followed by removal of the knife and subsequent installation of the stent. For instance, the knife may cause some bleeding which clouds up the surgical site. This may require more effort and time to clean the surgical site prior to placement of the stent. Moreover, this may cause the intraocular pressure (IOP) to rise. Thus, undesirably, such a multiple step procedure may demand crisis management which slows down the surgery, makes it less safe, and more expensive.

Figure 14:
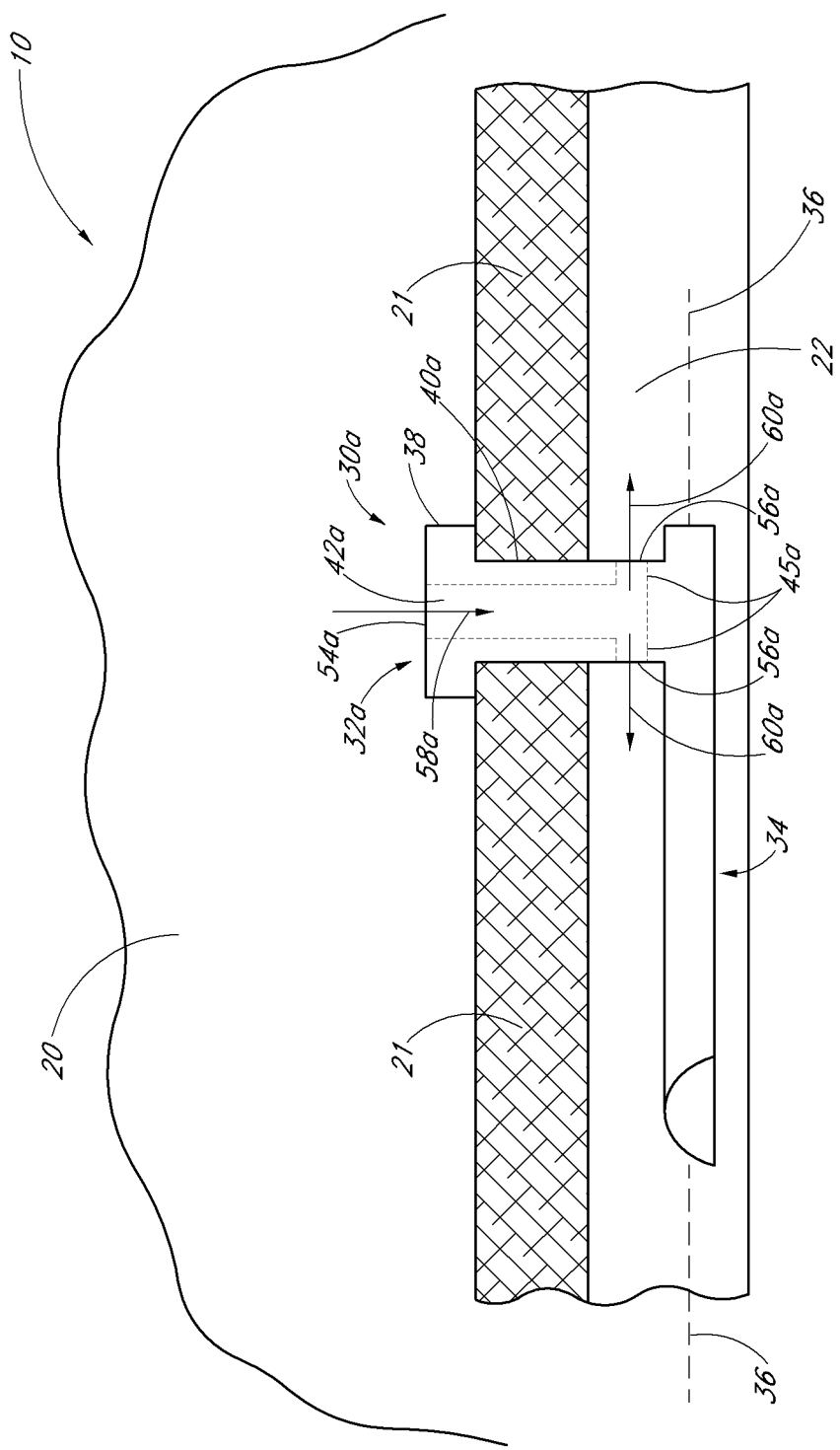
FIG. 14 is a simplified partial view of an eye illustrating the implantation of a glaucoma stent having features and advantages in accordance with another embodiment of the invention.

FIG. 14 is a simplified partial view of an eye 10 illustrating the implantation of a self-trephining glaucoma stent device 30a having features and advantages in accordance with one embodiment. The stent 30a is generally similar to the stent 30 of FIGS. 3-9 except that its snorkel 32a comprises a longer shank 40a which extends into Schlemm's canal 22 and a lumen 42a which bifurcates into two output channels 45a.

In the illustrated embodiment of FIG. 14, the shank 40a terminates at the blade 34. Aqueous flows from the anterior chamber 20 into the lumen 42a through an inlet port 54a (as generally indicated by arrow 58a). Aqueous then flows through the output channels 45a and out of respective outlet ports 56a and into Schlemm's canal 22 (as generally indicated by arrows 60a). The outlet channels 45a extend radially outwards in generally opposed directions and the outlet ports 56a are configured to face in the general direction of the stent longitudinal axis 36 so that they open into Schlemm's canal 22 and are in proper orientation to allow aqueous outflow into Schlemm's canal 22 for lowering and/or balancing the intraocular pressure (IOP). As indicated above, fiducial marks or indicia and/or predetermined shapes of the snorkel seat 38 allow for proper orientation of the blade 34 and also the output channels 45a and respective ports 56a within Schlemm's canal.

In the illustrated embodiment of FIG. 14, two outflow channels 45a are provided. In another embodiment, only one outflow channel 45a is provided. In yet another embodiment, more than two outflow channels 45a are provided. In modified embodiments, the lumen 42a may extend all the way through to the blade 34 and provide an outlet port as discussed above with reference to the embodiment of FIGS. 3-9.

Figure 15:
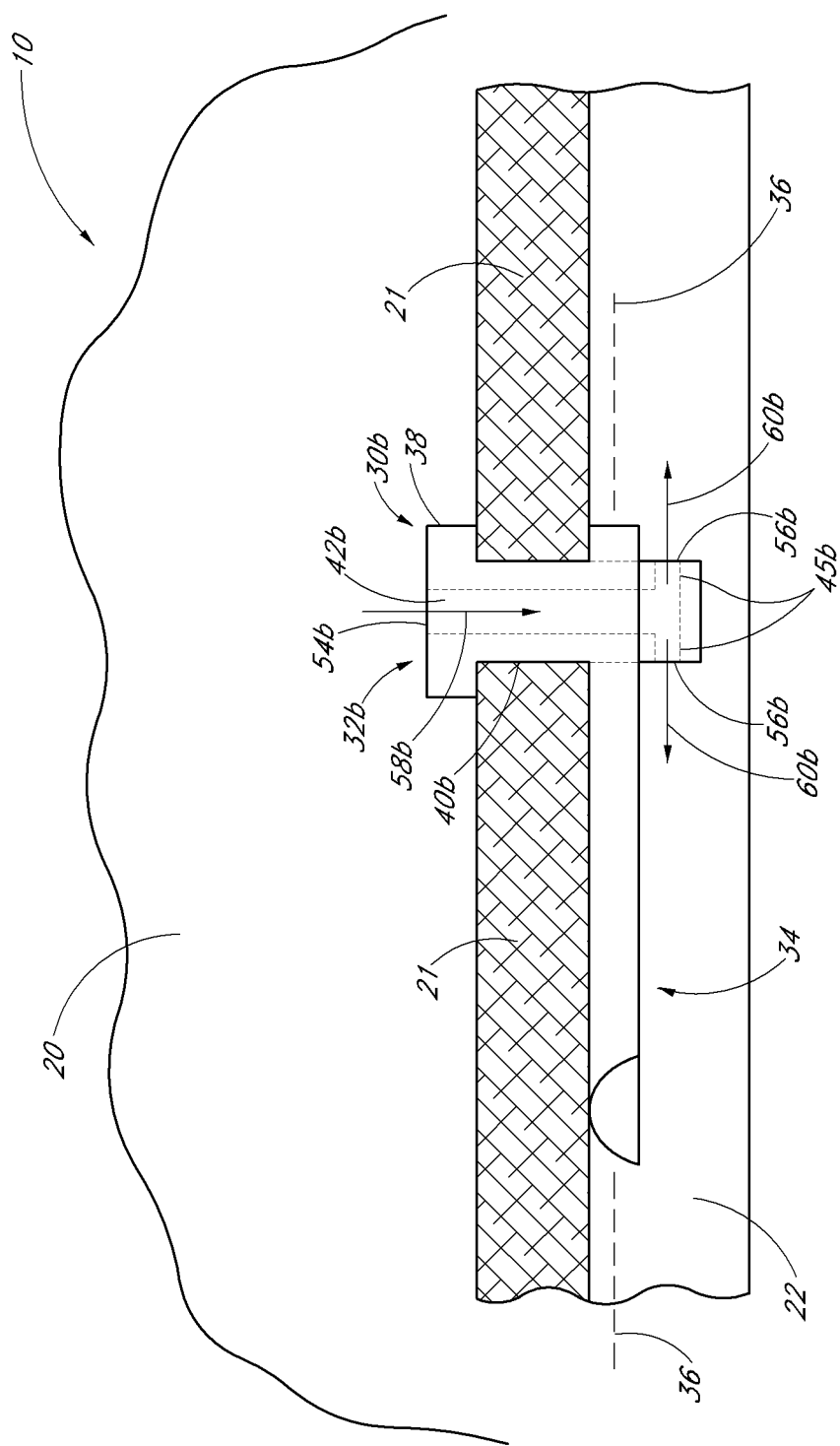
FIG. 15 is a simplified partial view of an eye illustrating the implantation of a glaucoma stent having features and advantages in accordance with a further embodiment of the invention.

FIG. 15 is a simplified partial view of an eye 10 illustrating the implantation of a self-trephining glaucoma stent device 30b having features and advantages in accordance with one embodiment. The stent 30b is generally similar to the stent 30 of FIGS. 3-9 except that its snorkel 32b comprises a longer shank 40*b* which extends into Schlemm's canal 22 and a lumen 42*b* which bifurcates into two output channels 45*b*.

In the illustrated embodiment of FIG. 15, the shank 40*b* extends through the blade 34. Aqueous flows from the anterior chamber 20 into the lumen 42*b* through an inlet port 54*b* (as generally indicated by arrow 58*b*). Aqueous then flows through the output channels 45*b* and out of respective outlet ports 56*b* and into Schlemm's canal 22 (as generally indicated by arrows 60*b*). The outlet channels 45*b* extend radially outwards in generally opposed directions and the outlet ports 56*b* are configured to face in the general direction of the stent longitudinal axis 36 so that they open into Schlemm's canal 22 and are in proper orientation to allow aqueous outflow into Schlemm's canal 22 for lowering and/or balancing the intraocular pressure (IOP). As indicated above, fiducial marks or indicia and/or predetermined shapes of the snorkel seat 38 allow for proper orientation of the blade 34 and also the output channels 45*b* and respective ports 56*b* within Schlemm's canal.

In the illustrated embodiment of FIG. 15, two outflow channels 45*b* are provided. In another embodiment, only one outflow channel 45*b* is provided. In yet another embodiment, more than two outflow channels 45*b* are provided. In modified embodiments, the lumen 42*b* may extend all the way through to the blade 34 and provide an outlet port as discussed above with reference to the embodiment of FIGS. 3-9.

FIGS. 16-20 show different views of a self-trephining glaucoma stent device 30*c* having features and advantages in accordance with one embodiment. The stent 30*c* is generally similar to the stent 30 of FIGS. 3-9 except that it has a modified blade configuration. The stent 30*c* comprises a blade 34*c* which is a generally curved elongated sheet- or plate-like structure with an upper curved surface 62*c* and a lower curved surface 64*c* which defines a trough or open face channel 66*c*. The perimeter of the blade 34*c* is generally defined by a curved proximal edge 68*c* proximate to the snorkel 32, a curved distal edge 70*c* spaced from the proximal edge 68*c* by a pair of generally straight lateral edges 72*c*, 74*c* which are generally parallel to one another and have about the same length.

In the illustrated embodiment of FIGS. 16-20, the blade 34*c* comprises a cutting tip 78*c*. The cutting tip 78*c* preferably includes cutting edges formed on selected portions of the distal edge 70*c* and adjacent portions of the lateral edges 72*c*, 74*c* for cutting through the trabecular meshwork for placement of the snorkel 32. The cutting edges are sharp edges of beveled or tapered surfaces as discussed above in reference to FIG. 9. The embodiment of FIGS. 16-20 may be efficaciously modified to incorporate the snorkel configuration of the embodiments of FIGS. 14 and 15.

FIGS. 21-25 show different views of a self-trephining glaucoma stent device 30*d* having features and advantages in accordance with one embodiment. The stent 30*d* is generally similar to the stent 30 of FIGS. 3-9 except that it has a modified blade configuration. The stent 30*d* comprises a blade 34*d* which is a generally curved elongated sheet- or plate-like structure with an upper curved surface 62*d* and a lower curved surface 64*d* which defines a trough or open face channel 66*d*. The perimeter of the blade 34*d* is generally defined by a curved proximal edge 68*d* proximate to the snorkel 32, a pair of inwardly converging curved distal edges 70*d'*, 70*d"* spaced from the proximal edge 68*d* by a pair of generally straight respective lateral edges 72*d*, 74*d* which are generally parallel to one another and have about the same length. The distal edges 70*d'*, 70*d"* intersect at a distal-most point 76*d* of the blade 34*d* proximate a blade cutting tip 78*d*.

In the illustrated embodiment of FIGS. 21-25, the cutting tip 78*d* preferably includes cutting edges formed on the distal edges 70*d'*, 70*d"* and extending from the distal-most point 76*d* of the blade 34*d*. In one embodiment, the cutting edges extend along only a portion of respective distal edges 70*d'*, 70*d"*. In another embodiment, the cutting edges extend along substantially the entire length of respective distal edges 70*d'*, 70*d"*. In yet another embodiment, at least portions of the lateral edges 72*d*, 74*d* proximate to respective distal edges 70*d'*, 70*d"* have cutting edges. In a further embodiment, the tip 78*d* proximate to the distal-most end 76*d* is curved slightly inwards, as indicated generally by the arrow 88*d* in FIG. 21 and arrow 88*d* (pointed perpendicular and into the plane of the paper) in FIG. 22, relative to the adjacent curvature of the blade 34*d*.

In the embodiment of FIGS. 21-25, the cutting edges are sharp edges of beveled or tapered surfaces as discussed above in reference to FIG. 9. The embodiment of FIGS. 21-25 may be efficaciously modified to incorporate the snorkel configuration of the embodiments of FIGS. 14 and 15.

FIGS. 26-28 show different views of a self-trephining glaucoma stent device 30*e* having features and advantages in accordance with one embodiment. The stent device 30*e* generally comprises a snorkel 32*e* mechanically connected to or in mechanical communication with a blade or cutting tip 34*e*. The snorkel 32*e* has a seat, head or cap portion 38*e* mechanically connected to or in mechanical communication with a shank 40*e*, as discussed above. The shank 40*e* has a distal end or base 47*e*. The snorkel 32*e* further has a lumen 42*e* which bifurcates into a pair of outlet channels 45*e*, as discussed above in connection with FIGS. 14 and 15. Other lumen and inlet and outlet port configurations as taught or suggested herein may also be efficaciously used, as needed or desired.

In the illustrated embodiment of FIGS. 26-28, the blade 34*e* extends downwardly and outwardly from the shank distal end 47*e*. The blade 34*e* is angled relative to a generally longitudinal axis 43*e* of the snorkel 32*e*, as best seen in FIGS. 27 and 28. The blade 34*e* has a distal-most point 76*e*. The blade or cutting tip 34*e* has a pair of side edges 70*e'*, 70*e"*, including cutting edges, terminating at the distal-most point 76*e*, as best seen in FIG. 26. In one embodiment, the cutting edges are sharp edges of beveled or tapered surfaces as discussed above in reference to FIG. 9.

Referring to FIGS. 26-28, in one embodiment, the blade 34*e* includes cutting edges formed on the edges 70*e'*, 70*e"* and extending from the distal-most point 76*e* of the blade 34*d*. In one embodiment, the cutting edges extend along only a portion of respective distal edges 70*e'*, 70*e"*. In another embodiment, the cutting edges extend along substantially the entire length of respective distal edges 70*e'*, 70*e"*. In yet another embodiment, the blade or cutting tip 34*e* comprises a bent tip of needle, for example, a 30 gauge needle.

In general, any of the blade configurations disclosed herein may be used in conjunction with any of the snorkel configurations disclosed herein or incorporated by reference herein to provide a self-trephining glaucoma stent device for making an incision in the trabecular meshwork for receiving the corresponding snorkel to provide a pathway for aqueous outflow from the eye anterior chamber to Schlemm's canal, thereby effectively lowering and/or balancing the intraocular pressure (IOP). The self-trephining ability of the device, advantageously, allows for a "one-step" procedure in which the incision and placement of the snorkel are accomplished by a single device and operation. In any of the embodiments, fiducial markings or indicia, and/or preselected configuration of the snorkel seat, and/or positioning of the stent device in a preloaded applicator may be used for proper orientation and alignment of the device during implantation.

Delivery Apparatus

Figure 29:
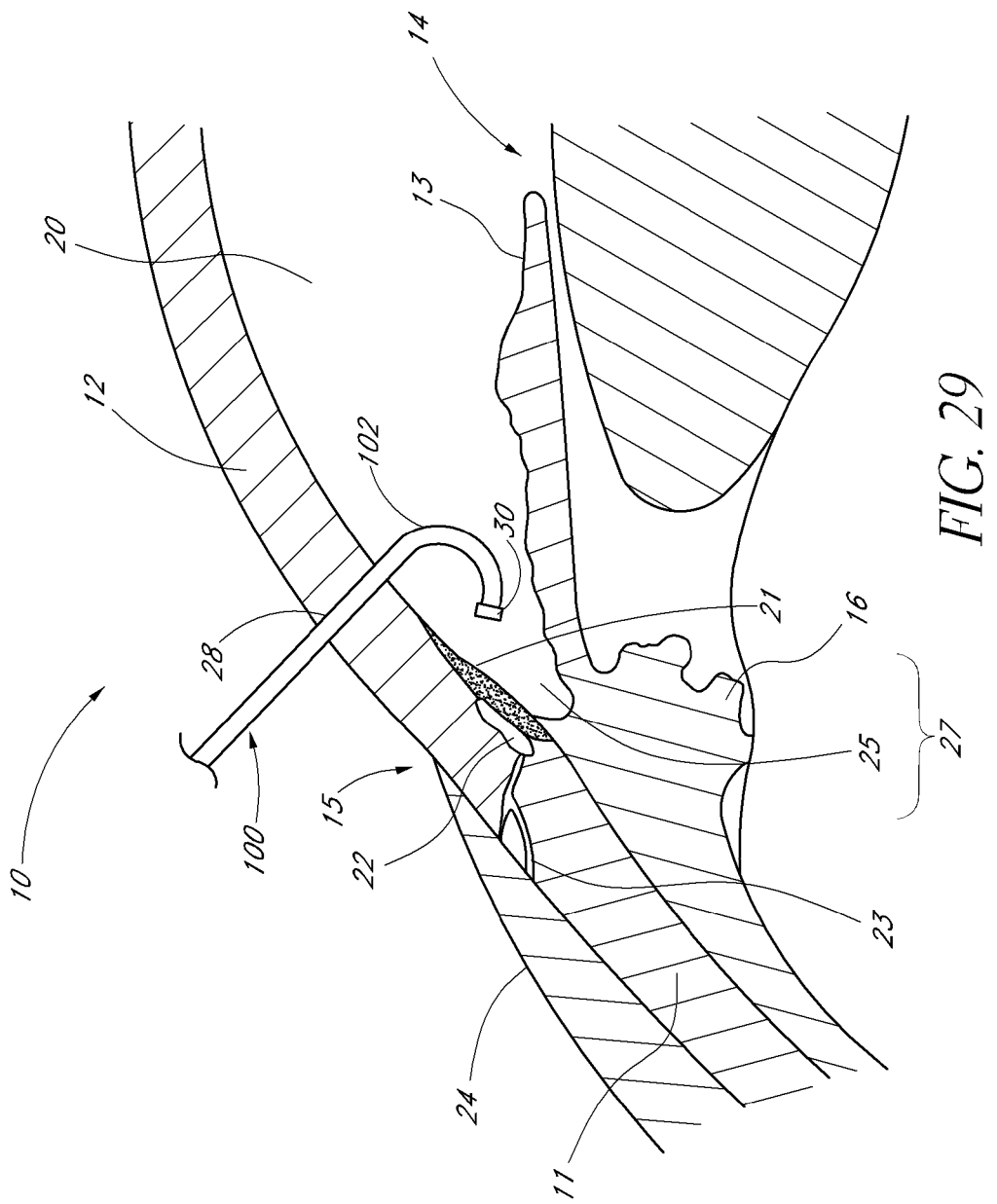
FIG. 29 is a simplified partial view of an eye illustrating the temporal implantation of a glaucoma stent using a delivery apparatus having features and advantages in accordance with one embodiment of the invention.

In many cases, a surgeon works from a temporal incision when performing cataract or goniometry surgery. FIG. 29 illustrates a temporal implant procedure, wherein a delivery apparatus or "applicator" 100 having a curved tip 102 is used to deliver a stent 30 to a temporal side 27 of the eye 10. An incision 28 is made in the cornea 10, as discussed above. The apparatus 100 is then used to introduce the stent 30 through the incision 28 and implant it within the eye 10.

Still referring in particular to FIG. 29, in one embodiment, a similarly curved instrument would be used to make the incision through the trabecular meshwork 21. In other embodiments, a self-trephining stent device 30 may be used to make this incision through the trabecular meshwork 21, as discussed above. The temporal implantation procedure illustrated in FIG. 29 may be employed with the any of the various stent embodiments taught or suggested herein.

Figure 30:
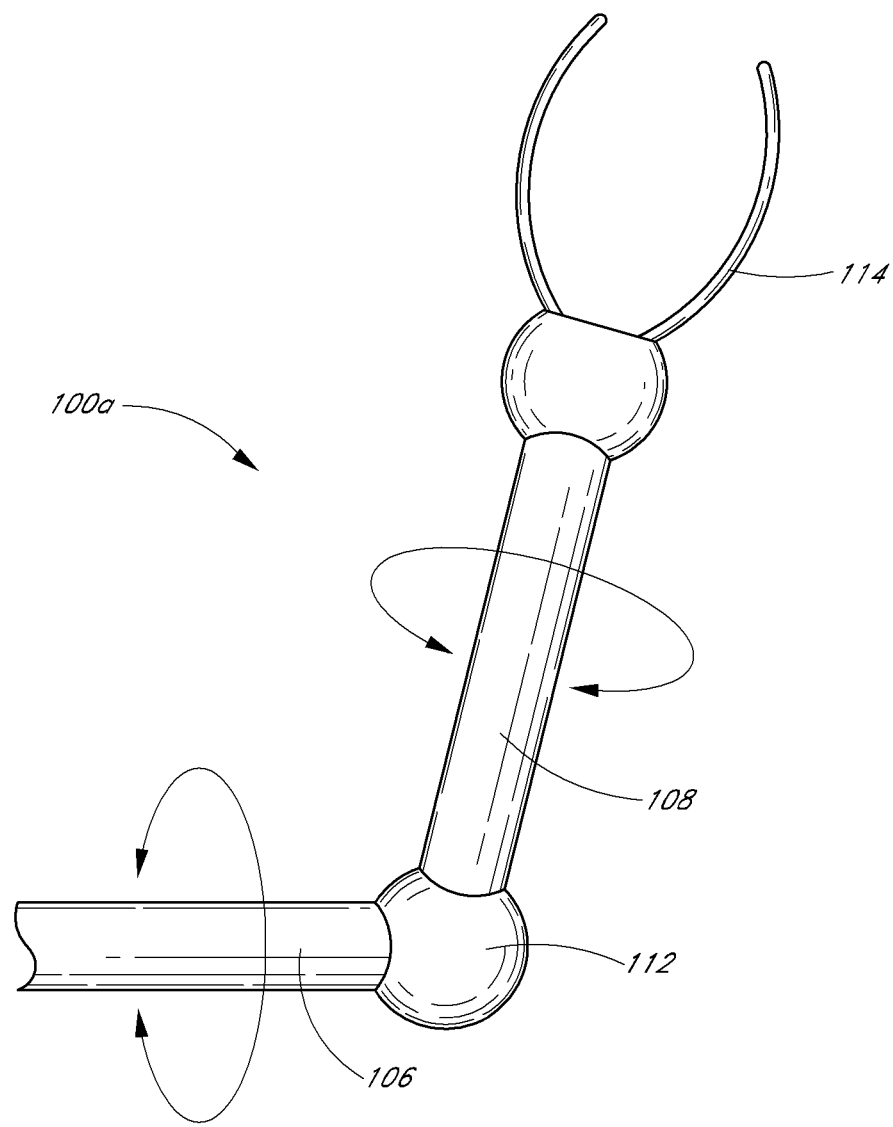
FIG. 30 is an oblique elevational view of an articulating arm stent delivery/retrieval apparatus having features and advantages in accordance with one embodiment of the invention.

FIG. 30 illustrates one embodiment of an apparatus comprising an articulating stent applicator or retrieval device 100a. In this embodiment, a proximal arm 106 is attached to a distal arm 108 at a joint 112. This joint 112 is movable such that an angle formed between the proximal arm 106 and the distal arm 108 can change. One or more claws 114 can extend from the distal arm 108, in the case of a stent retrieval device. Similarly, this articulation mechanism may be used for the trabecular stent applicator, and thus the articulating applicator or retrieval device 100a may be either an applicator for the trabecular stent, a retrieval device, or both, in various embodiments. The embodiment of FIG. 30 may be employed with the any of the various stent embodiments taught or suggested herein.

Figure 31:
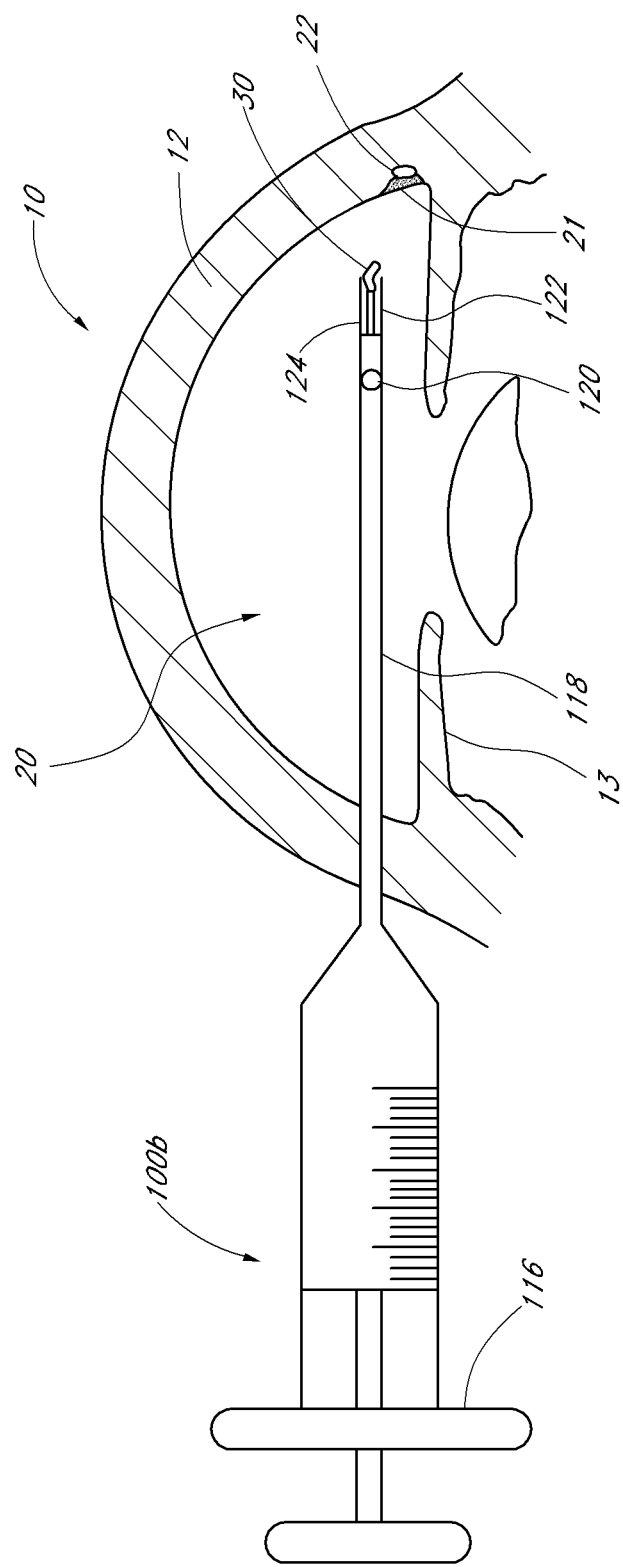
FIG. 31 is a simplified partial view of an eye illustrating the implantation of a glaucoma stent using a delivery apparatus crossing through the eye anterior chamber.

FIG. 31 shows another illustrative method for placing any of the various stent embodiments taught or suggested herein at the implant site within the eye 10. A delivery apparatus 100b generally comprises a syringe portion 116 and a cannula portion 118. The distal section of the cannula 118 has at least one irrigating hole 120 and a distal space 122 for holding the stent device 30. The proximal end 124 of the lumen of the distal space 122 is sealed from the remaining lumen of the cannula portion 118. The delivery apparatus of FIG. 31 may be employed with the any of the various stent embodiments taught or suggested herein.

In one aspect of the invention, a delivery apparatus (or "applicator") is used for placing a trabecular stent through a trabecular meshwork of an eye. Certain embodiments of such a delivery apparatus are disclosed in U.S. application Ser. No. 10/101,548, filed Mar. 18, 2002, entitled APPLICATOR AND METHODS FOR PLACING A TRABECULAR SHUNT FOR GLAUCOMA TREATMENT, published as U.S. Publication No. 2002/0133168 and now abandoned, and U.S. Provisional Application No. 60/276,609, filed Mar. 16, 2001, entitled APPLICATOR AND METHODS FOR PLACING A TRABECULAR SHUNT FOR GLAUCOMA TREATMENT, the entire contents of each one of which are hereby incorporated by reference herein.

Figure 48:
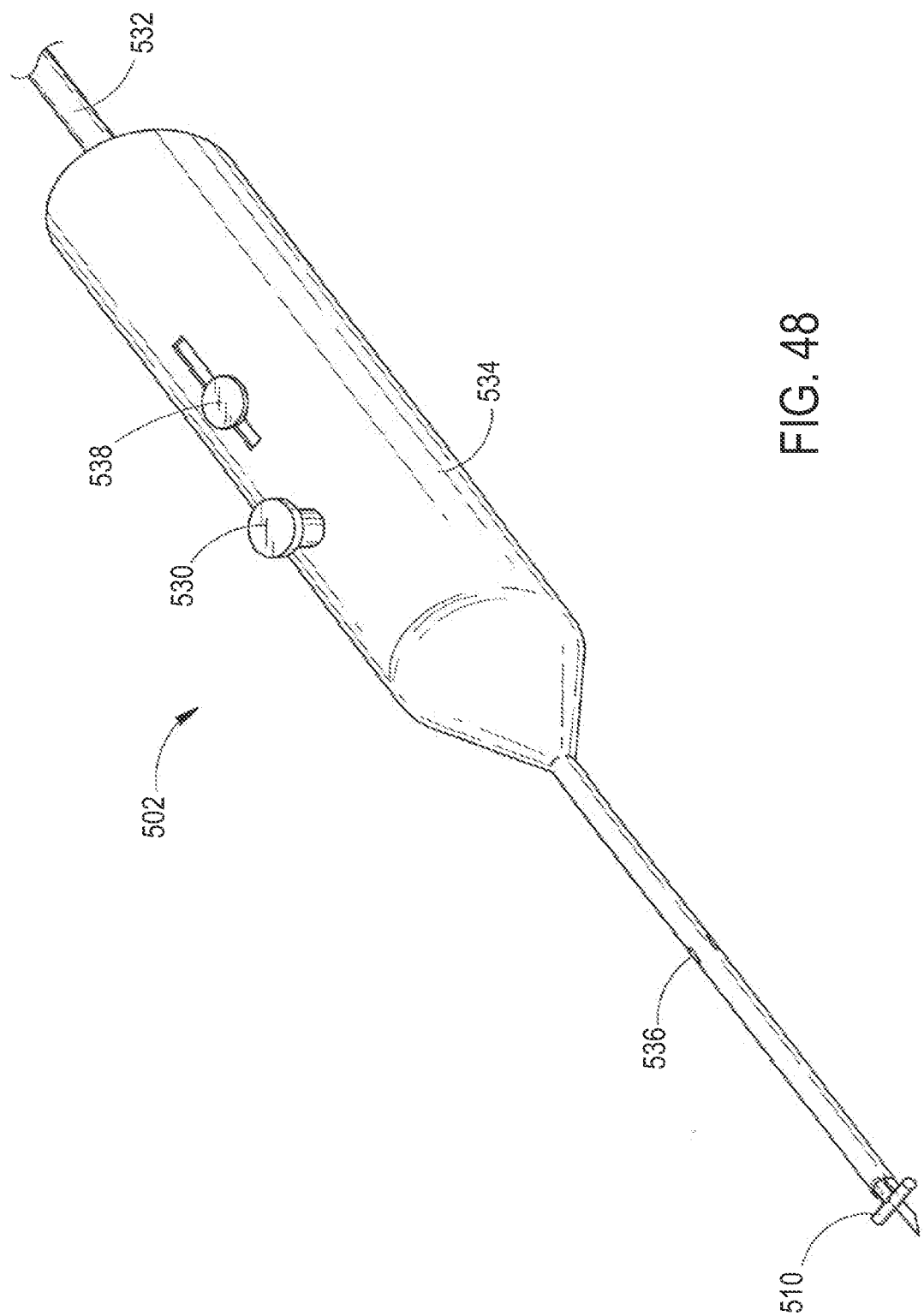
FIG. 48 is an oblique elevational view of a trabecular shunt applicator with a retractable blade mechanism.

FIG. 48 illustrates one embodiment of the trabecular shunt applicator 502, holding the trabecular shunt 510 in place. Additionally, a trabecular meshwork blade 528 extends from the distal end of the applicator 502. In this embodiment, the blade 528 may be extended by spring action from the distal end of the applicator 502 when the operator pushes a button 530 or similarly actuates extension of the blade 528. The blade 528 can be retracted within the applicator 502 by means of a slide button 538, which the operator can move proximally to retract the blade 528. Alternatively, a plunger 532 may move the blade 528 forward and backward within the applicator 502. Also shown is the outer tube 534 of the applicator 502, as well as holes 536 in the applicator 502. These holes 536 may be used for aspiration or irrigation of the anterior chamber of the eye during the performance of trabecular meshwork surgery.

FIG. 49A shows one embodiment of a trabecular meshwork trephine, or punch 542. An inner tube 506 resides within an outer tube 504. The inner tube 506 is in communication with an inner plunger 546. The proximal end 550 of the inner plunger 546 is acted upon by a hammer 552 that is attached to a spring 548. The spring 548 may be recoiled or loaded, storing potential energy, and the hammer 552 is then held in place by an actuator 554 or other similar member in communication with the actuator 554. When the actuator 554 is acted upon by an operator, the spring 548 releases its potential energy, causing the hammer 552 to move forward, contacting the proximal end 550 of the inner plunger 546. This in turn causes the punch 544 to move forward, contacting the trabecular meshwork.

FIG. 49B view is a close-up, cross-sectional view of the punch 544. Again seen as the outer tube 504, the inner tube 506, and the punch 544 of the device. This trephine or punch may comprise a circular blade 556 or other similar configuration known to those skilled in the art for making a cut or punch hole in the trabecular meshwork of an eye.

Figure 50A:
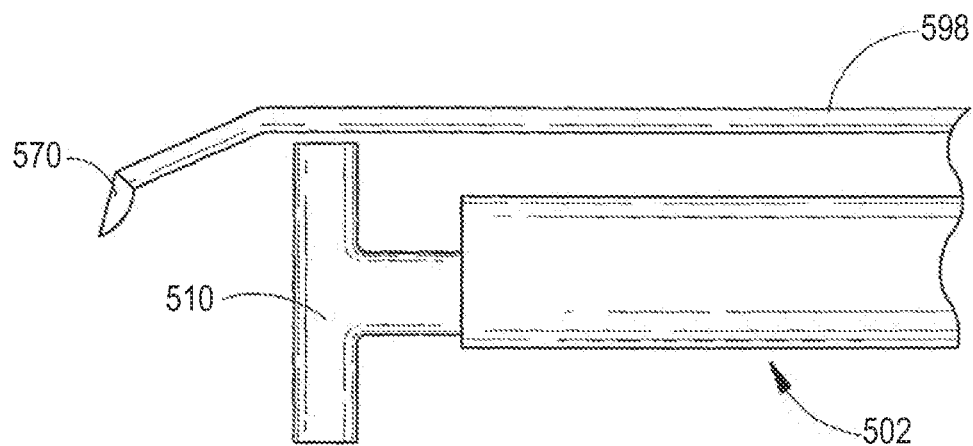
FIGS. 50A and 50B are elevational views of a control arm and trabeculotomy device for the trabecular shunt applicator.
Figure 50B:
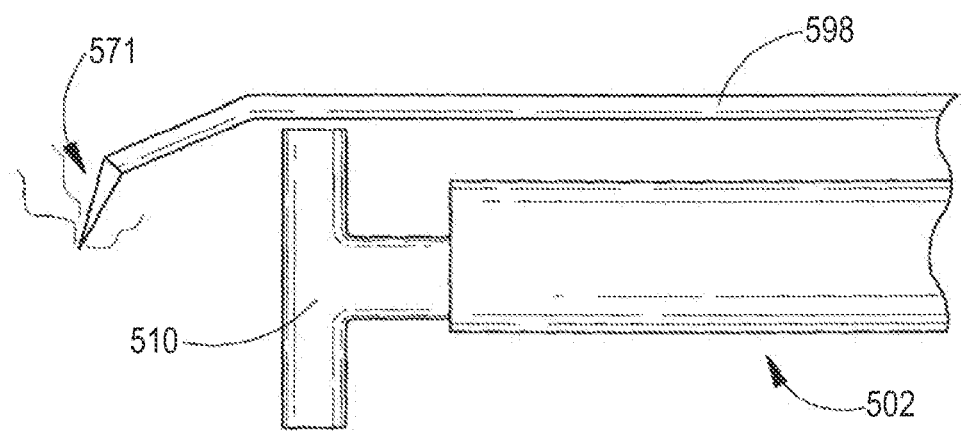

FIGS. 50A and 50B illustrate embodiments of a control arm 598 which is attached to a mechanism for performing trabeculotomy. In FIG. 50A, a blade 570 extends from an end of the control arm 598. In some embodiments, the long axis of the control arm 598 runs parallel or semiparallel to the long axis of the applicator 502. The blade 570 may be used to make a trabeculotomy in preparation for placing the trabecular shunt 510 through the trabecular meshwork and into Schlemm's canal.

FIG. 50B shows a "hot tip" 571 at the end of the control arm 598. This hot tip 571 may be a cautery, laser, or other energy transfer device for making a hole in the trabecular meshwork in preparation for placing the shunt 510 through the trabecular meshwork and into Schlemm's canal.

Figure 51A:
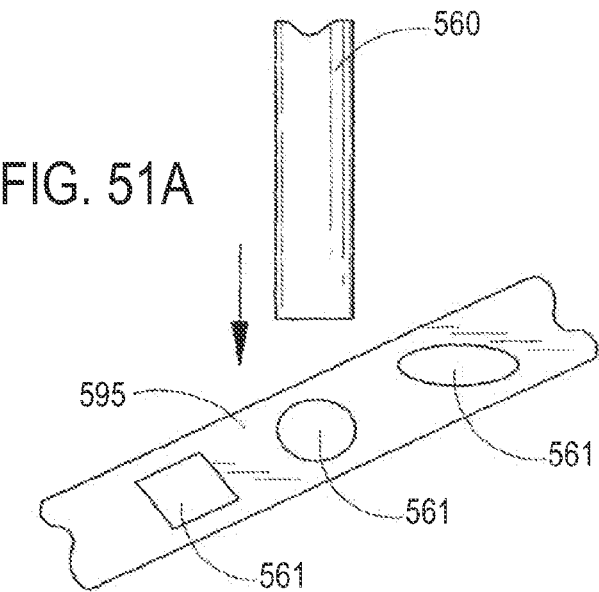
FIGS. 51A through 51C are schematic oblique elevational views of various trabecular meshwork punching and drilling devices.
Figure 51B:
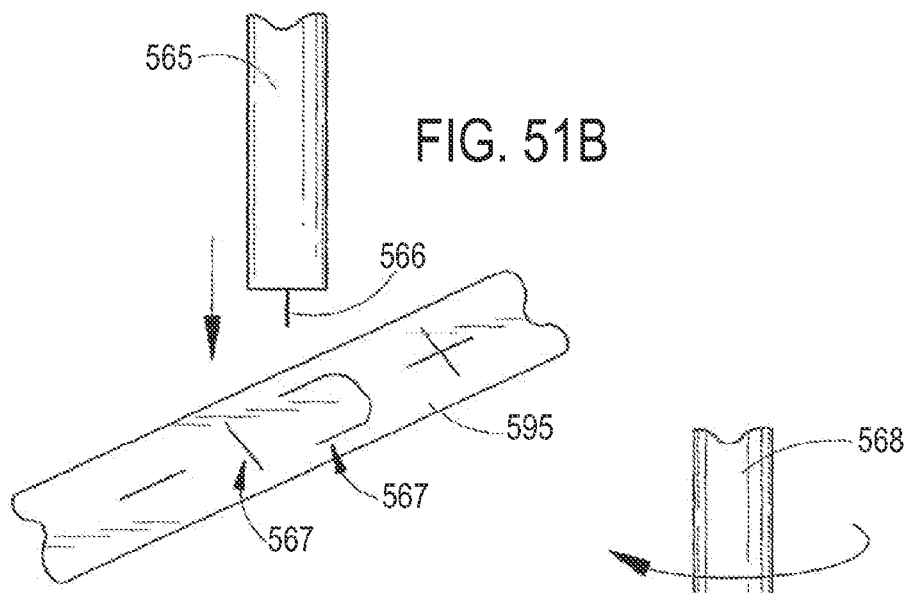
Figure 51C:
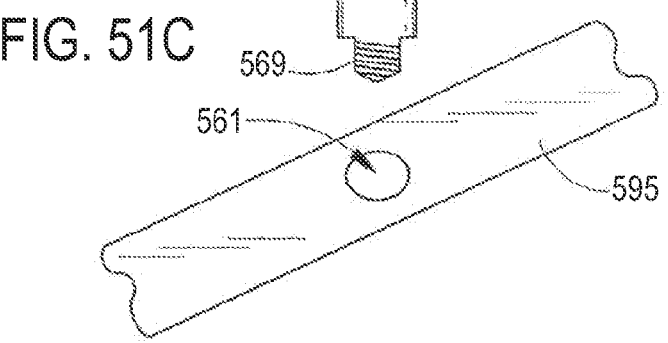

FIGS. 51A through 51C illustrate various embodiments of devices, such as trephines, that can punch holes in the trabecular meshwork. In FIG. 51A, a trabecular meshwork punch 560 is illustrated. This punch 560 can make holes 561 in the trabecular meshwork 595. These holes 561 can be of various configurations, depending on the shape of the distal blade of the trabecular meshwork punch 560.

In FIG. 51B, a blade 566 extends from the end of a trabecular meshwork cutter 565. This blade 566 can make various punch holes 567 in the trabecular meshwork 595, as illustrated.

FIG. 51C illustrates a trabecular meshwork drill 568. The drill 568 has a distal drill bit 569, which can make a drill hole 561 in the trabecular meshwork 595.

The stent has an inlet section and an outlet section. The delivery apparatus includes a handpiece, an elongate tip, a holder and an actuator. The handpiece has a distal end and a proximal end. The elongate tip is connected to the distal end of the handpiece. The elongate tip has a distal portion and is configured to be placed through a corneal incision and into an anterior chamber of the eye. The holder is attached to the distal portion of the elongate tip. The holder is configured to hold and release the inlet section of the trabecular stent. The actuator is on the handpiece and actuates the holder to release the inlet section of the trabecular stent. When the trabecular stent is deployed from the delivery apparatus into the eye, the outlet section is positioned in substantially opposite directions inside Schlemm's canal. In one embodiment, a deployment mechanism within the delivery apparatus includes a push-pull type plunger.

In some embodiments, the holder comprises a clamp. In some embodiments, the apparatus further comprises a spring within the handpiece that is configured to be loaded when the stent is being held by the holder, the spring being at least partially unloaded upon actuating the actuator, allowing for release of the stent from the holder.

In various embodiments, the clamp comprises a plurality of claws configured to exert a clamping force onto the inlet section of the stent. The holder may also comprise a plurality of flanges.

In some embodiments, the distal portion of the elongate tip is made of a flexible material. This can be a flexible wire. The distal portion can have a deflection range, preferably of about 45 degrees from the long axis of the handpiece.

The delivery apparatus can further comprise an irrigation port in the elongate tip.

Some aspects include a method of placing a trabecular stent through a trabecular meshwork of an eye, the stent having an inlet section and an outlet section, including advancing a delivery apparatus holding the trabecular stent through an anterior chamber of the eye and into the trabecular meshwork, placing part of the stent through the trabecular meshwork and into a Schlemm's canal of the eye; and releasing the stent from the delivery apparatus.

In various embodiments, the method includes using a delivery apparatus that comprises a handpiece having a distal end and a proximal end; an elongate tip connected to the distal end of the handpiece, the elongate tip having a distal portion and being configured to be placed through a corneal incision and into an anterior chamber of the eye; a holder attached to the distal portion of the elongate tip, the holder configured to hold and release the inlet section of the trabecular stent; and an actuator on the handpiece that actuates the holder to release the inlet section of the trabecular stent from the holder.

In one aspect, the trabecular stent is removably attached to a delivery apparatus (also known as "applicator"). When the trabecular stent is deployed from the delivery apparatus into the eye, the outlet section is positioned in substantially opposite directions inside Schlemm's canal. In one embodiment, a deployment mechanism within the delivery apparatus includes a push-pull type plunger. In some embodiments, the delivery applicator may be a guidewire, an expandable basket, an inflatable balloon, or the like.

OTHER EMBODIMENTS

Figure 32:
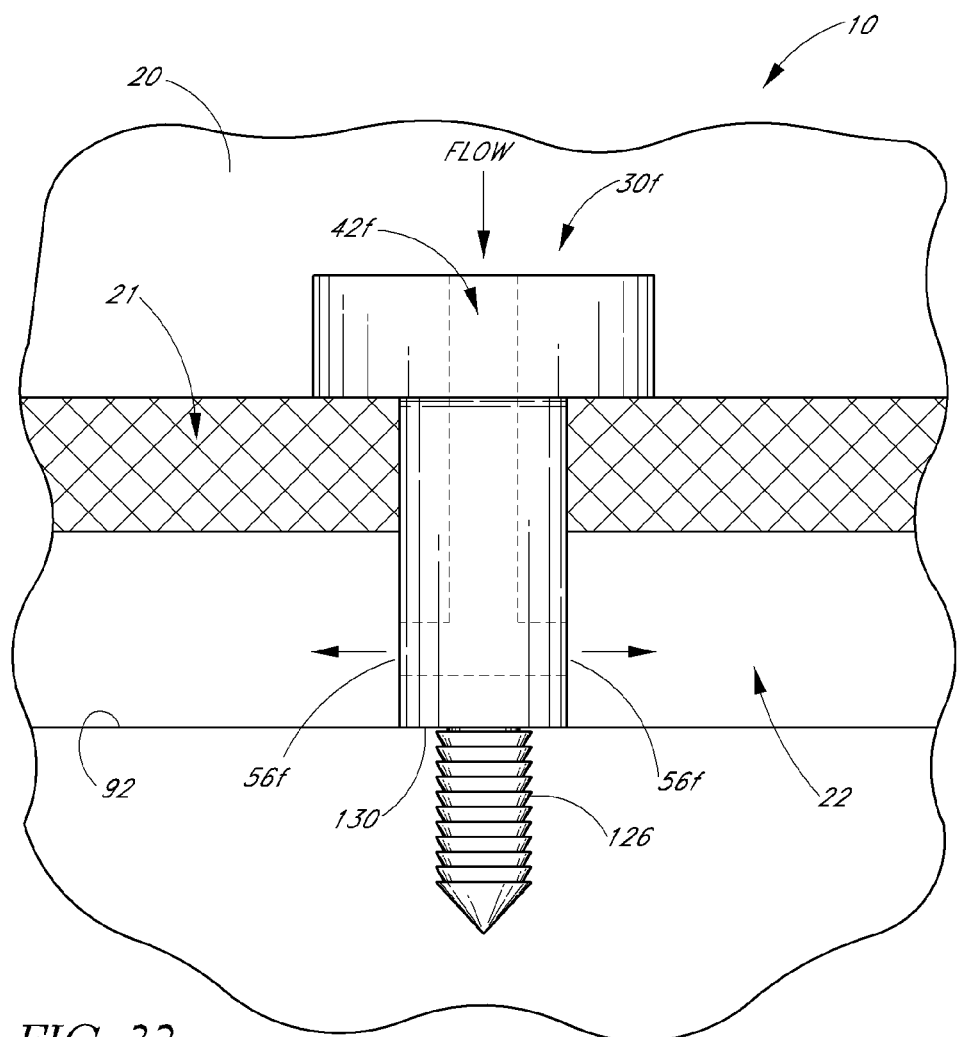
FIG. 32 is a simplified partial view of an eye illustrating the implantation of a glaucoma stent having features and advantages in accordance with one embodiment of the invention.
Figure 33:
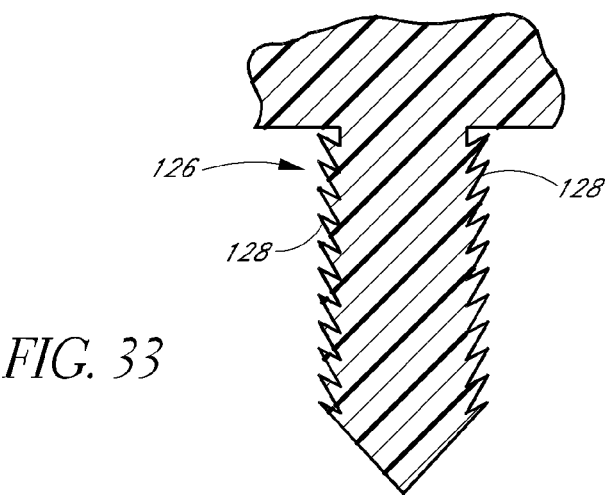
FIG. 33 is a detailed enlarged view of the barbed pin of FIG. 32.

Screw/Barb Anchored Stent:

FIGS. 32 and 33 illustrate a glaucoma stent device 30f having features and advantages in accordance with one embodiment. This embodiment of the trabecular stent 30f includes a barbed or threaded screw-like extension or pin 126 with barbs 128 for anchoring. The barbed pin 126 extends from a distal or base portion 130 of the stent 30f.

In use, the stent 30f (FIG. 32) is advanced through the trabecular meshwork 21 and across Schlemm's canal 22. The barbed (or threaded) extension 126 penetrates into the back wall 92 of Schlemm's canal 22 up to the shoulder or base 130 that then rests on the back wall 92 of the canal 22. The combination of a shoulder 130 and a barbed pin 126 of a particular length limits the penetration depth of the barbed pin 126 to a predetermined or preselected distance. In one embodiment, the length of the pin 126 is about 0.5 mm or less. Advantageously, this barbed configuration provides a secure anchoring of the stent 30f. As discussed above, correct orientation of the stent 30f is ensured by appropriate fiducial marks, indicia or the like and by positioning of the stent in a preloaded applicator.

Referring to FIG. 32, the aqueous flows from the anterior chamber 20, through the lumen 42f, then out through two side-ports 56f to be directed in both directions along Schlemm's canal 22. Alternatively, flow could be directed in only one direction through a single side-port 56f. In other embodiments, more than two outlet ports 56f, for example, six to eight ports (like a pin wheel configuration), may be efficaciously used, as needed or desired.

Still referring to FIG. 32, in one embodiment, the stent 30f is inserted through a previously made incision in the trabecular meshwork 21. In other embodiments, the stent 30f may be combined with any of the blade configurations taught or suggested herein to provide self-trephining capability. In these cases, the incision through the trabecular meshwork 21 is made by the self-trephining stent device which has a blade at its base or proximate to the base.

Figure 34:
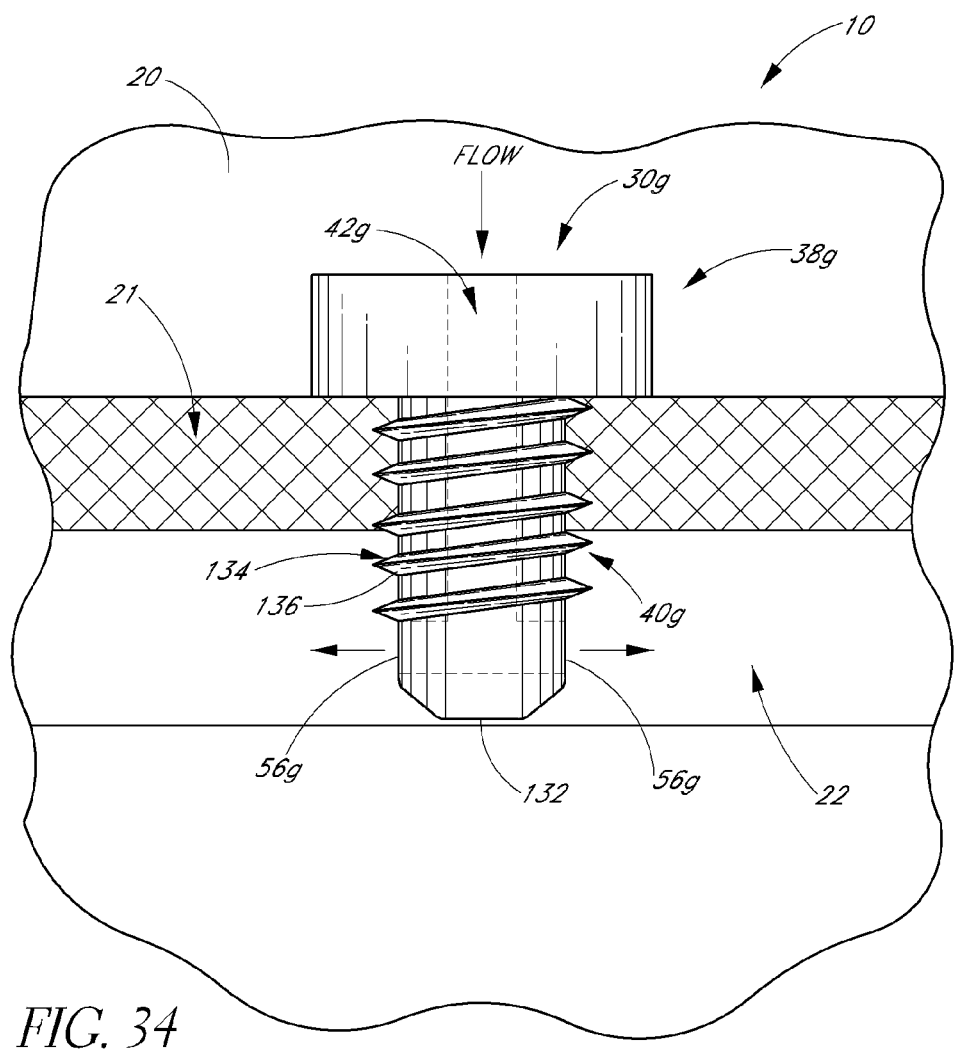
FIG. 34 is a simplified partial view of an eye illustrating the implantation of a glaucoma stent having features and advantages in accordance with one embodiment of the invention.

Deeply Threaded Stent:

FIG. 34 illustrates a glaucoma stent device 30g having features and advantages in accordance with one embodiment. The stent 30g has a head or seat 38g and a shank or main body portion 40g with a base or distal end 132. This embodiment of the trabecular stent 30g includes a deep thread 134 (with threads 136) on the main body 40g of the stent 30g below the head 38g. The threads may or may not extend all the way to the base 132.

In use, the stent 30g (FIG. 34) is advanced through the meshwork 21 through a rotating motion, as with a conventional screw. Advantageously, the deep threads 136 provide retention and stabilization of the stent 30g in the trabecular meshwork 21.

Referring to FIG. 34, the aqueous flows from the anterior chamber 20, through the lumen 42g, then out through two side-ports 56g to be directed in both directions along Schlemm's canal 22. Alternatively, flow could be directed in only one direction through a single side-port 56g. In other embodiments, more than two outlet ports 56g may be efficaciously used, as needed or desired.

One suitable applicator or delivery apparatus for this stent 30g (FIG. 34) includes a preset rotation, for example, via a wound torsion spring or the like. The rotation is initiated by a release trigger on the applicator. A final twist of the applicator by the surgeon and observation of suitable fiducial marks, indicia or the like ensure proper alignment of the side ports 56g with Schlemm's canal 22.

Referring to FIG. 34, in one embodiment, the stent 30g is inserted through a previously made incision in the trabecular meshwork 21. In other embodiments, the stent 30g may be combined with any of the blade configurations taught or suggested herein to provide self-trephining capability. In these cases, the incision through the trabecular meshwork 21 is made by the self-trephining stent device which has a blade at its base or proximate to the base.

Figure 35:
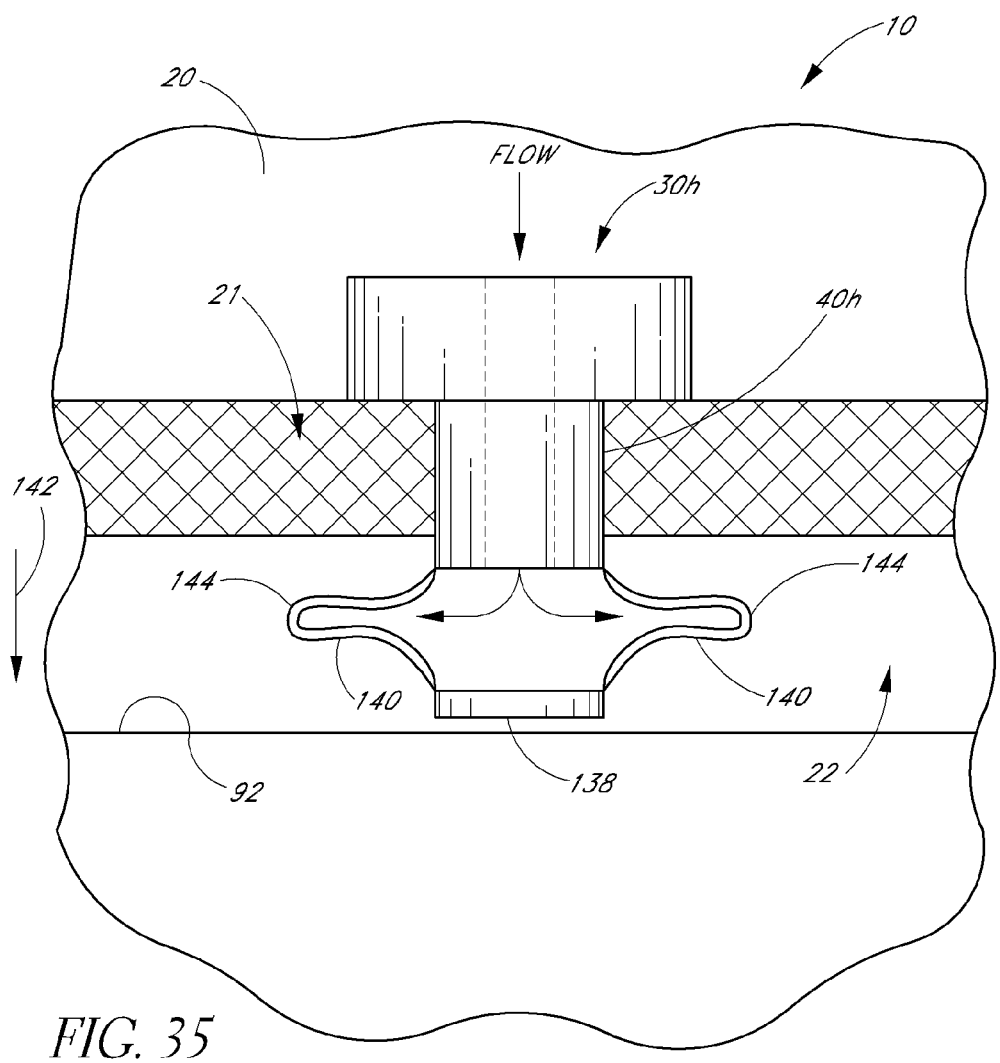
FIG. 35 is a simplified partial view of an eye illustrating the implantation of a glaucoma stent having features and advantages in accordance with one embodiment of the invention.

Rivet Style Stent:

FIG. 35 illustrates a glaucoma stent device 30h having features and advantages in accordance with one embodiment. The stent has a base or distal end 138. This embodiment of the trabecular stent 30*h* has a pair of flexible ribs 140. In the unused state, the ribs are initially generally straight (that is, extend in the general direction of arrow 142).

Referring to FIG. 35, upon insertion of the stent 30*h* through the trabecular meshwork 21, the ends 144 of respective ribs 140 of the stent 30*h* come to rest on the back wall 92 of Schlemm's canal 22. Further advancement of the stent 30*h* causes the ribs 140 to deform to the bent shape as shown in the drawing of FIG. 35. The ribs 140 are designed to first buckle near the base 138 of the stent 30*h*. Then the buckling point moves up the ribs 140 as the shank part 40*h* of the stent 30*h* is further advanced through the trabecular meshwork 21.

The lumen 42*h* (FIG. 35) in the stent 30*h* is a simple straight hole. The aqueous flows from the anterior chamber 20, through the lumen 42*h*, then out around the ribs 140 to the collector channels further along Schlemm's canal 22 in either direction.

Referring to FIG. 35, in one embodiment, the stent 30*h* is inserted through a previously made incision in the trabecular meshwork 21. In other embodiments, the stent 30*h* may be combined with any of the blade configurations taught or suggested herein to provide self-trephining capability. In these cases, the incision through the trabecular meshwork 21 is made by the self-trephining stent device which has a blade at its base or proximate to the base.

Figure 36:
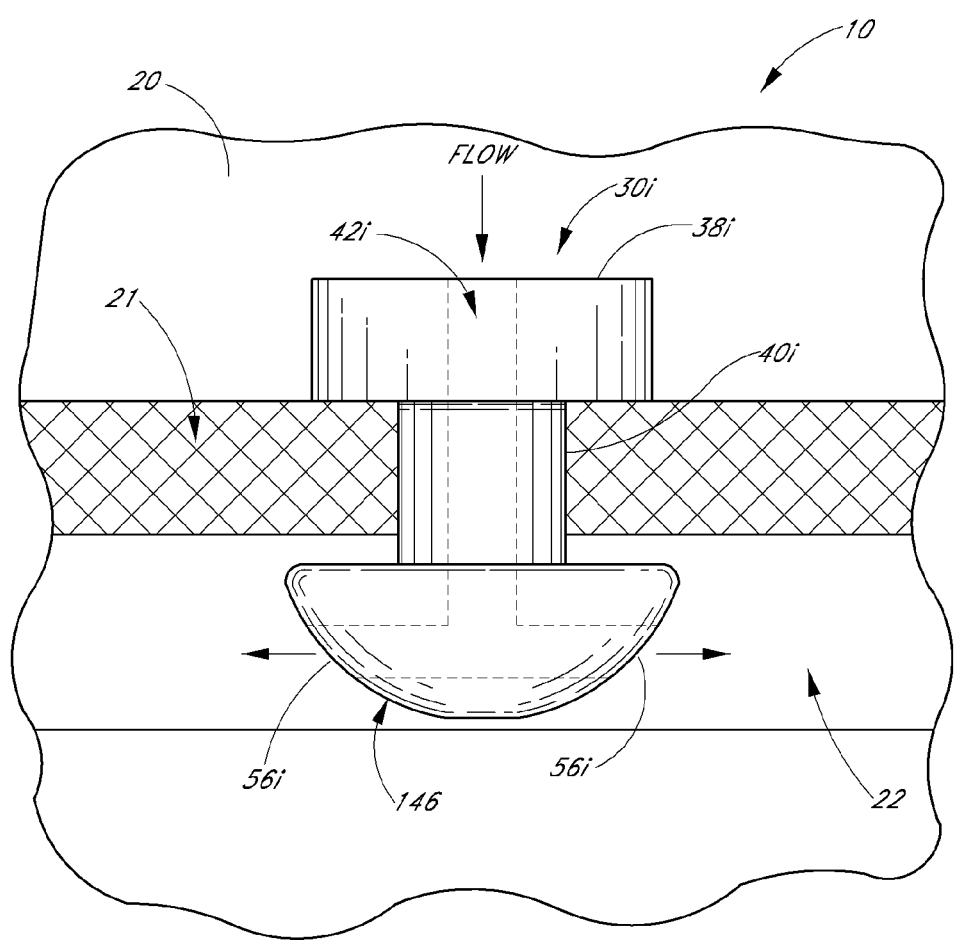
FIG. 36 is a simplified partial view of an eye illustrating the implantation of a glaucoma stent having features and advantages in accordance with one embodiment of the invention.

Grommet Style Stent:

FIG. 36 illustrates a glaucoma stent device 30*i* having features and advantages in accordance with one embodiment. This embodiment of the trabecular stent 30*i* includes a head or seat 38*i*, a tapered base portion 146 and an intermediate narrower waist portion or shank 40*i*.

In use, the stent 30*i* (FIG. 36) is advanced through the trabecular meshwork 21 and the base 146 is pushed into Schlemm's canal 22. The stent 30*i* is pushed slightly further, if necessary, until the meshwork 21 stretched by the tapered base 146 relaxes back and then contracts to engage the smaller diameter portion waist 40*i* of the stent 30*i*. Advantageously, the combination of the larger diameter head or seat 38*i* and base 146 of the stent 30*i* constrains undesirable stent movement. As discussed above, correct orientation of the stent 30*i* is ensured by appropriate fiducial marks, indicia or the like and by positioning of the stent in a preloaded applicator.

Referring to FIG. 36, the aqueous flows from the anterior chamber 20, through the lumen 42*i*, then out through two side-ports 56*i* to be directed in both directions along Schlemm's canal 22. Alternatively, flow could be directed in only one direction through a single side-port 56*i*. In other embodiments, more than two outlet ports 56*i* may be efficaciously used, as needed or desired.

Still referring to FIG. 36, in one embodiment, the stent 30*i* is inserted through a previously made incision in the trabecular meshwork 21. In other embodiments, the stent 30*i* may be combined with any of the blade configurations taught or suggested herein to provide self-trephining capability. In these cases, the incision through the trabecular meshwork 21 is made by the self-trephining stent device which has a blade at its base or proximate to the base.

Figure 37:
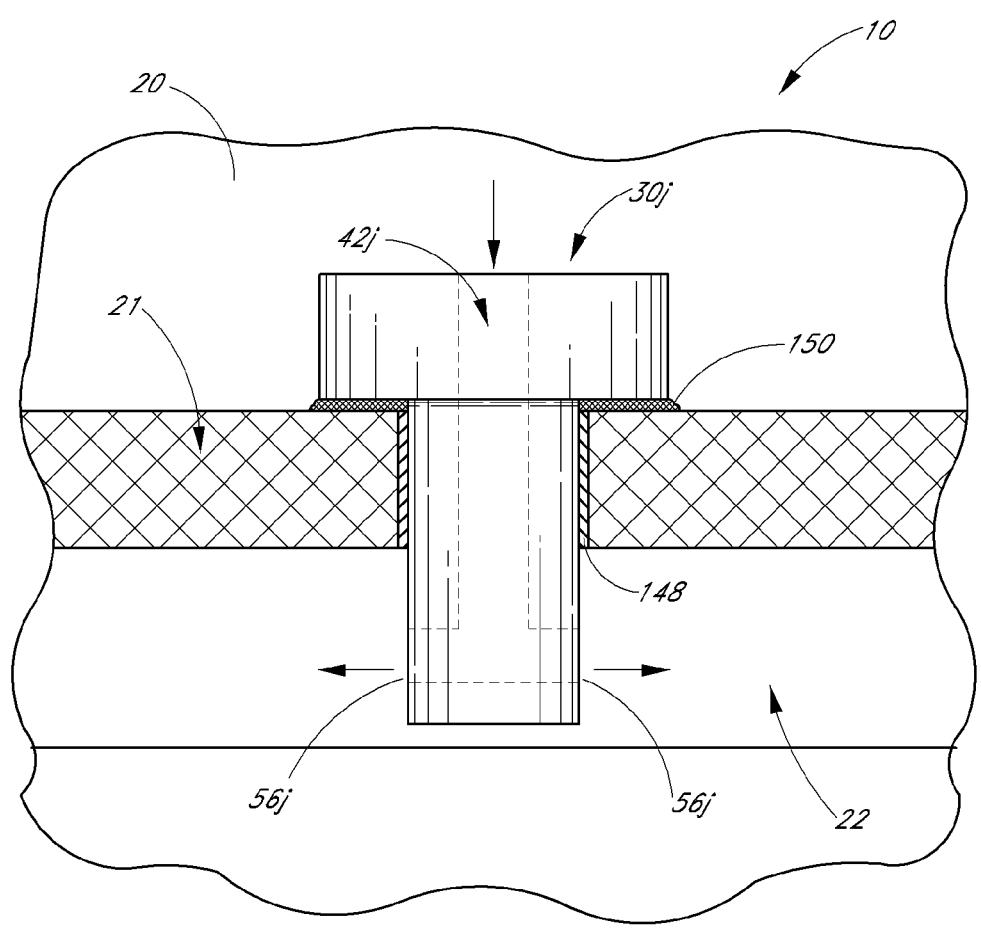
FIG. 37 is a simplified partial view of an eye illustrating the implantation of a glaucoma stent having features and advantages in accordance with one embodiment of the invention.

Biointeractive Stent:

FIG. 37 illustrates a glaucoma stent device 30*j* having features and advantages in accordance with one embodiment. This embodiment of the trabecular stent 30*j* utilizes a region of biointeractive material 148 that provides a site for the trabecular meshwork 21 to firmly grip the stent 30*j* by ingrowth of the tissue into the biointeractive material 148. As shown in FIG. 37, preferably the biointeractive layer 148 is applied to those surfaces of the stent 30*j* which would abut against or come in contact with the trabecular meshwork 21.

In one embodiment, the biointeractive layer 148 (FIG. 37) may be a region of enhanced porosity with a growth promoting chemical. In one embodiment, a type of bio-glue 150 that dissolves over time is used to hold the stent secure during the time between insertion and sufficient ingrowth for stabilization. As discussed above, correct orientation of the stent 30*j* is ensured by appropriate fiducial marks, indicia or the like and by positioning of the stent in a preloaded applicator.

Referring to FIG. 37, the aqueous flows from the anterior chamber 20, through the lumen 42*j*, then out through two side-ports 56*j* to be directed in both directions along Schlemm's canal 22. Alternatively, flow could be directed in only one direction through a single side-port 56*j*. In other embodiments, more than two outlet ports 56*j* may be efficaciously used, as needed or desired.

Still referring to FIG. 37, in one embodiment, the stent 30*j* is inserted through a previously made incision in the trabecular meshwork 21. In other embodiments, the stent 30*j* may be combined with any of the blade configurations taught or suggested herein to provide self-trephining capability. In these cases, the incision through the trabecular meshwork 21 is made by the self-trephining stent device which has a blade at its base or proximate to the base.

Figure 38:
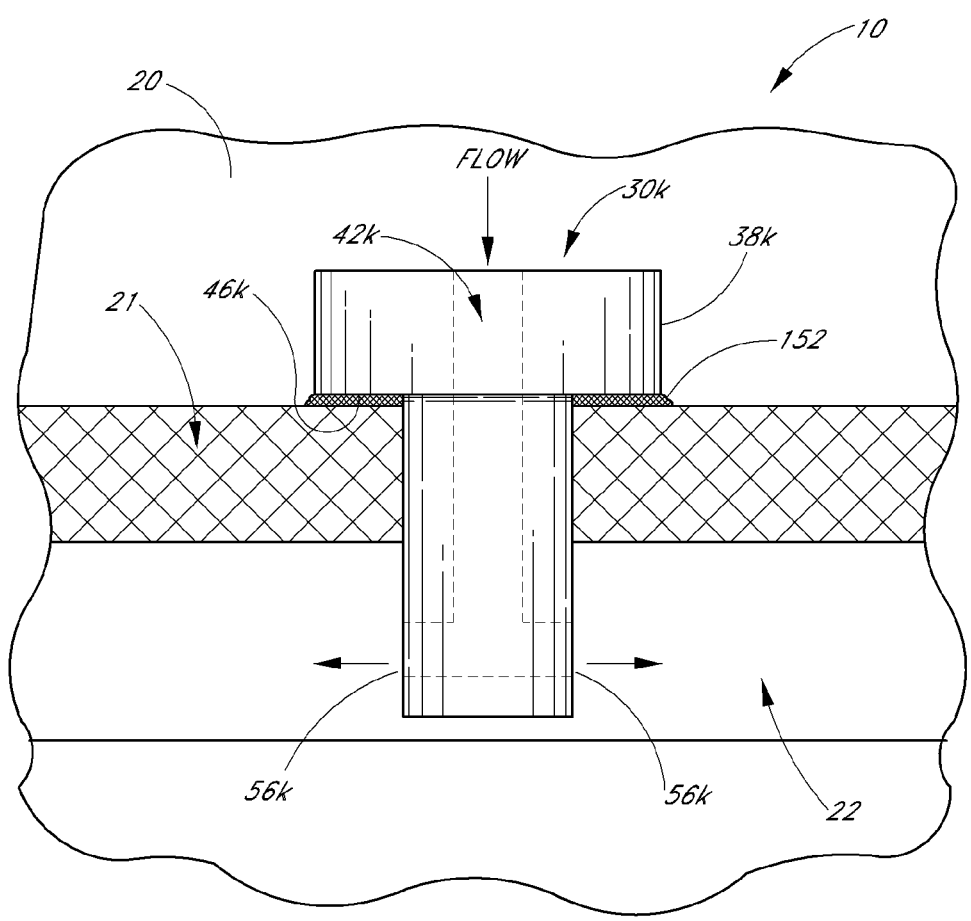
FIG. 38 is a simplified partial view of an eye illustrating the implantation of a glaucoma stent having features and advantages in accordance with one embodiment of the invention.

Glued or Welded Stent:

FIG. 38 illustrates a glaucoma stent device 30*k* having features and advantages in accordance with one embodiment. This embodiment of the trabecular stent 30*k* is secured in place by using a permanent (non-dissolving) bio-glue 152 or a "welding" process (e.g. heat) to form a weld 152. The stent 30*k* has a head or seat 38*k* and a lower surface 46*k*.

The stent 30*k* is advanced through the trabecular meshwork 21 until the head or seat 38*k* comes to rest on the trabecular meshwork 21, that is, the head lower surface 46*k* abuts against the trabecular meshwork 21, and the glue or weld 152 is applied or formed therebetween, as shown in FIG. 38. As discussed above, correct orientation of the stent 30*k* is ensured by appropriate fiducial marks, indicia or the like and by positioning of the stent in a preloaded applicator.

Referring to FIG. 38, the aqueous flows from the anterior chamber 20, through the lumen 42*k*, then out through two side-ports 56*k* to be directed in both directions along Schlemm's canal 22. Alternatively, flow could be directed in only one direction through a single side-port 56*k*. In other embodiments, more than two outlet ports 56*k* may be efficaciously used, as needed or desired.

Still referring to FIG. 38, in one embodiment, the stent 30*k* is inserted through a previously made incision in the trabecular meshwork 21. In other embodiments, the stent 30*k* may be combined with any of the blade configurations taught or suggested herein to provide self-trephining capability. In these cases, the incision through the trabecular meshwork 21 is made by the self-trephining stent device which has a blade at its base or proximate to the base.

Figure 39:
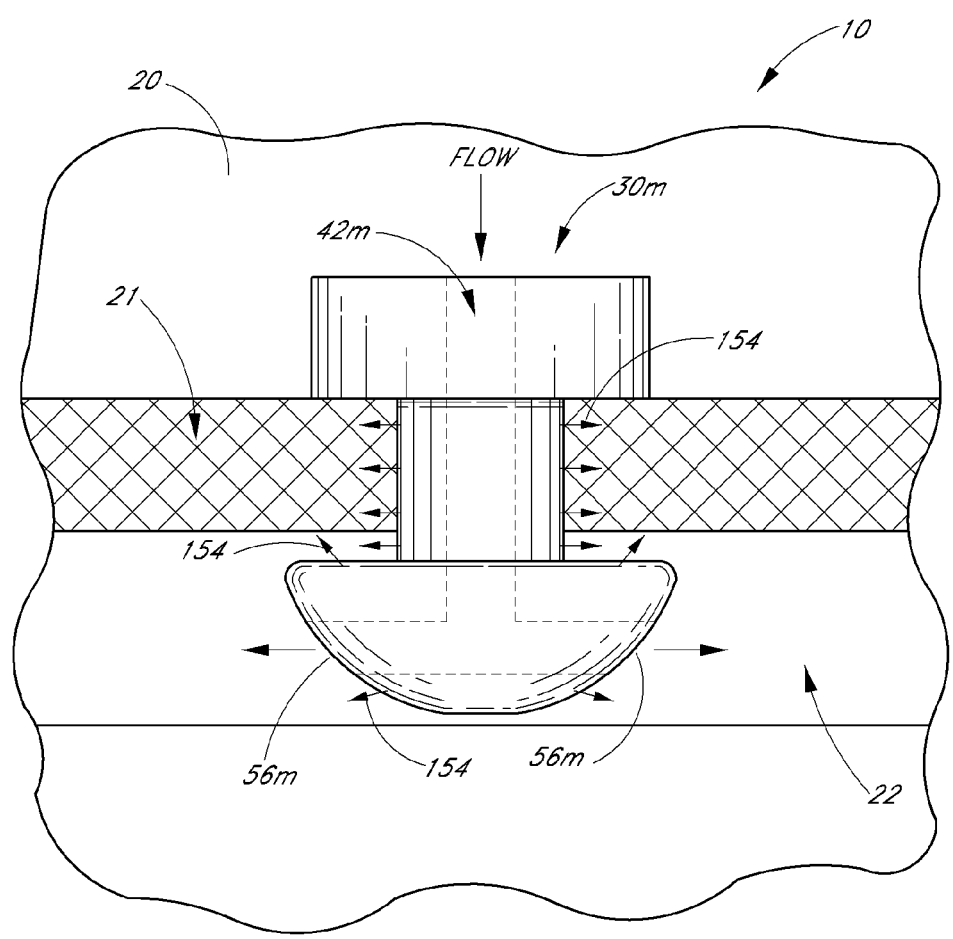
FIG. 39 is a simplified partial view of an eye illustrating the implantation of a glaucoma stent having features and advantages in accordance with one embodiment of the invention.

Hydrophilic Latching Stent:

FIG. 39 illustrates a glaucoma stent device 30*m* having features and advantages in accordance with one embodiment. This embodiment of the trabecular stent 30*m* is fabricated from a hydrophilic material that expands with absorption of water. Desirably, this would enable the device 30*m* to be inserted through a smaller incision in the trabecular meshwork 21. The subsequent expansion (illustrated by the smaller arrows 154) of the stent 30*m* would advantageously enable it to latch in place in the trabecular meshwork 21. As discussed above, correct orientation of the stent 30*m* is ensured by appropriate fiducial marks, indicia or the like and by positioning of the stent in a preloaded applicator.

Referring to FIG. 39, the aqueous flows from the anterior chamber 20, through the lumen 42*m*, then out through two side-ports 56*m* to be directed in both directions along Schlemm's canal 22. Alternatively, flow could be directed in only one direction through a single side-port 56*m*. In other embodiments, more than two outlet ports 56*m* may be efficaciously used, as needed or desired.

Still referring to FIG. 39, in one embodiment, the stent 30*m* is inserted through a previously made incision in the trabecular meshwork 21. In other embodiments, the stent 30*m* may be combined with any of the blade configurations taught or suggested herein to provide self-trephining capability. In these cases, the incision through the trabecular meshwork 21 is made by the self-trephining stent device which has a blade at its base or proximate to the base.

Figure 40:
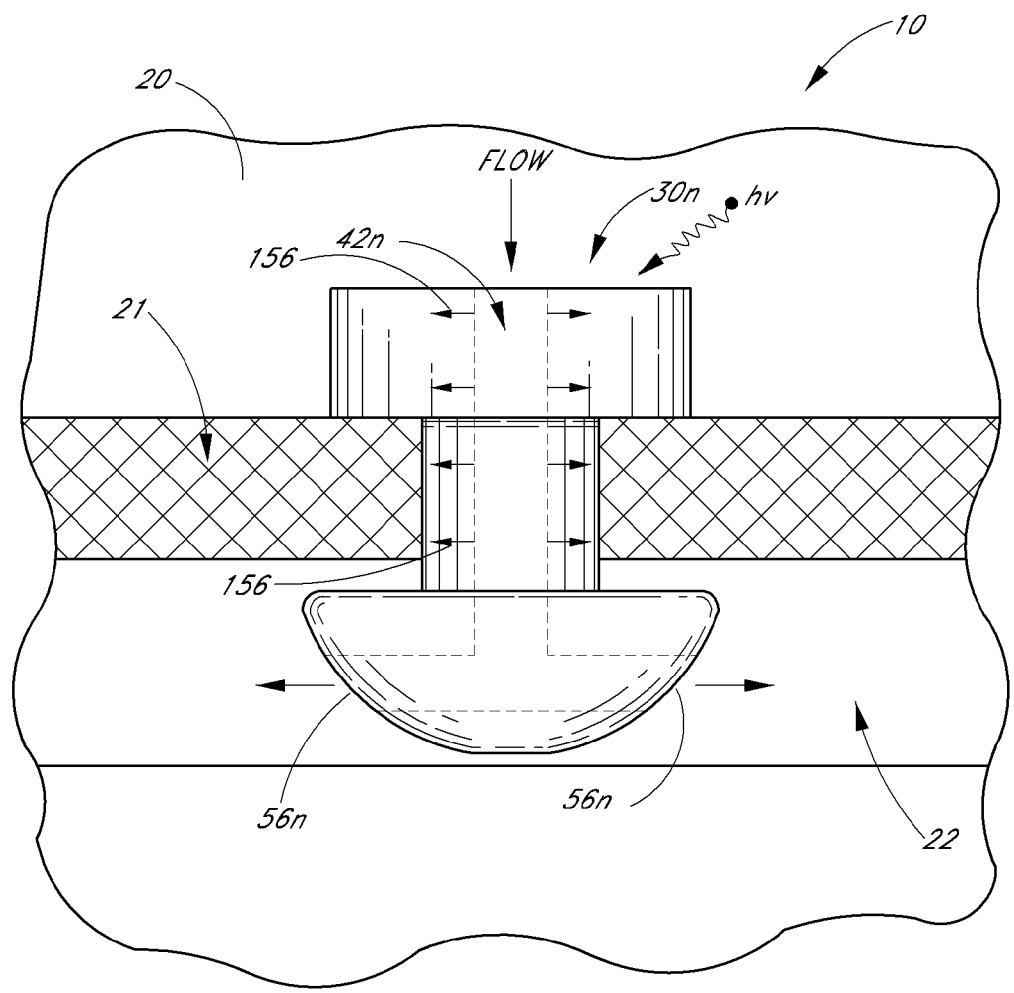
FIG. 40 is a simplified partial view of an eye illustrating the implantation of a glaucoma stent having features and advantages in accordance with one embodiment of the invention.

Photodynamic Stent:

FIG. 40 illustrates a glaucoma stent device 30*n* having features and advantages in accordance with one embodiment. This embodiment of the trabecular stent 30*n* is fabricated from a photodynamic material that expands on exposure to light.

It is commonly known that there is a diurnal variation in the aqueous humor production by the eye—it is higher during the day than it is at night. The lumen 42*n* of the stent 30*n* responds to light entering the cornea during the day by expanding and allowing higher flow of aqueous through the lumen 42*n* and into Schlemm's canal 22. This expansion is generally indicated by the smaller arrows 156 (FIG. 40) which show the lumen 42*n* (and ports) expanding or opening in response to light stimulus. (The light or radiation energy E is generally given by E=hv, where h is Planck's constant and v is the frequency.) At night, in darkness, the lumen diameter decreases and reduces the flow allowed through the lumen 42*n*. In one embodiment, an excitation wavelength that is different from that commonly encountered is provided on an as-needed basis to provide higher flow of aqueous to Schlemm's canal 22.

This photodynamic implementation is shown in FIG. 40 for the self-latching style of stent 30*n*, but can be efficaciously used with any of the other stent embodiments, as needed or desired. As discussed above, correct orientation of the stent 30*n* is ensured by appropriate fiducial marks, indicia or the like and by positioning of the stent in a preloaded applicator.

Referring to FIG. 40, the aqueous flows from the anterior chamber 20, through the lumen 42*n*, then out through two side-ports 56*n* to be directed in both directions along Schlemm's canal 22. Alternatively, flow could be directed in only one direction through a single side-port 56*n*. In other embodiments, more than two outlet ports 56*n* may be efficaciously used, as needed or desired.

Still referring to FIG. 40, in one embodiment, the stent 30*n* is inserted through a previously made incision in the trabecular meshwork 21. In other embodiments, the stent 30*n* may be combined with any of the blade configurations taught or suggested herein to provide self-trephining capability. In these cases, the incision through the trabecular meshwork 21 is made by the self-trephining stent device which has a blade at its base or proximate to the base.

Figure 41:
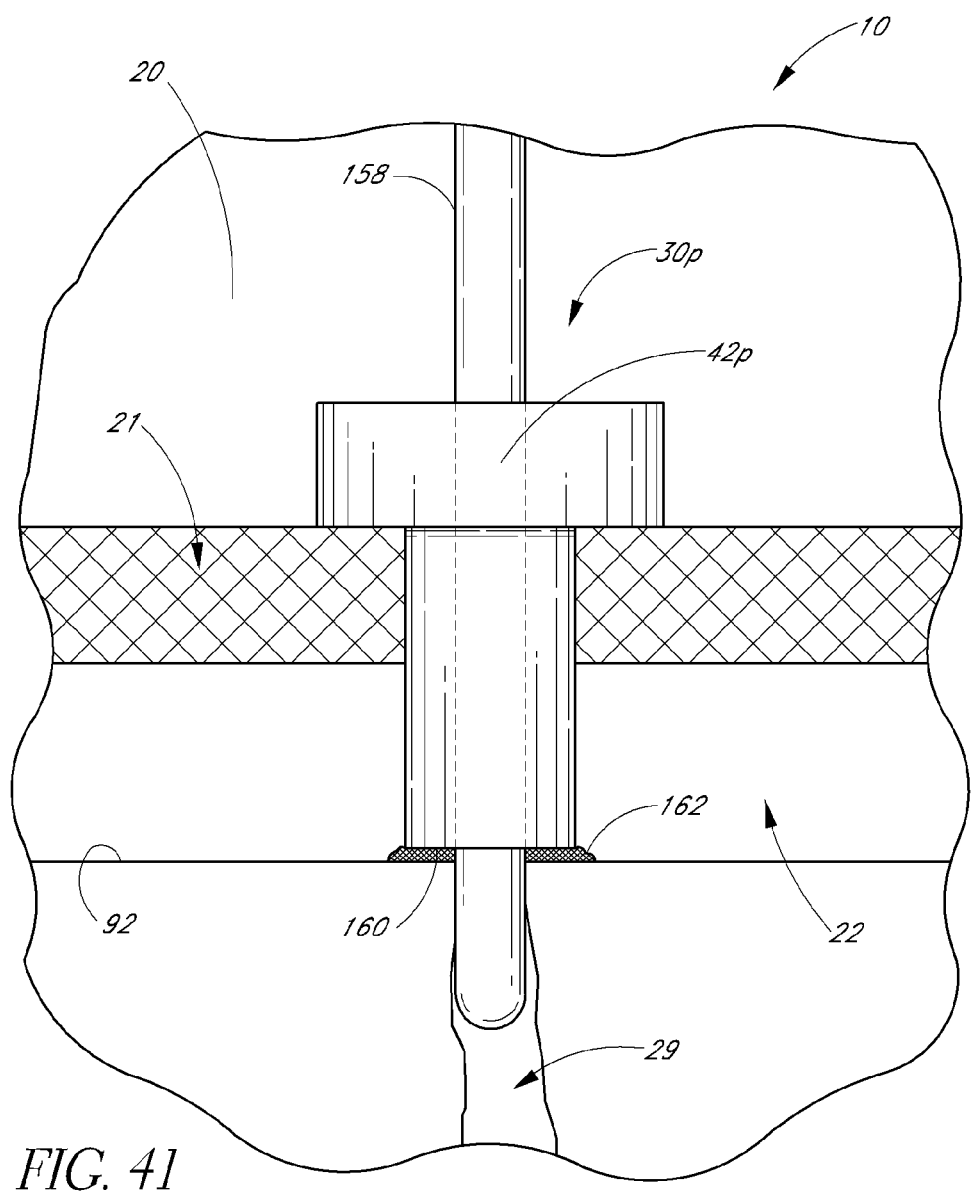
FIG. 41 is a simplified partial view of an eye illustrating the implantation of a glaucoma stent having features and advantages in accordance with one embodiment of the invention.

Collector Channel Alignment Stent:

FIG. 41 illustrates a glaucoma stent device 30*p* having features and advantages in accordance with one embodiment. This figure depicts an embodiment of a stent 30*p* that directs aqueous from the anterior chamber 20 directly into a collector channel 29 which empties into aqueous veins. The stent 30*p* has a base or distal end 160.

In the illustrated embodiment of FIG. 41, a removable alignment pin 158 is utilized to align the stent lumen 42*p* with the collector channel 29. In use, the pin 158 extends through the stent lumen 42*p* and protrudes through the base 160 and extends into the collector channel 29 to center and/or align the stent 30*p* over the collector channel 29. The stent 30*p* is then pressed firmly against the back wall 92 of Schlemm's canal 22. A permanent bio-glue 162 is used between the stent base and the back wall 92 of Schlemm's canal 22 to seat and securely hold the stent 30*p* in place. Once positioned, the pin 158 is withdrawn from the lumen 42*p* to allow the aqueous to flow directly from the anterior chamber 20 into the collector duct 29. The collector ducts are nominally 20 to 100 micrometers (μm) in diameter and are visualized with a suitable microscopy method (such as ultrasound biomicroscopy (UBM)) or laser imaging to provide guidance for placement of the stent 30*p*.

Referring to FIG. 41, in one embodiment, the stent 30*p* is inserted through a previously made incision in the trabecular meshwork 21. In other embodiments, the stent 30*p* may be combined with any of the blade configurations taught or suggested herein to provide self-trephining capability. In these cases, the incision through the trabecular meshwork 21 is made by the self-trephining stent device which has a blade at its base or proximate to the base.

Figure 42:
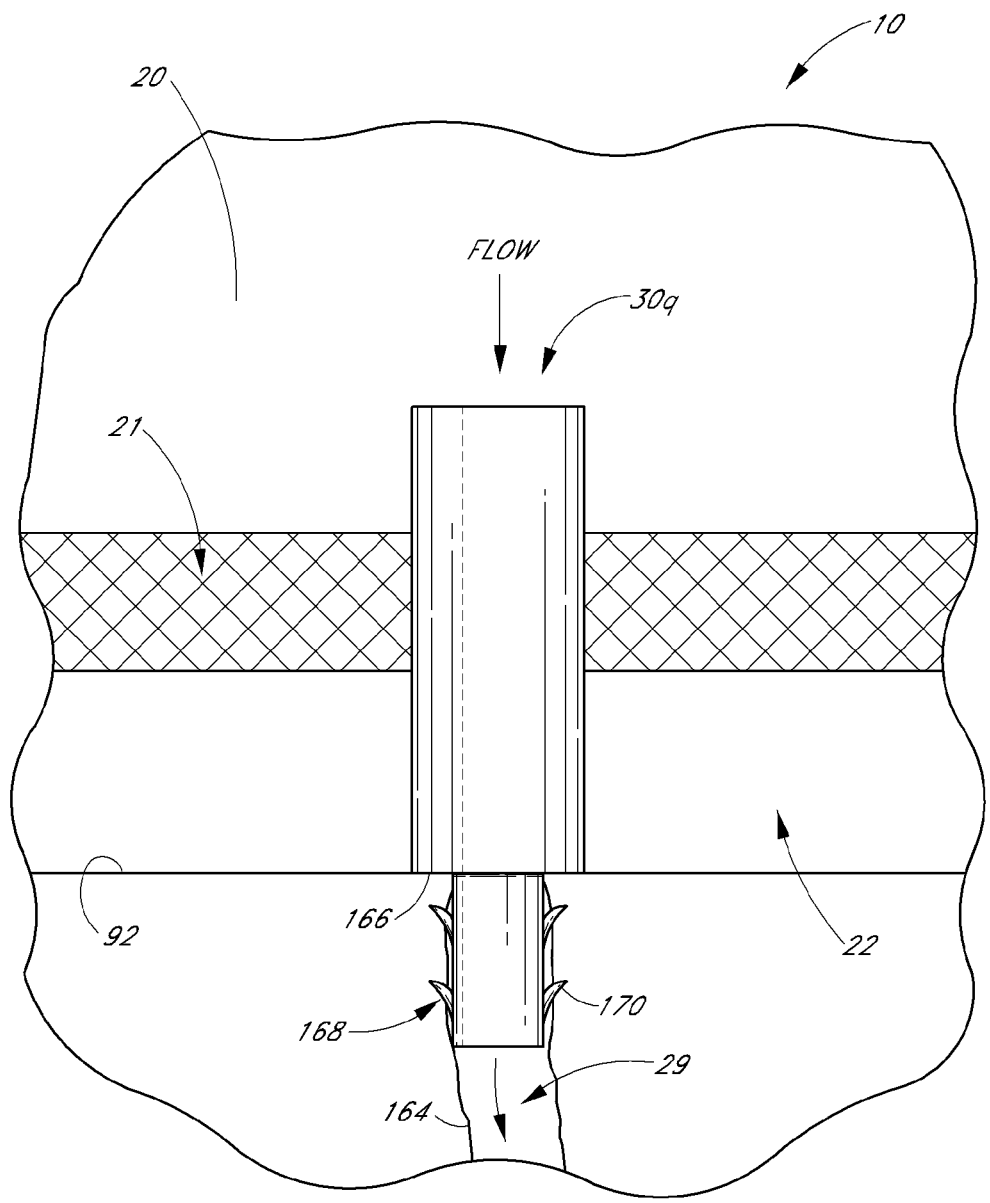
FIG. 42 is a simplified partial view of an eye illustrating the implantation of a glaucoma stent having features and advantages in accordance with one embodiment of the invention.

Barbed Stent (Anterior Chamber to Collector Channel):

FIG. 42 illustrates a glaucoma stent device 30*q* having features and advantages in accordance with one embodiment. This figure depicts an embodiment of a stent 30*q* that directs aqueous from the anterior chamber 20 directly into a collector channel 29 which empties into aqueous veins. The stent 30*q* has a base or distal end 166 and the channel 29 has wall(s) 164.

In the illustrated embodiment of FIG. 42, a barbed, small-diameter extension or pin 168 on the stent base 166 is guided into the collector channel 29 and anchors on the wall(s) 164 of the channel 29. The pin 168 has barbs 170 which advantageously provide anchoring of the stent 30*q*. The collector ducts 29 are nominally 20 to 100 micrometers (μm) in diameter and are visualized with a suitable microscopy method (such as ultrasound biomicroscopy (UBM)) or laser imaging to provide guidance for placement of the stent.

Referring to FIG. 42, in one embodiment, the stent 30*q* is inserted through a previously made incision in the trabecular meshwork 21. In other embodiments, the stent 30*q* may be combined with any of the blade configurations taught or suggested herein to provide self-trephining capability. In these cases, the incision through the trabecular meshwork 21 is made by the self-trephining stent device which has a blade at its base or proximate to the base.

Figure 43:
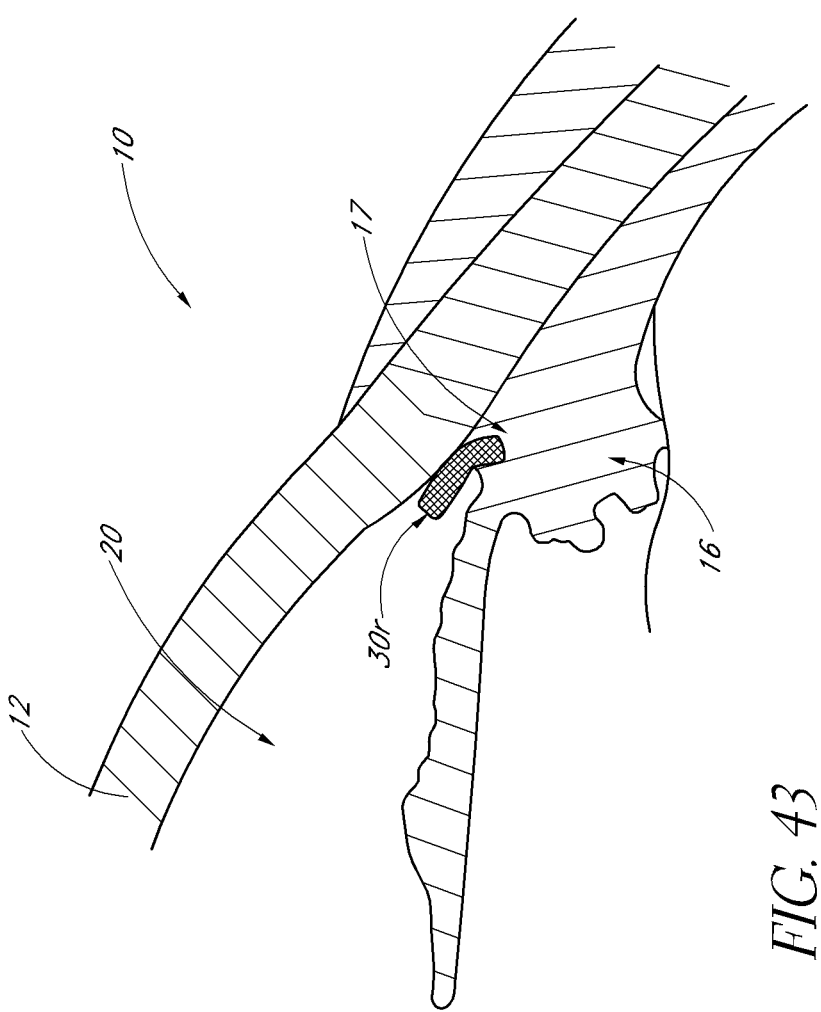
FIG. 43 is a simplified partial view of an eye illustrating the implantation of a valved tube stent device having features and advantages in accordance with one embodiment of the invention.

Valved Tube Stent (Anterior Chamber to Choroid):

FIG. 43 illustrates a valved tube stent device 30*r* having features and advantages in accordance with one embodiment. This is an embodiment of a stent 30*r* that provides a channel for flow between the anterior chamber 20 and the highly vascular choroid 17. Clinically, the choroid 17 can be at pressures lower than those desired for the eye 10. Therefore, this stent 30*r* includes a valve with an opening pressure equal to the desired pressure difference between the choroid 17 and the anterior chamber 20 or a constriction that provide the desired pressure drop.

Figure 44:
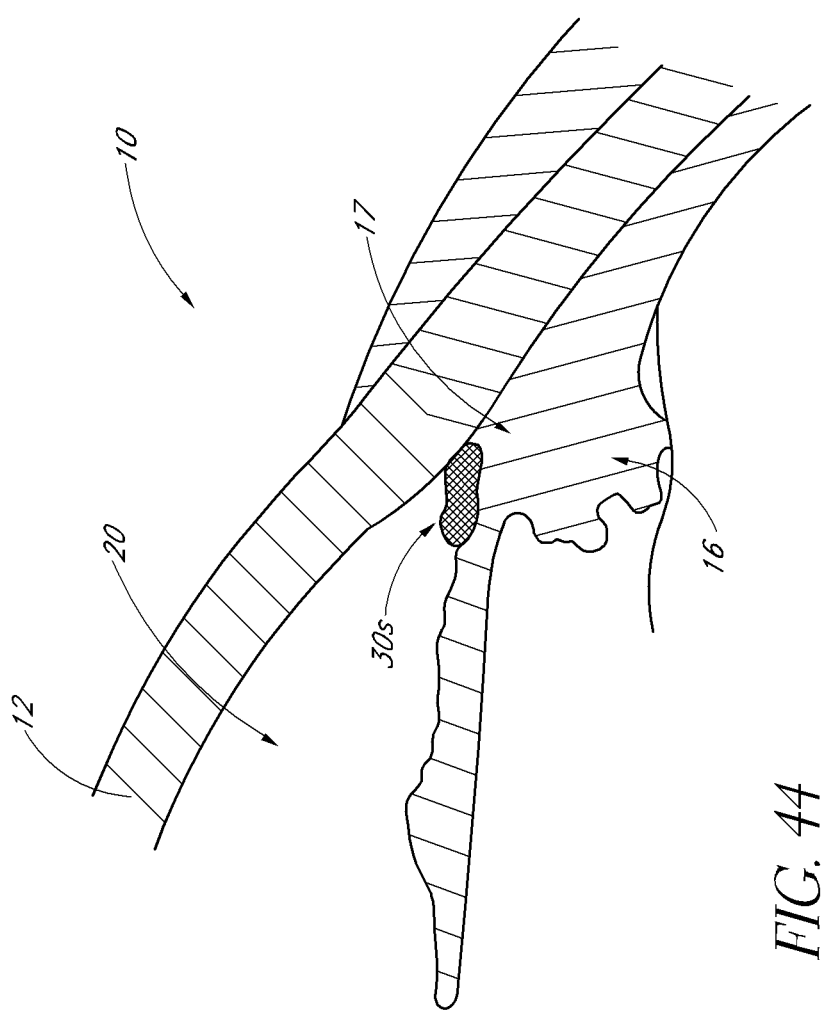
FIG. 44 is a simplified partial view of an eye illustrating the implantation of an osmotic membrane device having features and advantages in accordance with one embodiment of the invention.

Osmotic Membrane (Anterior Chamber to Choroid):

FIG. 44 illustrates an osmotic membrane device 30*s* having features and advantages in accordance with one embodiment. This embodiment provides a channel for flow between the anterior chamber 20 and the highly vascular choroid 17. The osmotic membrane 30s is used to replace a portion of the endothelial layer of the choroid 17. Since the choroid 17 is highly vascular with blood vessels, the concentration of water on the choroid side is lower than in the anterior chamber 20 of the eye 10. Therefore, the osmotic gradient drives water from the anterior chamber 20 into the choroid 17.

Clinically, the choroid 17 (FIG. 44) can be at pressures lower than those desired for the eye 10. Therefore, desirably, both osmotic pressure and the physical pressure gradient are in favor of flow into the choroid 17. Flow control is provided by proper sizing of the area of the membrane, —the larger the membrane area is the larger the flow rate will be. This advantageously enables tailoring to tune the flow to the desired physiological rates.

Figure 45:
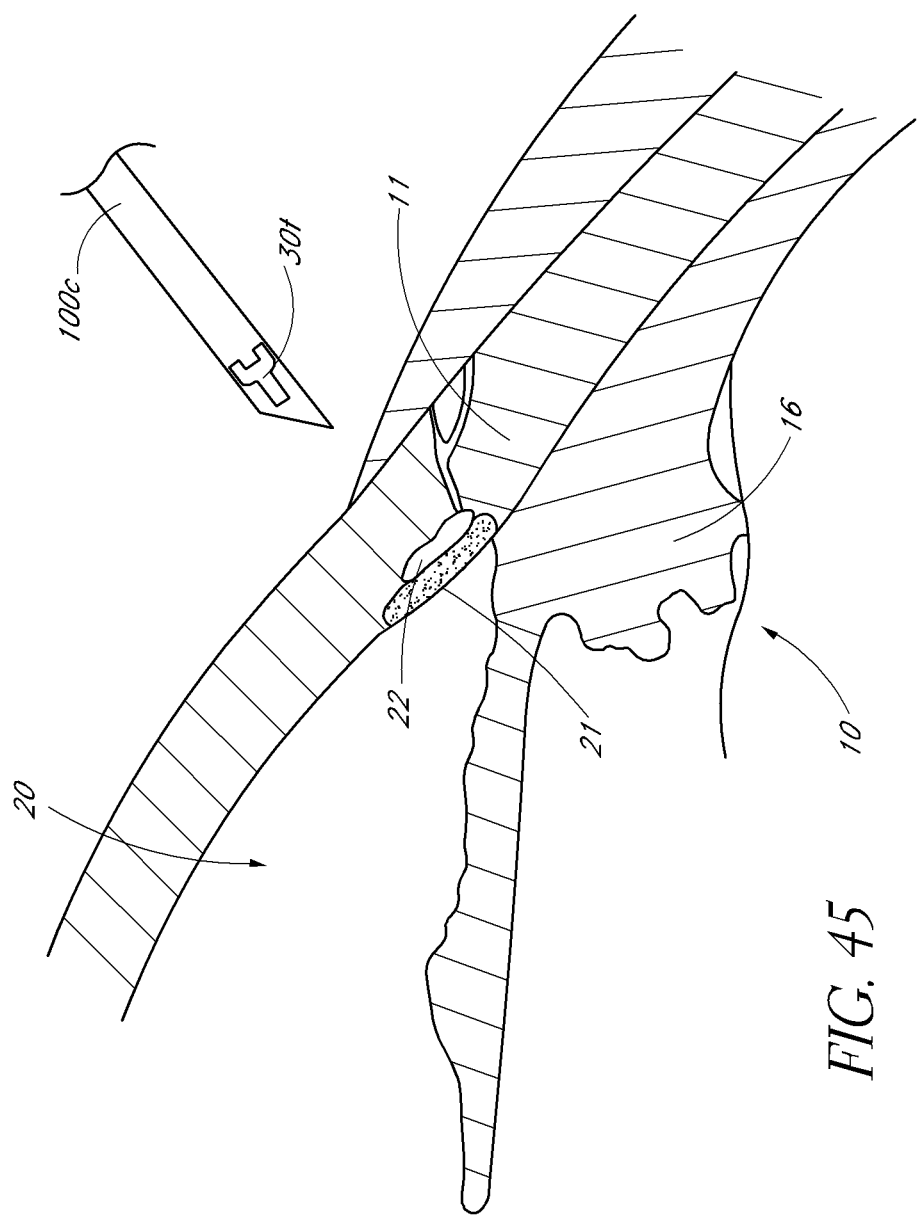
FIG. 45 is a simplified partial view of an eye illustrating the implantation of a glaucoma stent using ab externo procedure having features and advantages in accordance with one embodiment of the invention.

Ab Externo Insertion of Stent Via Small Puncture:

FIG. 45 illustrates the implantation of a stent 30t using an ab externo procedure having features and advantages in accordance with one embodiment. In the ab externo procedure of FIG. 45, the stent 30t is inserted into Schlemm's canal 21 with the aid of an applicator or delivery apparatus 100c that creates a small puncture into the eye 10 from outside.

Referring to FIG. 45, the stent 30t is housed in the applicator 100c, and pushed out of the applicator 100c once the applicator tip is in position within the trabecular meshwork 21. Since the tissue surrounding the trabecular meshwork 21 is optically opaque, an imaging technique, such as ultrasound biomicroscopy (UBM) or a laser imaging technique, is utilized. The imaging provides guidance for the insertion of the applicator tip and the deployment of the stent 30t. This technique can be used with a large variety of stent embodiments with slight modifications since the trabecular meshwork 21 is punctured from the scleral side rather than the anterior chamber side in the ab externo insertion.

Figure 46:
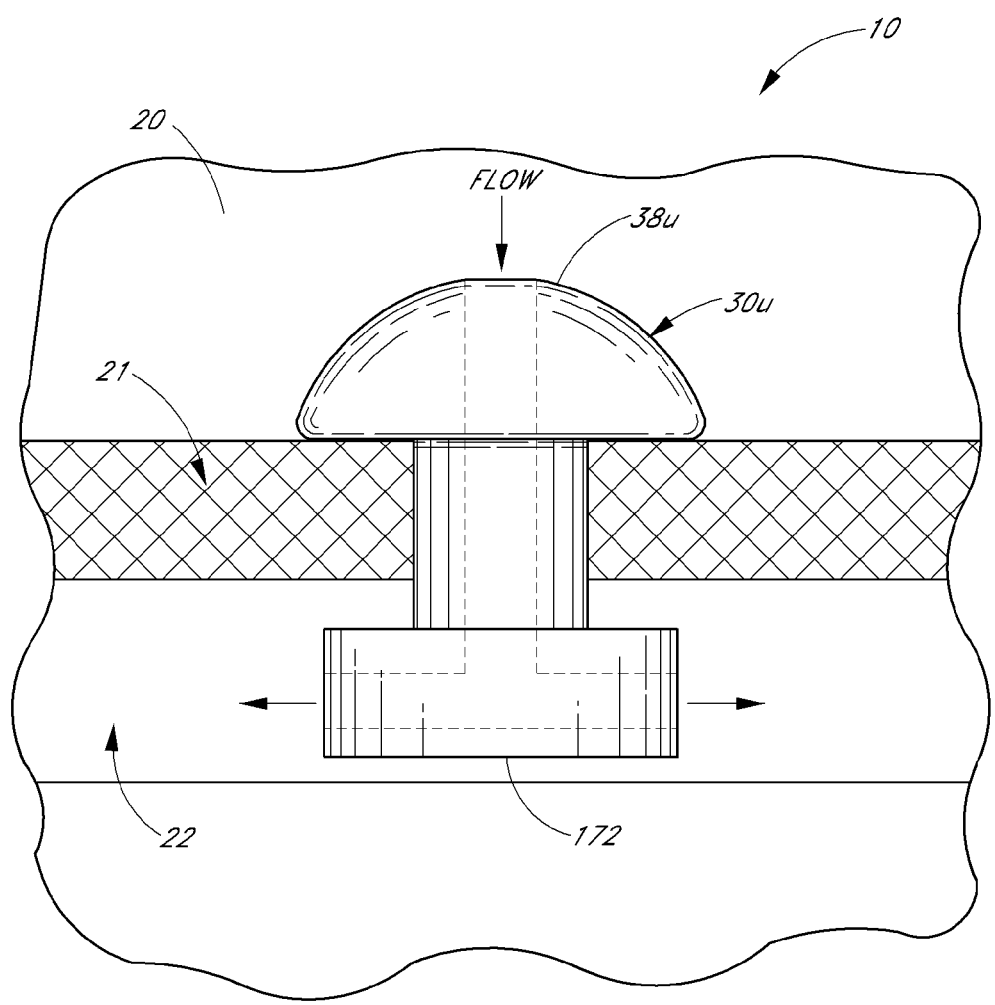
FIG. 46 is a simplified partial view of an eye illustrating the implantation of a glaucoma stent having features and advantages in accordance with a modified embodiment of the invention.

FIG. 46 a glaucoma stent device 30u having features and advantages in accordance with a modified embodiment. This grommet-style stent 30u for ab externo insertion is a modification of the embodiment of FIG. 36. In the embodiment of FIG. 46, the upper part or head 38u is tapered while the lower part or base 172 is flat, as opposed to the embodiment of FIG. 36. The stent 30u is inserted from the outside of the eye 10 through a puncture in the sclera. Many of the other embodiments of stents taught or suggested herein can be modified for similar implantation.

This ultra-microscopic device 30u (FIG. 46) can be used with (1) a targeting Lasik-type laser, or with (2) contact on eyes or with (3) combined ultrasound microscope or (4) other device insertor handpiece.

Figure 47:
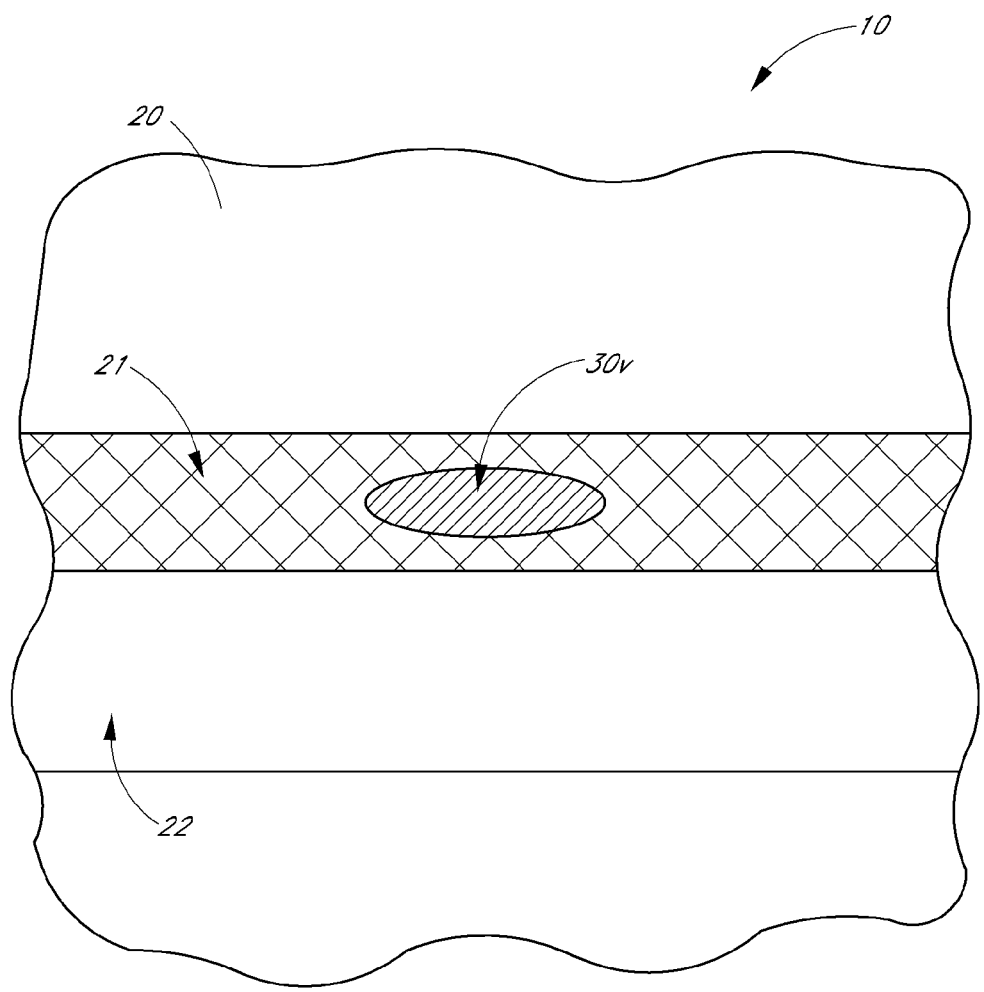
FIG. 47 is a simplified partial view of an eye illustrating the implantation of a drug release implant having features and advantages in accordance with one embodiment of the invention.

Targeted Drug Delivery to the Trabecular Meshwork:

FIG. 47 illustrates a targeted drug delivery implant 30v having features and advantages in accordance with one embodiment. This drawing is a depiction of a targeted drug delivery concept. The slow release implant 30v is implanted within the trabecular meshwork 21.

A drug that is designed to target the trabecular meshwork 21 to increase its porosity, or improve the active transport across the endothelial layer of Schlemm's canal 22 can be stored in this small implant 30v (FIG. 47). Advantageously, slow release of the drug promotes the desired physiology at minimal dosage levels since the drug is released into the very structure that it is designed to modify.

While the components and techniques of the invention have been described with a certain degree of particularity, it is manifest that many changes may be made in the specific designs, constructions and methodology herein above described without departing from the spirit and scope of this disclosure. It should be understood that the invention is not limited to the embodiments set forth herein for purposes of exemplification, but is to be defined only by a fair reading of the appended claims, including the full range of equivalency to which each element thereof is entitled.

Additional Disclosure

Other ways to close a valve other than pressure: concentration, expansion/contraction, pH
   Bypass directly to collector channels
      hollow dart
      pin guided tube welded or glued into place
      Stent to conjunctival space using a sterile filter for bacterial backflow/infection prevention
   Subchoroidal shunt with valve to prevent hypotony
   Use high salt concentrations (osmotic pump) to drive liquid through trabecular meshwork.
      + add drug to liquid going through to coat/repair cells.
   Another ab-externo approach wherein a sighting mechanism, such as ultrasonic and/or ultrabiomicroscope is used to locate Schlemm's canal in space, and drive an HTS type device through the external wall of Schlemm's and into the trabecular meshwork. Device could unfold so incision can be smaller in sclera/external Schlemm's than in internal Schlemm's wall. Sleeve/pushrod approach. Could be very short and uninvasive procedure requiring very little skill, provided the sighting technology was well done. Should compensate for eye movement, as is done with Lasik. Seal Schlemm's external wall wound with bioglue or bioadhesive, if necessary.
   A device placed into anterior chamber for slow release of drug to treat/cure outflow pathway. Replace or recharge device once or twice per year.
   Photodynamic response valve to synchronize outflow rate with natural diurnal variations.
   Ab-interno-to-temporal HTS implantation.
   A device that expands for improved seating into place. Activated by liquid contact (swells to final shape), or body heat (eg, nitinol).
   Develop a permeability test to measure outflow capacity directly, and use to design treatment.
   Develop a glaucoma assay that uses near-IR, Raman scattering or visible light methods to sense biochemical signals that could lead to glaucoma: metabolites, cell apoptosis, oxygen levels, pH, degredation products, etc.

Figure 52:
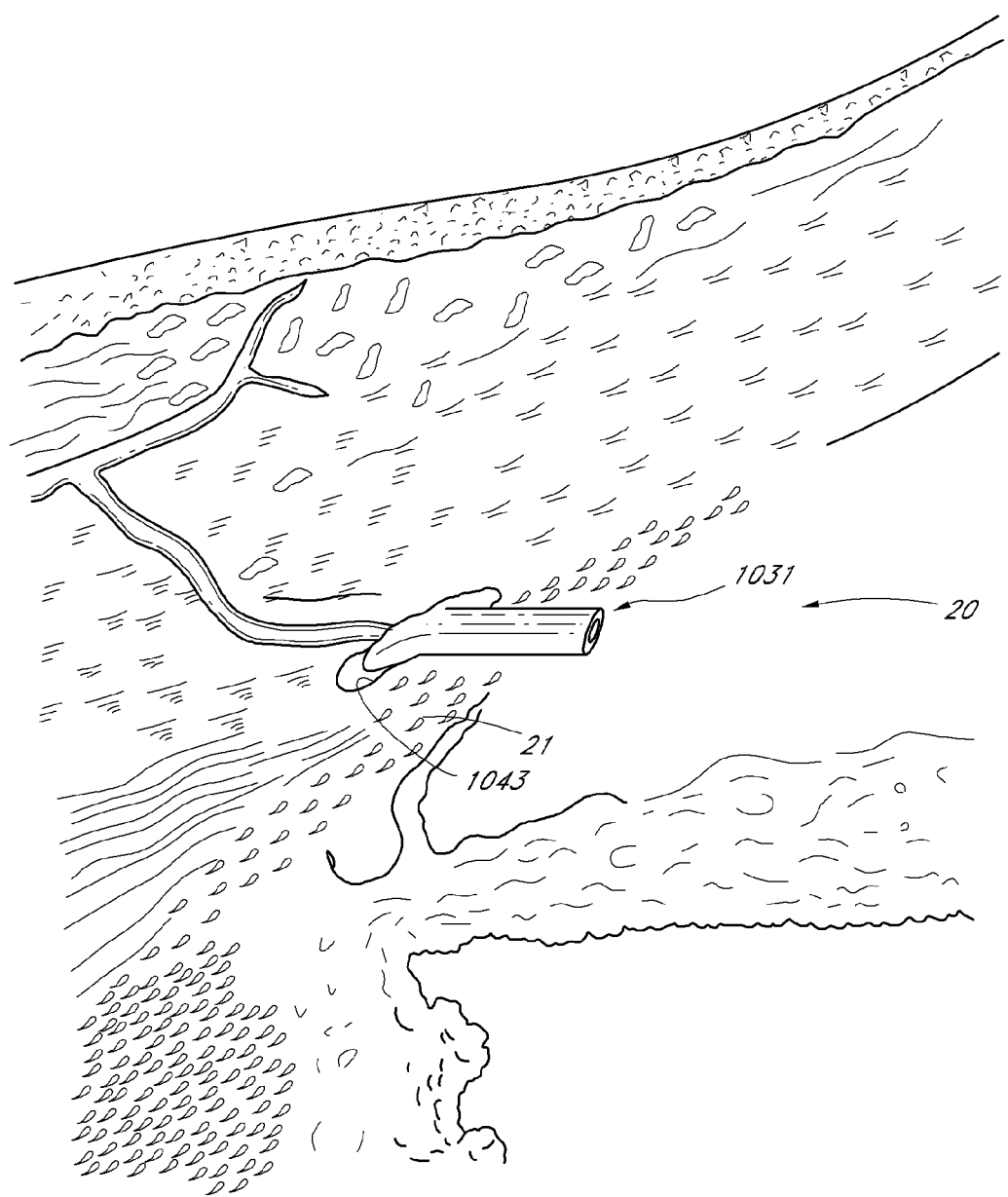
FIG. 52 is a perspective view illustrating a seton implant positioned within the tissue of an eye.

FIG. 52 shows a perspective view illustrating the seton implant 1031 of an embodiment of the present disclosure positioned within the tissue of an eye 10. A hole/opening is created through the diseased trabecular meshwork 21. The distal section of the seton implant 1031 is inserted into the hole/opening, wherein the inlet end is exposed to the anterior chamber 20 while the outlet end is positioned at about an exterior surface 1043 of said diseased trabecular meshwork 21. In a further embodiment, the outlet end may further enter into fluid collection channels of the existing outflow pathways.

In one embodiment, the means for forming a hole/opening in the trabecular mesh 21 may comprise an incision with a microknife, an incision by a pointed guidewire, a sharpened applicator, a screw shaped applicator, an irrigating applicator, or a barbed applicator. Alternatively, the trabecular meshwork may be dissected off with an instrument similar to a retinal pick or microcurrette. The opening may alternately be created by retrograde fiberoptic laser ablation.

Figure 53:
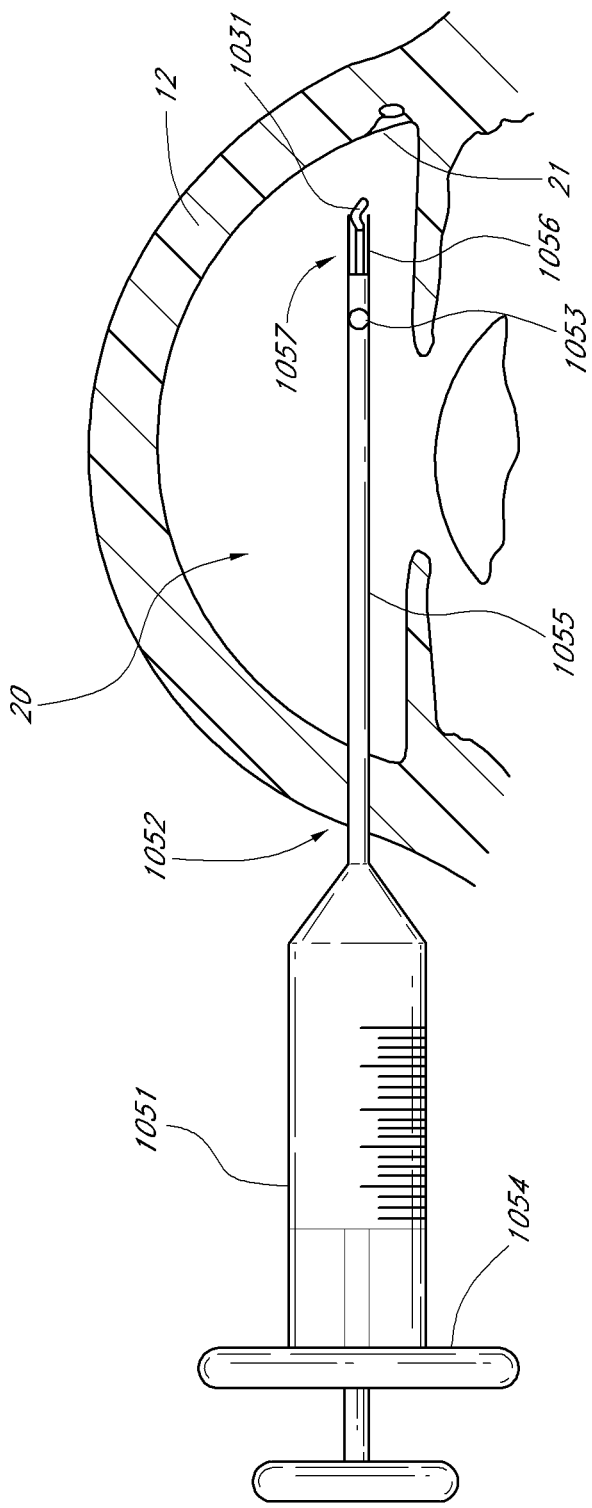
FIG. 53 is an alternate exemplary method for placing a seton implant at the implant site.

FIG. 53 shows an illustrative method for placing a seton implant at the implant site. An irrigating knife or applicator 1051 comprises a syringe portion 1054 and a cannula portion 1055. The distal section of the cannula portion 1055 has at least one irrigating hole 1053 and a distal space 1056 for holding a seton implant 1031. The proximal end 1057 of the lumen of the distal space 1056 is sealed from the remaining lumen of the cannula portion 1055.

For positioning the seton 1031 in the hole or opening through the trabecular meshwork, the seton may be advanced over the guidewire or a fiberoptic (retrograde). In another embodiment, the seton is directly placed on the delivery applicator and advanced to the implant site, wherein the delivery applicator holds the seton securely during the delivery stage and releases it during the deployment stage.

In an exemplary embodiment of the trabecular meshwork surgery, the patient is placed in the supine position, prepped, draped and anesthesia obtained. In one embodiment, a small (less than 1 mm) self sealing incision is made. Through the cornea opposite the seton placement site, an incision is made in trabecular meshwork with an irrigating knife. The seton 1031 is then advanced through the cornea incision 1052 across the anterior chamber 20 held in an irrigating applicator 1051 under gonioscopic (lens) or endoscopic guidance. The applicator is withdrawn and the surgery concluded. The irrigating knife may be within a size range of 20 to 40 gauges, preferably about 30 gauge.

Figure 54:
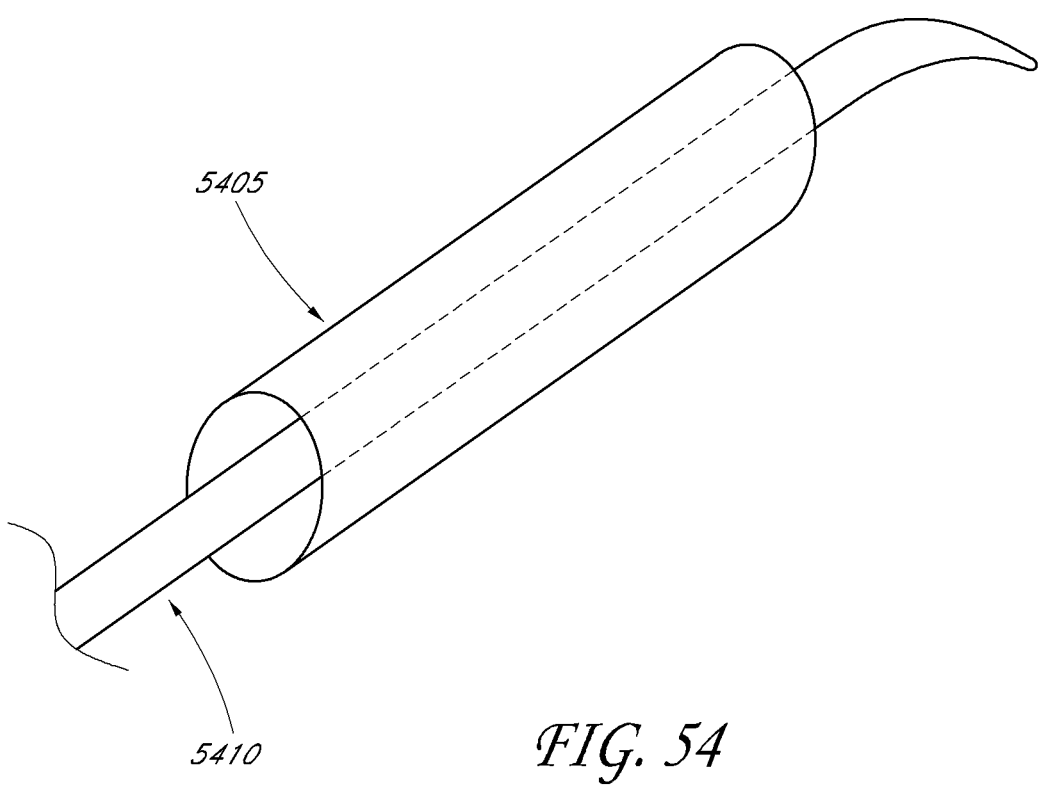
FIG. 54 illustrates a cut/install tool for forming a trabecular meshwork incision and for installing an intraocular pressure relief device.

FIG. 54 illustrates a cut/install tool 5410 configured to form an opening in eye tissue (e.g., a trabecular meshwork incision) and install an TOP relief device 5405. In the illustrated embodiment the device install tool 5410 is an elongate member having a bent tip. A portion of the device install tool may be configured to fit within a lumen of the TOP relief device 5405 to carry the TOP relief device 5405 as shown. In one embodiment, the device install tool 5410 is a needle (e.g. a 30-gauge needle).

What is claimed is:

1. A method of treating an ocular disorder comprising:
    forming an incision in a cornea or a corneal limbus of an eye to access an anterior chamber of the eye;
    introducing a shunt through the incision and into the anterior chamber of the eye using a delivery device;
    forming an opening in ocular tissue at an anterior chamber angle; and
    advancing the shunt from within the anterior chamber of the eye using a curved distal end portion of the delivery device, with an outlet portion of the shunt leading an inlet portion of the shunt, through the opening to an implantation location wherein at least a portion of the shunt is positioned between a sclera and a ciliary body of the eye while the shunt resides entirely within the confines of the sclera and the cornea of the eye and wherein a proximal end of the shunt is configured to reside in the anterior chamber when in the implantation location,
    thereby facilitating draining of fluid from the anterior chamber such that fluid flows into an inlet port of the inlet portion and out through one or more outlet ports of the outlet portion.

2. The method of claim 1, wherein advancing the shunt involves positioning the shunt so that a first portion of the outer circumferential surface of the shunt is in contact with the ciliary body of the eye and so that a second portion of the outer circumferential surface of the shunt opposite the first portion is in contact with the sclera.

3. The method of claim 1, wherein forming the incision involves forming a self-sealing incision.

4. The method of claim 3, wherein forming the opening in ocular tissue is performed using the delivery device.

5. The method of claim 3 additionally comprising removing the shunt from the delivery device by moving an actuator on a handpiece of the delivery device.

6. The method of claim 1, wherein forming the opening in ocular tissue is performed using the delivery device.

7. The method of claim 1, additionally comprising removing the shunt from the delivery device by moving an actuator on a handpiece of the delivery device.

8. The method of claim 1, additionally comprising actuating an actuator on a handpiece of the delivery device to cause a loaded spring within the handpiece to at least partially unload, thereby deploying the shunt from the delivery device.

9. A method of treating an ocular disorder, the method comprising:
    inserting an implant into an anterior chamber of an eye, the implant comprising an elongated body made of biocompatible material that extends between a proximal end and a distal end of the implant, the proximal end comprising an inlet port and the distal end comprising an outlet port, and a lumen extending from the inlet port to the outlet port;
    advancing the implant from within the anterior chamber of an eye to an anterior chamber angle of the eye using a delivery device having a curved distal end portion; and
    positioning the implant such that the proximal end of the implant resides within the anterior chamber and such that at least a portion of the implant, which is between the proximal end and the distal end of the implant, is in contact with a sclera and a ciliary body of the eye while the elongated body resides entirely within the confines of the sclera and a cornea of the eye,
    thereby facilitating drainage of aqueous humor out of the anterior chamber through the implant.

10. The method of claim 9, wherein said advancing the implant from within the anterior chamber of the eye to the anterior chamber angle of the eye comprises advancing the implant with the distal end leading the proximal end.

11. The method of claim 10, wherein said inserting the implant into the anterior chamber of the eye comprises inserting the implant through a self-sealing incision in the cornea.

12. The method of claim 11, wherein inserting the implant comprises inserting a tubular implant.

13. The method of claim 12, wherein said positioning the implant comprises positioning the implant so that a first portion of an outer circumferential surface of the implant is in contact with the ciliary body of the eye and so that a second portion of the outer circumferential surface of the implant is in contact with the sclera.

14. The method of claim 10, wherein inserting the implant comprises inserting a tubular implant.

15. The method of claim 14, wherein said positioning the implant comprises positioning the implant so that a first portion of an outer circumferential surface of the implant is in contact with the ciliary body of the eye and so that a second portion of the outer circumferential surface of the implant is in contact with the sclera.

16. The method of claim 10, additionally comprising removing the implant from the delivery device by moving an actuator on a handpiece of the delivery device.

17. The method of claim 9, additionally comprising actuating an actuator on a handpiece of the delivery device to cause a loaded spring within the handpiece to at least partially unload, thereby deploying the implant from the delivery device.

18. A system for shunting aqueous humor from an anterior chamber of a living human eye, the system comprising:
- an implant having an elongated body made of biocompatible material that extends between a proximal end and a distal end of the implant, at least a portion of the elongated body being implantable at a site between a sclera and a ciliary body of the eye while the elongated body resides entirely within the confines of the sclera and a cornea of the eye, the proximal end of the implant being configured to reside within an anterior chamber angle of the eye, and a lumen extending from at least one inlet port located at the proximal end of the implant, through at least a portion of the elongated body, and to one or more outlet ports located at or near the distal end of the implant so as to drain fluid from the anterior chamber of the eye; and
- a delivery device having an elongated member with a curved distal end portion, the implant being positionable on the elongated member with its one or more outlet ports disposed closer to a distal end of the elongated member than the at least one inlet port of the implant so as to advance the implant from within the anterior chamber to said site between the sclera and the ciliary body using an ab interno procedure.

19. The system of claim 18, wherein the delivery device is sized so as to fit through a self-sealing incision into the anterior chamber.

20. The system of claim 19, wherein the implant has a sufficient length such that the distal end of the implant contacts uveal tissue of the eye when implanted in the eye.

21. The system of claim 19, wherein the implant includes at least one anchor to inhibit movement of the implant once implanted with the portion of the elongated body located between the sclera and the ciliary body.

22. The system of claim 19, wherein the elongated member of the delivery device is pointed.

23. The system of claim 19, wherein the implant is configured such that when the proximal end of the implant is disposed within the anterior chamber of the eye, the distal end of the implant is in contact with the ciliary body.

24. The system of claim 19, wherein the one or more outlet ports drain into a uveoscleral outflow path of the eye.

25. The system of claim 19, wherein the delivery device comprises a spring within a handpiece of the delivery device, and wherein the spring is configured to be at least partially unloaded upon actuating an actuator on the handpiece, thereby allowing for release of the implant from the delivery device.

26. The system of claim 19, wherein the proximal end of the implant comprises a seat configured to facilitate stabilization of the implant.

27. The system of claim 26, wherein the seat is circular in shape.

28. The system of claim 19, wherein at least a portion of a length of the elongated body of the implant comprises retention members.

29. The system of claim 18, wherein the delivery device has a diameter sized to fit through an incision of 1 mm or less.

30. The system of claim 18, wherein the implant has a sufficient length such that the distal end of the implant contacts uveal tissue of the eye when implanted in the eye.

31. The system of claim 18, wherein the implant includes at least one anchor to inhibit movement of the implant once implanted with the portion of the elongated body located between the sclera and the ciliary body.

32. The system of claim 18, wherein the elongated member of the delivery device is pointed.

33. The system of claim 18, wherein the implant is configured such that when the proximal end of the implant is disposed within the anterior chamber of the eye, the distal end of the implant is in contact with the ciliary body.

34. The system of claim 18, wherein the one or more outlet ports drain into a uveoscleral outflow path of the eye.

35. The system of claim 18, wherein the proximal end of the implant comprises a seat configured to facilitate stabilization of the implant.

36. The system of claim 35, wherein the seat is circular in shape.

37. The system of claim 18, wherein at least a portion of a length of the elongated body of the implant comprises retention members.

38. The system of claim 18, wherein the delivery device comprises a spring within a handpiece of the delivery device, and wherein the spring is configured to be at least partially unloaded upon actuating an actuator on the handpiece, thereby allowing for release of the implant from the delivery device.

* * * * *